United States Patent
Peel, III et al.

(10) Patent No.: US 6,647,287 B1
(45) Date of Patent: Nov. 11, 2003

(54) DYNAMIC CARDIOVASCULAR MONITOR

(75) Inventors: Harry Herbert Peel, III, San Antonio, TX (US); Eiichi Inada, Tokyo; Masayuki Shinoda, Komaki, both of (JP); Franklin Tiffany Dodge, San Antonio, TX (US); Xiao Zhao, Kirkland, WA (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/549,611

(22) Filed: Apr. 14, 2000

(51) Int. Cl.$^7$ .......................... A61B 5/02; A61B 5/021; A61B 5/0402

(52) U.S. Cl. ........................................ 600/513; 600/485

(58) Field of Search .................................. 600/513, 485

(56) References Cited

U.S. PATENT DOCUMENTS 4,860,759 A * 8/1989 Kahn et al. .................. 600/481
5,265,011 A    11/1993 O'Rourke .................... 600/485
5,743,856 A     4/1998 Oka et al. .................... 600/493

FOREIGN PATENT DOCUMENTS

EP    0 655 219 A1   5/1995 ........... A61B/5/022

OTHER PUBLICATIONS

Kenmotsu et al., "Arterial Tonometry for Noninvasive, Continuous Blood Pressure Monitoring during Anesthesia", *Anesthesiology*, 1991, vol. 75, pp. 333–340.

Meyer–Sabellek et al., "Non–invasive ambulatory blood pressure monitoring: technical possibilities and problems", *Journal of Hypertension*, 1990, vol. 8 (suppl 6), pp. S3–S10.

Nielson et al., "Indirect Measurement of Systolic Blood Pressure by Strain Gauge Technique at Finger, Ankle and Toe in Diabetic Patients without Symptoms of Occlusive Arterial Disease", *Diabetologia*, 1973, vol. 9, pp. 25–29.

Taylor, "The Input Impedance of an Assembly of Randomly Branching Elastic Tubes", *Biophysical Journal*, 1966, vol. 6, pp. 29–51.

Avolio, "Multi–branched model of the human arterial system", *Medical & Biological Engineering & Computing*, Nov. 1980, vol. 18, pp. 709–718.

Taylor, "Wave Travel in Arteries and the Design of the Cardiovascular System", *Pulsatile Blood Flow*, ed. Attinger, McGraw Hill, New York,1 1964, pp. 343–367.

Taylor, "An Experimental Determination of the Propagation of Fluid Oscillations in a Tube with a Visco–elastic Wall; together with an Analysis of the Characteristics Required in an Electrical Analogue", *Physics in Medicine and Biology*, 1959, vol. 4, pp. 63–82.

Ocasio et al., "bpshape_wk4: a computer program that implements a physiological model for analyzing the shape of blood pressure waveforms", *Computer Methods and Programs in Biomedicine*, 1993, vol. 39, pp. 169–194.

(List continued on next page.)

Primary Examiner—Carl Layno
(74) Attorney, Agent, or Firm—Oliff & Berridge, PLC

(57) ABSTRACT

Methods and systems reconstruct and verify aortic blood pressure waveforms from peripheral blood pressure waveform data using mathematical models. The models combine analytical models of pulse wave propagation in the cardiovascular system with empirical models derived from measurements taken from human subjects. When used to reconstruct the aortic pressure of a given subject, the models are adjusted to the subject and the subject's physiological state based upon measurements performed on the subject's cardiovascular system.

28 Claims, 27 Drawing Sheets

OTHER PUBLICATIONS

Strano et al., "Measurement and Utilization of In Vivo Blood–Pressure Transfer Functions of Dog and Chicken Aortas", *IEEE Transactions on Biomedical Engineering*, Jul. 1972, vol. BME–19, pp. 261–270.

Lasance et al., "Peripheral Pulse Contour Analysis in Determining Stroke Volume" *Progress Report 5*, Inst. Med. Phys., Da Costakade 45, Utrecht, Netherlands, 1976, pp. 59–62.

Chen et al., "Estimation of Central Aortic Pressure Waveform by Mathematical Transformation of Radial Tonometry Pressure", *Circulation*, Apr. 1, 1997, vol. 95, No. 7, pp. 1827–1836.

Hori et al., "Estimation of Aortic BP Waveform from Non-invasive Radial Tonometry; Validation of FFT and ARX Methods" (abstract), Proceedings of the IEEE Engineering in Medicine and Biology, 1997.

Zhao et al., "Comparison of Direct and Indirect ARX Models for Aortic Blood Pressure Waveform Reconstruction" (abstract), Proceedings of the 1998 Annual Meeting of the Biomedical Engineering Society, Cleveland, Ohio, Oct. 1998.

Peel et al., "Feasibility of Aortic Waveform Reconstruction from Peripheral Waveforms Using ARX Models" (abstracts), Proceedings of the 1998 Annual Meeting of the Biomedical Engineering Society, Cleveland, Ohio, Oct. 1998.

Karamanoglu et al., "On–line Synthesis of the Human Ascending Aortic Pressure Pulse From the Finger Pulse", *Hypertension*, Dec. 1997, vol. 30, No. 6, pp. 1416–1424.

Steriopulos et al., "Physical basis of pressure transfer from periphery to aorta: a model–based study", *Am. J. Physiol.* (Hert Circ. Physiol. 43), 1998, pp. H1386–H1392.

Callaghan et al., "Relationship between pulse–wave velocity and arterial elasticity", *Medical & Biological Engineering & Computing*, May 1986, vol. 24, pp. 248–254.

Billings et al., "Least squares parameter estimation algorithms for non–linear systems", *Int. J. Systems Sci.*, 1984., vol. 15, No. 6, pp. 601–615.

Lane et al., "Pulse Transit Time and Blood Pressure: An Intensive Analysis", *Psychophysiology*, 1983, vol. 20, No. 1, pp. 45–49.

* cited by examiner

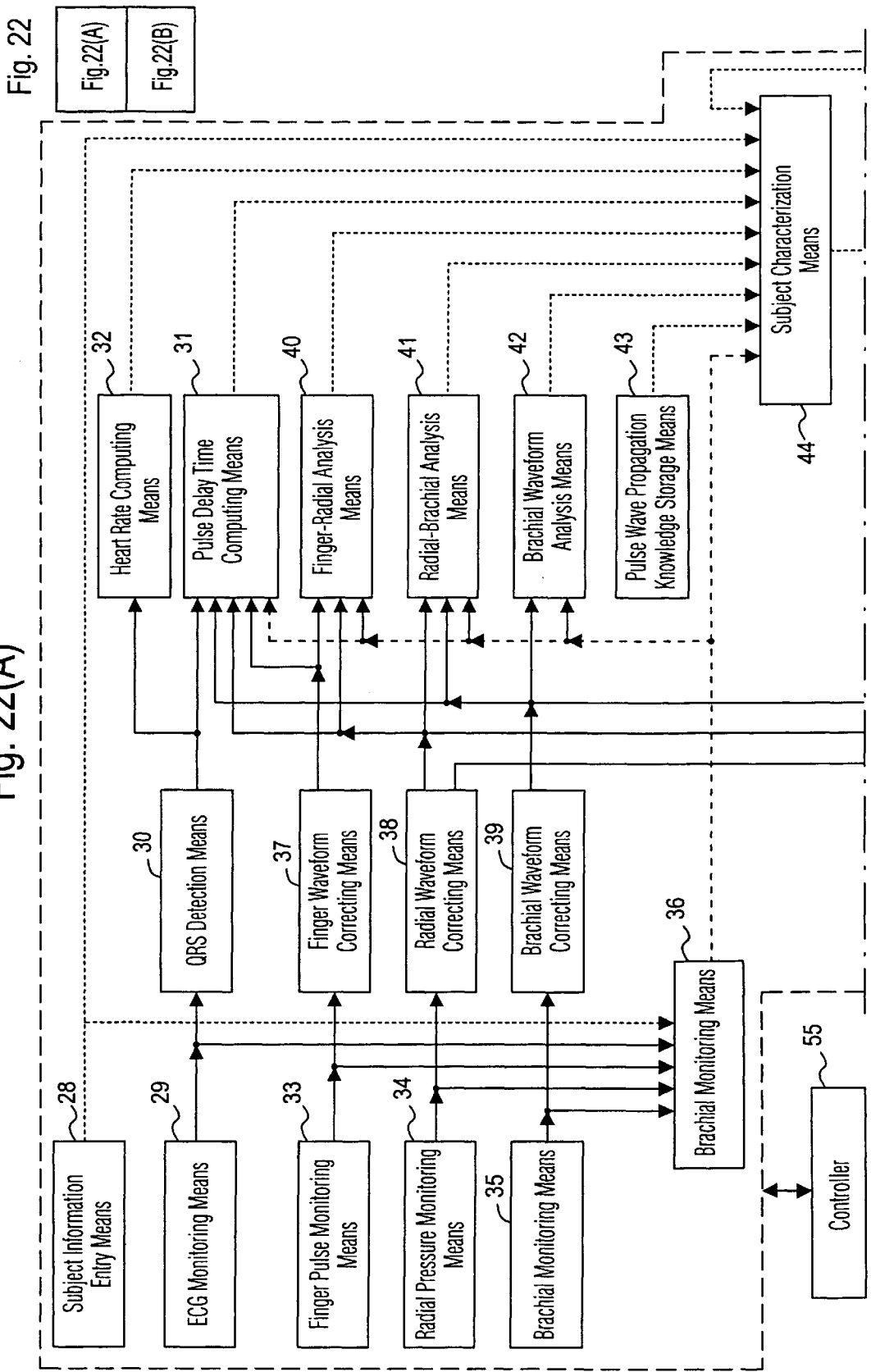

DYNAMIC CARDIOVASCULAR MONITOR

BACKGROUND OF THE INVENTION

1. Field of Invention

This invention relates to medical diagnostic and monitoring systems. More specifically, this invention is directed to a system and method for reconstructing an aortic blood pressure waveform using a model that is adapted to a specific subject.

2. Description of Related Art

Arterial blood pressure and heart rate are the principal variables used by medical personnel to assess and monitor cardiovascular function and identify adverse cardiovascular events. Such events include tachycardia, bradycardia, arrhythmias, hemorrhage and myocardial ischemia, among others. Ideally, medical personnel would continuously monitor the blood pressure at the root of the aorta, which is the primary driving source for blood flow throughout the body. As illustrated in FIG. 1, blood pressure is produced by the contraction of the heart 1, which ejects a volume of blood into the ascending aorta 2. The aorta 2 distributes the blood to the large arteries of the body, which in turn continually branch into smaller arteries to deliver the blood to the capillaries where oxygen and nutrients are delivered to the tissue. One of these branches is the left subclavian artery 3, which carries blood to the brachial artery 4 in the upper arm. The brachial artery divides into the radial artery 5 and the ulnar artery 6, which then rejoin in the hand from which the five digital arteries 7 emanate to supply the small arteries and capillaries 8 of the fingers.

Except in very special cases when insertion of a catheter into the aorta 2 is warranted for diagnostic purposes, blood pressure measurements are conducted in arteries located some distance from the heart. The most common blood pressure monitoring sites are the brachial artery, radial artery, and finger as illustrated in FIG. 1.

A wide range of patient monitoring devices has been developed for monitoring the blood pressure of patients. Patient monitors usually operate by methods and include devices that measure, analyze and display the electrocardiogram (ECG), intermittent non-invasive blood pressure (NIBP) measurement using a cuff, transcutaneous blood oxygen saturation (SpO2) measurement, continuous direct blood pressure (A-line) measurement, and, in some monitors, non-invasive continuous blood pressure measurement using tonometers.

NIBP monitors take blood pressure measurements periodically and provide numerical values for systolic blood pressure (SBP), mean aortic blood pressure (MBP), and diastolic blood pressure (DBP). When continuous blood pressure measurement is needed, it is continuously monitored with fluid-filled catheters connected to external pressure transducers. The catheter is normally placed in a peripheral vessel such as the radial artery. Continuous blood pressure monitoring can also be performed with tonometers that non-invasively monitor the pressure in a peripheral artery, e.g., the radial artery. (see, Kenmotsu, O., M. Ueda, H. Otsuka, T. Yamamura, D. C. Winter, and J. T. Eckerle, "Arterial Tonometry for Noninvasive, Continuous Blood Pressure Monitoring During Anesthesia," Anesthesiology, 1991, Vol. 75, pp 333–340, incorporated herein by reference in its entirety). Other methods have been reported in the literature that are able to provide continuous measurements and recording of the blood pressure in peripheral vessels in the arms and legs. (see, Meyer-Sabellek, W., Schulte, K. L., and Gotzen, R., "Non-invasive Ambulatory Blood Pressure Monitoring: Technical Possibilities and Problems," Journal of Hypertension, 1990, Vol. 8 (Suppl. 6), pp S3–S10, and Nielson, P. E., and Rasmussen, S. M., "Indirect Measurement of Systolic Blood Pressure by Strain Gage Technique at Finger, Ankle, and Toe in Diabetic Patients without Symptoms of Occlusive Arterial Disease," Diabetologia, 1973, Vol. 9, pp 25–29, incorporated herein by reference in their entireties).

However, it is well known that the actual blood pressure in peripheral arteries is different than that at the root of the aorta. (see, MacDonald, D. A., "Blood Flow in Arteries," London, Edward Arnold, 1960, and O'Rourke, Michael F., Raymond P. Kelly, and Alberto P. Avolio, *The Arterial Pulse*, Philadelphia & London, Lea & Febiger, 1992, both incorporated herein by reference in their entireties).

The MBP decreases slightly as the blood passes from the aorta through the large arteries to the smaller diameter, aortic and radial branches of the arterial tree. As shown in FIG. 1, the pulse pressure increases in amplitude as it passes through the aortic to radial arterial branches after which it begins to decrease in amplitude. (see, Fung, Y. C., *Biodynamics: Circulation*, Spinger-Verlag, New York, Berlin, Heidelberg, Tokyo, 1984, p.134, incorporated by reference in its entirety). The increase in pulse pressure, or amplification, usually exceeds the small drop in mean blood pressure resulting in an increase in the systolic (maximum) pressure and a smaller magnitude decrease in the diastolic (minimum) pressure. In addition, the shape of the arterial pulse waveform is altered as it passes from the aorta to the periphery. As a result, the pressures measured at peripheral sites may not accurately represent the pressure at the root of the aorta. These amplifications and alterations of the waveform shape have been widely studied and reported by a number of investigators. These changes are caused by the compliant nature of the blood vessels, the terminal impedance of each arterial branch, and wave reflections produced at bifuircations. (see, Taylor, M. G. "Wave Travel in Arteries and the Design of the Cardiovascular System." In Pulsatile Blood Flow, ed. Attinger, E. O., McGraw Hill, N.Y., 1964, pp 343–367, incorporated by reference in its entirety).

Modeling studies have taken three approaches to identifying change in an arterial pulse as the pulse propagates.

A first conventional approach has been to develop mathematical descriptions of the physical structure of the vascular system. These models have taken the form of collections of tubes of varying complexity, (see, Taylor, M. G. "The Input Impedance of an Assembly of Randomly Branching Elastic Tubes," Biophysical Journal, Vol. 6, 1966, pp 29–51 and Avolio, A. P. "Multi-branched Model of the Human Arterial System," Medical & Biological Engineering & Computing, Vol. 18, November 1980, pp 709–718, incorporated by reference in their entireties) and lumped parameter models. (see, Taylor, M. G. "An Experimental Determination of the Propagation of Fluid Oscillations in a Tube with a Visco-elastic Wall; Together with an Analysis of the Characteristics Required in an Electrical Analogue," Physics in Medicine and Biology, Vol. 4, 1959, pp 62–82, and Ocasio, Wendell C., David R. Rigney, Kevin P. Clark, and Roger G. Mark, "bpshape_wk4: A Computer Program that Implements a Physiological Model for Analyzing the Shape of Blood Pressure Waveforms," Computer Methods and Programs in Biomedicine, Vol. 39 (1993) pp. 169–194, both incorporated by reference in their entireties). Measurements of the cardiovascular system (e.g., vessel dimensions, tissue elasticities, etc.) are then used to develop the coefficients of the model equations. Using the model equations, the approach is able to determine characteristics of the cardiovascular system by modeling the aortic pulse at the aorta root using the characteristics of the aorta pulse at the peripherial artery.

However, this approach is severely limited because of the complexity of the vascular system and the number of parameters that must be known. Most importantly, the cardiovascular system is non-linear and its physical properties vary depending upon the patient's physiological state at the time of measurement.

A second conventional approach uses lumped parameter elements that represent the major resistive and reactive elements of the vascular system. (see, Strano, Joseph J., Walter Welkowitz, and Sylvan Fich, "Measurement and Utilization of In Vivo Blood-Pressure Transfer Functions of Dog and Chicken Aortas," IEEE Transactions on Biomedical Engineering, Vol. BME-19, No. 4, July 1972. pp 261–270 incorporated herein in its entirety). This approach allows representation of large portions of the vascular system with relatively few components while providing finer detail in an area of interest. Aortic and peripheral blood pressure data are then used to determine the constants or parameters of the lumped parameters by any number of curve fitting techniques. This approach is useful when information (e.g., the parameters) relating to the major components of the system or a specific segment of the system is of interest.

The third approach essentially models the arterial system as a black box with the aortic blood pressure pulse as the input signal and the peripheral blood pressure pulse as the output signal. Input-output models such as the black box approach have the advantage that no physical knowledge of the arterial system is required. Further, the black box modeling technique requires an assumption that the modeled system is inherently linear. Therefore, the linearity assumption allows the system to be modeled in either direction; that is, the peripheral pulse pressure can be assumed to be the input and the aortic pulse pressure the output or vice versa.

Several mathematical methods have been used to develop an empirical model that describes the workings of the black box. The most common method is the computation of the system's transfer function in the frequency domain using Fourier transform methods. This technique, widely used in electronics analysis, has been applied to arterial pulse propagation by a number of subjects. (see, for example, Lasance, H. A. J., K. H. Wesseling, C. A. Ascoop, "Peripheral Pulse Contour Analysis in Determining Stroke Volume," Progress Report 5, Inst. Med. Phys., Da Costakade 45, Utrecht, Netherlands, 1976 and U.S. Pat. No. 5,265,011 issued to O'Rourke on Nov. 23, 1993, incorporated by reference in their entireties).

One method for using Fourier methods is described in U.S. Pat. No. 5,265,011. In this patent, the aortic and radial waveforms are obtained from a large number of subjects. The transfer function is then computed from the aorta to the radial artery for each subject using the Fourier transform approach. All of the transforms are then averaged to obtain an average aortic-to-radial transform for the sample population. The universal transform is inverted such that the measured radial waveform is the input and the aortic waveform is the output of the inverse transform. The inverse transform is then transformed back into the time domain to produce a model that provides an estimate of the aortic waveform from the radial waveform.

Input-output models equivalent to the black box technique can be developed in the time-domain using auto-regressive methods (see, Chen, Chen-Huan, et. al., "Estimation of Central Aortic Pressure Waveform by Mathematical Transformation of Radial Tonometry Pressure: Validation of Generalized Transfer Function," Circulation, Vol. 95. No. 7, Apr. 1, 1997, pp. 1827–1836, incorporated herein by reference in its entirety) that use aortic and radial pressure data from a large number of subjects to develop time domain models of the aortic-to-radial waveform propagation. The individual models are transformed into the frequency domain and the resulting transfer functions are averaged as performed in U.S. Pat. No. 5,265,011. The average transfer functions are then inverted and transformed back into the time domain to produce a linear equation that estimates the aortic waveform from the radial waveform.

Use of auto-regressive methods to compute individual aortic to radial model in the time domain is also conventionally known. (see, Hori, Chiori, et.al., "Estimation of Aortic BP Waveform From Noninvasive Radial Tonometry; Validation of FFT and ARX Methods," Proceedings of the IEEE Engineering in Medicine and Biology, 1997, incorporated herein by reference in its entirety). However, Hori et al. perform averaging and inversion in the time domain to produce the average radial-to-aortic model.

Auto-regressive models have been developed for reconstructing aortic waveforms from radial waveforms in baboons. (see, Zhao, Peel, Edgar, and Inada, "Comparison of Direct and Indirect ARX Models for Aortic Blood Pressure Waveform Reconstruction," (Abstract) Proceedings of the 1998 Annual Meeting of the Biomedical Engineering Society, Cleveland, Ohio, October, 1998, incorporated herein by reference in its entirety). These models differ from those of earlier investigators in that the radial blood pressure is used as the input to the model and the aortic blood pressure is used as the output. This approach avoids introduction of errors that occur during the inversion of the aortic-to-radial model to produce the radial-to-aortic model. Further, the modeling uses composite radial and aortic signals constructed by concatenating signals from many subjects.

These empirical approaches produce models that are, in essence, averages of the wave propagation characteristics of the subjects comprising the sample population. An example of such an average transfer function from a group of 10 subjects is shown in FIG. 2. When the number of subjects is large and the subjects represent the population as a whole, it is assumed that such models provide reconstructed waveforms of acceptable accuracy in most, if not all, people. This is not, however, the case.

FIG. 3 shows the individual transfer functions for the 10 subjects used to form the average transfer function shown in FIG. 2. As can be readily seen, there is a large variation in both the magnitude and phase relationships between the subjects. As a result, use of an average model produces poor reconstructed aortic blood pressure in subjects who differ from the average of the population. Moreover, the normal variation between subjects is sufficient to produce medically significant errors in estimated blood pressure. (see, Peel, Zhao, Edgar, and Inada, "Feasibility of Aortic Waveform Reconstruction Using ARX Models," (Abstract), Proceedings of the 1998 Annual Meeting of the Biomedical Engineering Society, Cleveland, Ohio, October, 1998; Karamanoglu, Mustafa and Micheal P. Fenely, "On-line Synthesis of the Human Ascending Aortic Pulse From the Finger Pulse," Hypertension, Vol. 30, No. 6, December 1997, pp 1416–1424; and Stergiopulos, Nikos, Berend E. Westerhof, and Nico Westerhof, "Physical Basis of Pressure Transfer From Periphery to Aorta: a Model-based Study,"

Am. J. Physiol. (Hert Circ. Physiol. 43), H1386–1392, 1998, incorporated herein by reference in their entireties). Further, changes in the cardiovascular state within a subject can produce even more significant errors because the approach is affected by the subject's physiological state. This inherent inaccuracy of average aortic blood pressure reconstruction models severely limits their medical usefulness.

The differences between subjects are a result of the normal physiological differences (e.g., age, vessel properties, etc.) and anatomical differences (e.g., height, weight, sex, etc.) between subjects. Furthermore, the transfer functions for a given subject can change for differing conditions of their cardiovascular system. Within any particular subject, differences are due to changes in the subject's physiological state (e.g., vasomotor tone, heart rate, peripheral resistance, etc.) that can be produced by disease, introduction of medications, stress, and many other factors.

One approach to producing more accurate estimates of central aortic pressure is to use a mathematical model of the pulse wave propagation path that can be adjusted to a specific subject. One conventional method in accordance with this approach produces a partially individualized model. It uses a linear acoustic model that assumes the pulse propagation path to be a linear combination of viscoelastic tubes terminating in an Windkessel impedance. (see, Karamanoglu, M. and Feneley, M., "On-line Synthesis of the Human Ascending Aortic Pressure Pulse from the Finger Pulse", Hypertension, 1997, Vol. 30, No. 6, pp 1416–1424, incorporated by reference herein in its entirety). The model first mathematically relates the finger pulse pressure, as measured with a finger cuff blood pressure monitor, to the carotid artery pressure. The aortic pressure is then estimated from the estimated carotid pressure. The parameters of the finger to carotid artery model are estimated using simultaneous measurements of the finger blood pressure and the carotid blood pressure made with a hand-held tonometer. The aortic pressure is estimated from the estimated carotid artery pressure using a population-based, average transfer function of the aortic-to-carotid pulse propagation path.

A second conventional approach for producing an individualized aortic reconstruction model uses a single linear tapered tube model that relates the aortic pressure to the pressure and flow velocity at a point in the peripheral vascular system. (see, Stergiopulos, Nikos, Berend E. Westerhof, and Nico Westerhof, "Physical Basis of Pressure Transfer From Periphery to Aorta: a Model-based Study," Am. J. Physiol. (Hert Circ. Physiol. 43): H1386–1392, 1998, incorporated by reference herein in its entirety). The model, which estimates the forward and reflected wave transfer functions, is adjusted by estimating the parameters of the tapered tube model from simultaneous measurements of blood pressure and flow velocity at the peripheral site. However, this model is limited to sites that have no major bifurcations (e.g., the radial-ulnar split of the brachial artery) in the propagation path. This limitation is due to the simple, single tube model that is not representative of many peripheral sites. Finally, this model has only been evaluated with simulated aortic and peripheral waveforms produced by a model of the circulatory system.

The empirical universal models and individualized analytical models, while different in the model constructs and pressure measurements used, all assume the cardiovascular system to be linear. Wave propagation in the vascular system is non-linear and the models only work well over limited ranges of cardiovascular states. Moreover, some of the measurements (specifically hand-held tonometry and flow velocity monitoring) are not clinically useful methods for continuous patient monitoring. Finally, and most importantly, the models are limited by their coarse characterization of the vascular system; that is, the conventional approaches that attempt to personalize the model to the subject also attempt to characterize the propagation path solely from the two pressures measured at the aorta and the peripheral measurement site.

A common feature of conventional methods that model wave propagation in the peripheral arteries with linear models is the assumption of linearity, i.e., that the cardiovascular system may be accurately modeled as a linear system, and the assumption of stationarity, i.e., the invariance of the arterial system over time and subjects. The assumption of linearity is generally valid if the range of pressure variations is small. The assumption of stationarity is valid provided that assumptions about the state of a cardiovascular system do not change over patients or over time. However, it is conventionally understood these assumptions do not hold for physiological systems.

The most notable source of non-linearity in the cardiovascular system is the dependence of the vessel wall elasticity and compliance on the instantaneous blood pressure and vasomotor tone. (see Callaghan, F. J., L. A. Geddes, C. F. Babbs, and J. D. Bourland, "Relationship Between Pulsewave Velocity and Arterial Elasticity," Med. & Biol. Eng. & Comput., 1986, Vol. 24, pp 248–254, incorporated by reference in its entirety). Vessel wall elasticity is also a function of age and possibly gender. Damping, while usually ascribed to viscous losses in the vessel wall and fluid viscosity, is also influenced by the adhesion, or tethering of the vessel to the surrounding tissue. The surrounding tissue also contributes elastic and inertial components to the wall elasticity; these factors are heavily dependent upon body morphology and muscle tone. The resistive component of tube models is assumed to be a constant. However, the pressure drop in fluid systems is a function of the square of the flow velocity and produces a varying resistance over the period of a blood pressure pulse because the blood flow varies widely over the cardiac cycle.

Further, the structure of the arterial tree is a source of non-linearity. The arterial tree is a continuously branching system of tubes rather than the simple series of tubes assumed by most conventional models. Each major arterial branch includes sub-branches at which the primary artery splits into two or perhaps three sub-branches. As a general rule, the daughter tubes, i.e., the sub-branches produced by branching, at major bifurcations, are smaller in diameter than the parent tube. However, the daughter tubes also have a combined cross-sectional area that is larger than the parent tube.

The principal effect at major branching is the large difference in the forward and reverse impedances. Therefore, reflections are produced at major branch bifurcations. Between these major branch bifurcations, there are many smaller side branch tubes that have cross-sectional areas that are much smaller than the parent tube. The geometry of a subject's arterial tree can be changed by changes in body position, which introduce significant bends into the tubes and, which may partially or completely occlude one or more branches. Moreover, the geometry of the branching is highly variable between subjects.

SUMMARY OF THE INVENTION

The assumption of stationarity is the greatest shortcoming of conventional models for aortic blood pressure reconstruction. This is because the cardiovascular system is highly dynamic and has numerous control mechanisms for adapting to the changing metabolic needs of the subject. These control mechanisms alter not only the heart rate and stroke volume, but also the mechanical characteristics of the large and small vessels. The vascular changes influence the pulse wave propagation velocity, vessel resistance and the terminal impedance of the pulse wave propagation path. Vascular control mechanisms also respond to medications, disease processes, and blood loss. As a result, aortic blood pressure reconstruction requires a model that is adaptable to a subject and adjustable to changes in a subject's state. This requires monitoring of the subject's cardiovascular state and a device for adapting the reconstruction model to the changes in cardiovascular state. The invention is directed at providing such an adaptable and adjustable aortic blood pressure reconstruction model.

Conventional models that predict aortic pressure from peripheral pressures have been only partially successful, in part, because of sources of variability, both between subjects and within a subject over time. These shortcomings of the conventional aortic blood pressure reconstruction are overcome by the present invention.

In an exemplary embodiment of the invention, other physiological measurements are performed in conjunction with continuous A-line or tonometer blood pressure monitoring. For example, the exemplary embodiments use the ECG, NIBP, and oximetry. Specifically, the ECG provides a time reference for the start of each blood pressure pulse as it leaves the root of the aorta. The occlusion cuff of a NIBP monitor serves as a plethysmograph, which can produce brachial blood pressure waveforms when the pressure is held constant at a low pressure. Pulse oximeters, as part of their measurement apparatus, produce a continuous plethysmographic measurement of the blood pressure waveform in the finger. The shortcomings of conventional linear models are overcome using the measurements provided by the ECG, the occlusion cuff of the NIBP monitor and the pulse oximeters.

Accordingly, the invention relates to methods and systems for reconstructing and verifying aortic blood pressure waveforms from peripheral blood pressure waveform data using mathematical models. These mathematical models combine analytical models of pulse wave propagation in the cardiovascular system with empirical models derived from measurements taken from a population of human subjects and from the individual subject being modeled. When used to reconstruct the aortic pressure of a given subject, the mathematical models are adjusted to the subject and the subject's physiological state based upon measurements performed on the subject's cardiovascular system.

An empirical aortic waveform reconstruction model is obtained from measurements performed on a large population of subjects. The empirical models are personalized to subjects by normalizing the model using the subjects' wave-propagation characteristics and other information. Subsequently, the normalized empirical models are combined into a single population average normalized model. The normalization is performed with the aid of mathematical descriptions of the vascular system and measurements that account for individual variations, non-uniformities, and non-linearities of the cardiovascular system. When used for reconstruction of a specific subject's aortic blood pressure, the general, normalized model is adjusted using measurements performed on the specific subject. The reconstructed aortic waveform is verified by using it to reproduce the waveform at one point in the vascular system and comparing that waveform to a waveform measured at that point.

DETAILED DESCRIPTION OF PREFERRED EMBODIMENTS

The system and method according to the invention require that the pressure pulses produced in a cuff by the volume change of the underlying artery be continuously measured for one or more heart cycles at two or more cuff pressures.

Reconstruction of the aortic blood pressure requires a mathematical relationship of aortic blood pressure to a known pressure at some other point in the cardiovascular system. For example, in an exemplary embodiment, the brachial, radial, or phalangeal (finger) artery blood pressures are the specific peripheral blood pressures used. However, the exemplary use of those blood pressures is not meant to restrict the scope of the invention because the methods described herein can be applied to other arterial branches. The mathematical relationship of the aortic pressure to the radial pressure is of the form:

$$p_a(t-\tau_{ar}) = f(p_r(t), p_b(t_c), p_r(t_c), p_f(t_c), \tau_{ab}, \tau_{ar}, \tau_{af}, C(I)) + P_r(t-\tau_{ar}) \quad (1)$$

where:

$p_a(t-\tau_{ar})$=the instantaneous reconstructed blood pressure, $p_r(t)$=the instantaneous radial blood pressure, $p_b(t_c)$=the brachial blood pressure at the time of calibration, $p_r(t_c)$=the radial blood pressure at the time of calibration, $p_f(t_c)$=the finger blood pressure at the time of calibration, $t_c$=the time of calibration of the function $f$, $\tau_{ar}$=the propagation time of the pulse from the aorta to the radial artery, $\tau_{ab}$=the propagation time of the pulse from the aorta to the brachial artery, $\tau_{af}$=the propagation time of the pulse from the aorta to the finger artery C(I)=a set of subject characteristics consisting of patient indices, I, and $P_r(t-\tau_{ar})$=the mean radial blood pressure.

The function, $f$, reconstructs the aortic pulse pressure waveform to which is added the mean radial pressure to produce the estimate of total aortic blood pressure. The function, $f$, consists of a linear model describing the propagation of the blood pressure pulse from the aorta to the radial artery. The linear model is first formulated to represent the cardiovascular system and then applied to a subject, as discussed herein.

Figure 1:
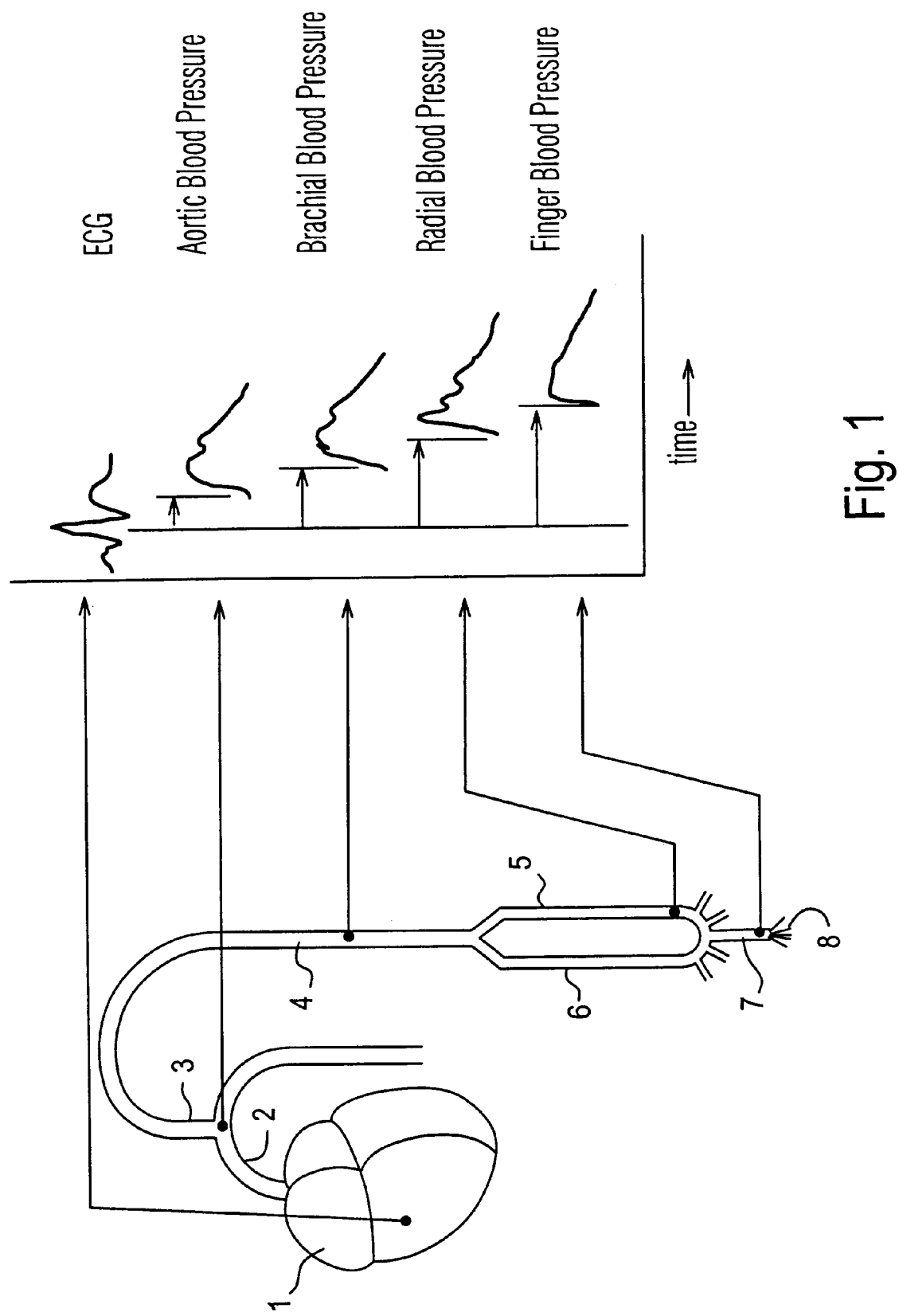
FIG. 1 illustrates the blood pressure produced by the contraction of the heart.
Figure 2:
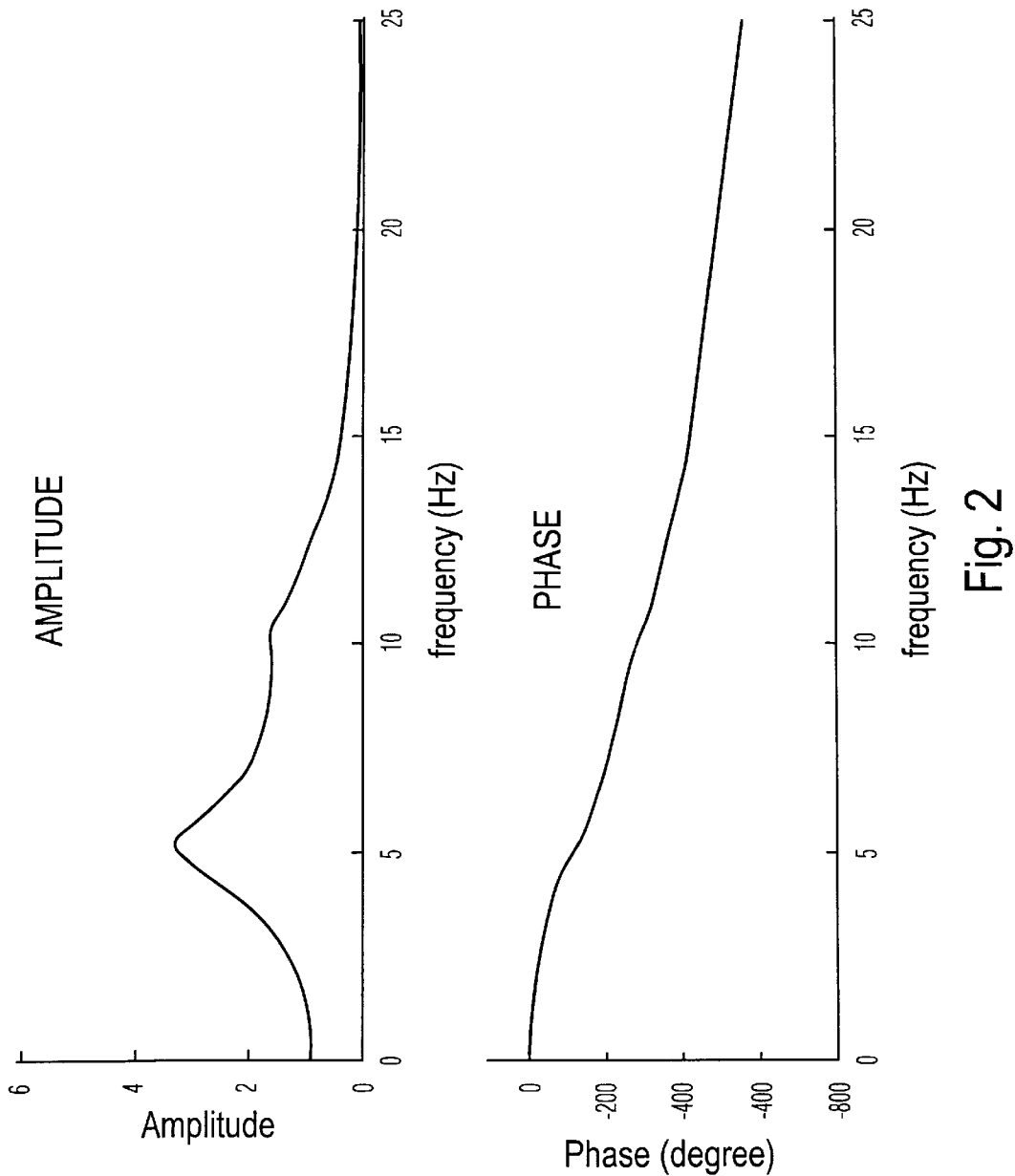
FIG. 2 is an exemplary illustration of an average transfer function from a group of 10 subjects.
Figure 3:
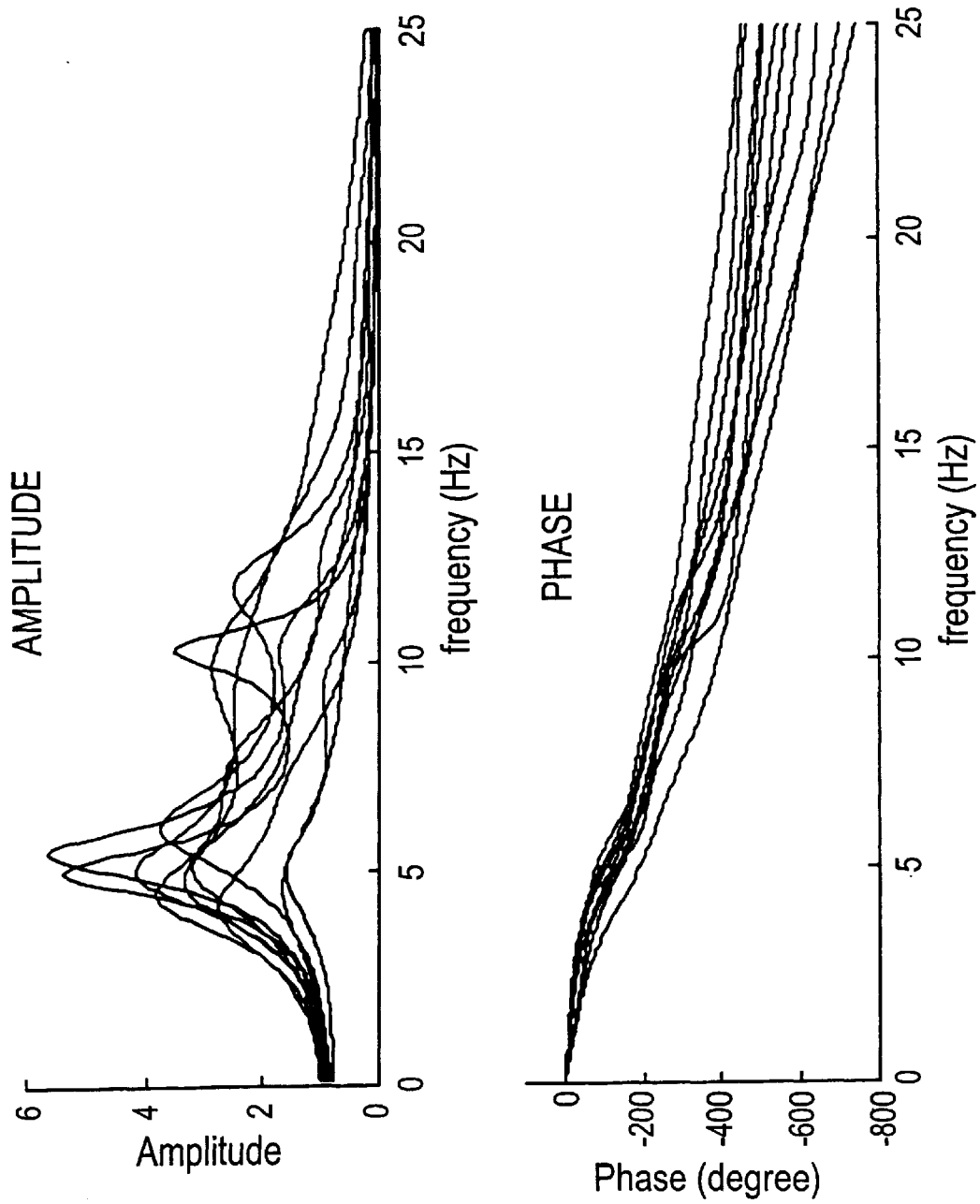
FIG. 3 shows individual transfer functions for the 10 subjects used to form the average transfer function illustrated in FIG. 2.

The linear model is formulated by first assuming a descriptive model that describes the physical components of the system. As can be seen from the average and individual transfer functions in FIGS. 2 and 3, a typical aortic to radial transfer function is composed of a number of resonances corresponding to the wave propagation times in the blood vessels from the aorta to the measurement point. The number of peaks is an indication of the number of resonant segments in the system. As shown in FIGS. 2 and 3, two and, in some cases, three resonances dominate the transfer functions.

A transmission line model consisting of resistance (R), compliance (C), and inertance (L) elements produces this type of behavior. In a compliant tube, resistance, compliance and inertance are related to the mechanical properties of the blood and wall tissue by the relations (see, Strano, Joseph J., Walter Welkowitz, and Sylvan Fich, "Measurement and Utilization of in vivo Blood Pressure Transfer Functions of Dog and Chicken Aortas," IEEE Trans. Biomedical Engineering, Vol. BME-19, No. 4, July, 1972, p. 269, incorporated by reference in its entirety):

$$\overline{R_i} = \frac{\overline{l_i}\kappa_o}{\overline{r_i^4}} \quad (2)$$

$$\overline{C_i} = \frac{2\overline{A_i}\overline{r_i}\overline{L_i}}{\overline{E_i}\overline{h_i}} \quad (3)$$

$$\overline{L_i} = \frac{\rho\overline{l_i}}{\overline{A_i}} \quad (4)$$

where:

$\overline{A_i}$=average cross sectional area of the ith vessel segment, $\overline{E_i}$=modulus of elasticity of the ith vessel segment, $\overline{h_i}$=average wall thickness of the ith vessel segment, $\overline{l_i}$=length of the ith vessel segment, $\overline{r_i}$=average radius of the ith vessel segment, $\rho$=density of blood, and $\kappa_o$=effective viscosity of the blood and wall tissue.

A fourth relationship of importance in lumped parameter analysis of cardiovascular mechanics is the velocity of wave propagation. Unlike wave propagation in solids or incompressible fluids in rigid conduits where the wave velocity is governed by the properties of the medium, the velocity of wave propagation (c) in a compliant blood vessel is governed by the mechanical properties of the vessel wall. This dependence was first described by Moens and Korteweg in 1878 and has a number of forms:

$$c = \sqrt{\frac{Eh}{2\rho r}} = \frac{l}{\Delta t} = f\lambda = \frac{\omega\lambda}{2\pi} \quad (5)$$

where:

$\Delta t$=the time for the pulse to travel a distance, l, in the tube, f=the natural frequency of the tube, $\omega$=the angular natural frequency of the wave, and $\lambda$=the wavelength of the tube that is dependent upon the termination of the tube.

The significance of these relations is explained below.

Figure 4:
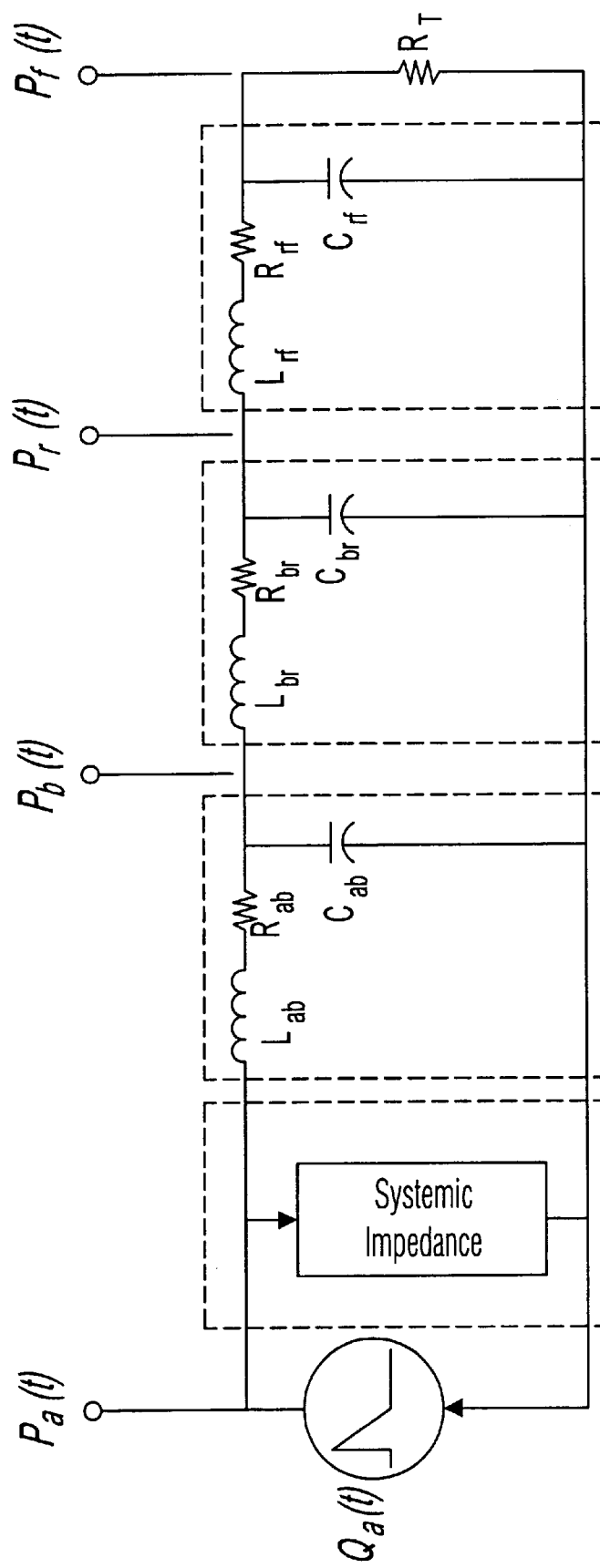
FIG. 4 illustrates an analog electrical circuit in which the analogues of the vessel properties are combined.

The analogues of the vessel properties can be combined into an analog electrical circuit as shown in FIG. 4. Therefore, FIG. 4 serves as a linear model of wave propagation in the cardiovascular system. Each element and resistance-inductance-capacitance (RLC) loop of the circuit is correlated with a corresponding part of the aorta-brachial-radial-finger blood flow system. The first loop of the circuit composed of inductance $L_{ab}$, resistance $R_{ab}$, and capacitance $C_{ab}$ corresponds to the aorta-to-brachial blood vessels. The inductance $L_{ab}$ is analogous to the inertia of the volume of blood traversing these vessels; the resistance $R_{ab}$ is analogous to the viscous-viscoelastic resistance of the vessels and blood, the capacitance $C_{ab}$ is analogous to the mechanical compliance of the vessels, and the current through the RL elements is analogous to the blood flow volumetric rate.

The other RLC loops represent the brachial-to-radial blood vessels and the radial-to-finger blood vessels. The resistance $R_T$ represents the terminal resistance of the system of blood vessels. Usually, the resistances $R_{ab}$, $R_{br}$ and $R_{rf}$ are individually and collectively much smaller than $R_T$. The analogous impedance of the rest of the body is represented by the element labeled Systemic Impedance. The voltage $P_a$ is analogous to the blood pressure in the aorta. This pressure is applied both to the systemic system and to the vessels of the arm. The voltage $P_f$ is analogous to the blood pressure measured at the fingertip. The voltage across $C_{ab}$ is analogous to the brachial blood pressure, $P_b$, the voltage across $C_{br}$ is analogous to the blood pressure measured at the wrist, $P_r$, and the voltage across $C_{rf}$ (which is identical to $P_f$) is analogous to the pressure measured at the finger.

Figure 5:
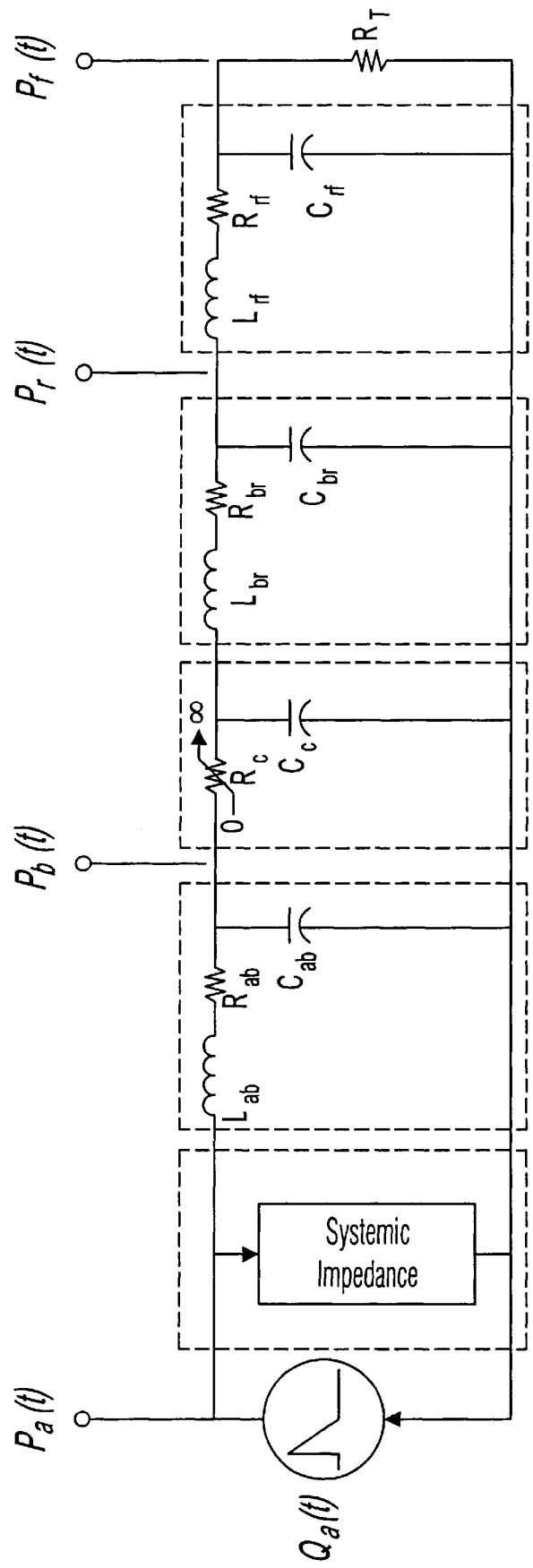
FIG. 5 illustrates an analog electrical circuit that includes an RC loop that represents a blood pressure cuff applied to constrict the brachial vessels of the arm.

FIG. 5 also is a linear model of wave propagation in the cardiovascular system. However, FIG. 5 also models the effect of a blood pressure cuff. FIG. 5 includes an RC loop that represents a blood pressure cuff that can be applied to constrict the brachial vessels and thereby prevent the flow of blood to the extremities of the arm. When the cuff is fully inflated, the resistance $R_c$ is effectively infinite preventing blood flow to the downstream components of the circuit. When the cuff pressure is released, the resistance is effectively zero. The capacitance $C_c$ represents the mechanical compliance of the cuff and its associated tubing; when the cuff pressure is released or is very low, the mechanical compliance is assumed to be very large ($1/C_c \approx 0$) such that it does not affect the blood flow although the circuit does not represent this explicitly.

Figure 6:
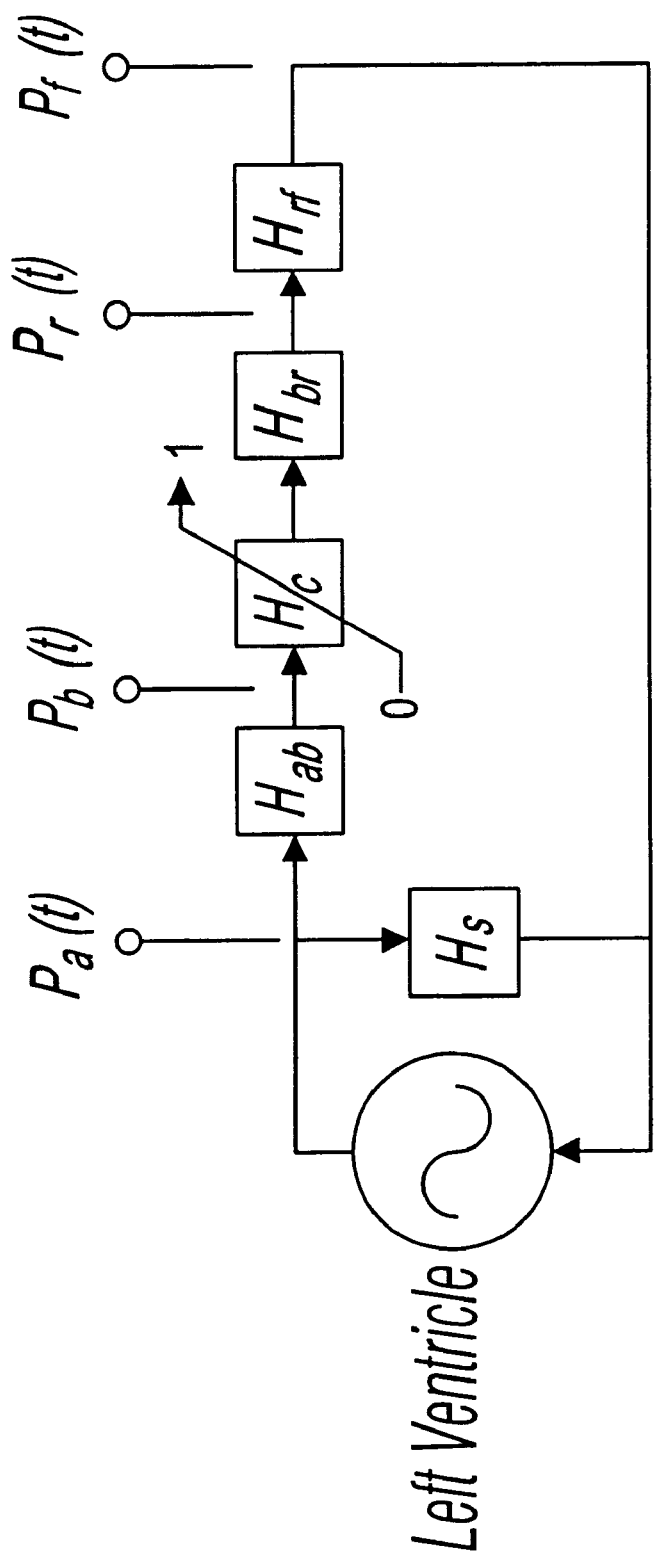
FIG. 6 illustrates a transfer function model of an arm's cardiovascular system with a blood pressure.

FIG. 6 shows a third linear model for describing the wave propagation in the cardiovascular system. As in the model of FIG. 5, the model incorporates elements analogous to a blood pressure cuff. In the model of FIG. 6, the pressure at any point in the cardiovascular system can be computed by multiplying the input pressure by the product of the transfer functions. The elements analogous to a blood pressure cuff are incorporated in anticipation of the model's application to a subject. The transfer functions $H_s$, $H_{ab}$, $H_c$, $H_{br}$ and $H_{rf}$ can be expressed in terms of the components of the electrical circuit shown in FIG. 4.

The aorta-to-finger transfer function $H_{af}(f)$, not shown in FIG. 6, can be derived from the electrical circuit in the frequency domain that relates the pressure across the terminal resistance, $R_T$, of the finger to that at the aorta:

$$P_f(f) = H_{af}(f) P_a(f) \quad (6)$$

The transfer function $h_{af}(f)$ is given by:

$$H_{af}(f) = \frac{G}{(2j\pi f)^6 + A(2j\pi f)^5 + B(2j\pi f)^4 + C(2j\pi f)^3 + D(2j\pi f)^2 + E(2j\pi f) + F} \quad (7)$$

where f is frequency in Hz, $j=\sqrt{-1}$, and A, B, C, D, E, F, and G are combinations of the electric circuit parameters. The frequency domain variable $(2j\pi f)$ is equivalent to a time derivative in the time domain. A, B, C, D, E, F and G can also be expressed in an alternative form that involves only the resonance frequencies $\omega_{ab}$, $\omega_{br}$, and $\omega_{rf}$ (where $\omega = 2\pi f$ is the angular frequency expressed in radians/sec, etc.) and damping coefficients $\zeta_{ab}$, $\zeta_{br}$, and $\zeta_{rf}$ of the three RLC loops of the circuit. These formulations are listed below for the case when $R_{ab}$, $R_{br}$, and $R_{rf}$ are negligibly small.

$$A = \frac{1}{R_T C_{rf}} \quad (8a)$$

$$B = \frac{1}{L_{ab}C_{ab}} + \frac{1}{L_{br}C_{br}} + \frac{1}{L_{rf}C_{rf}} + \frac{1}{L_{br}C_{ab}} + \frac{1}{L_{rf}C_{br}} \quad (8b)$$

$$C = \frac{1}{R_T C_{rf}}\left(\frac{1}{L_{ab}C_{ab}} + \frac{1}{L_{br}C_{br}} + \frac{1}{L_{br}C_{ab}} + \frac{1}{L_{rf}C_{br}}\right) \quad (8c)$$

$$D = \frac{1}{L_{ab}C_{ab}}\left(\frac{1}{L_{br}C_{br}} + \frac{1}{L_{rf}C_{rf}} + \frac{1}{L_{rf}C_{br}}\right) + \frac{1}{L_{br}C_{ab}}\left(\frac{1}{L_{rf}C_{rf}} + \frac{1}{L_{rf}C_{br}}\right) + \frac{1}{L_{br}C_{br}} * \frac{1}{L_{rf}C_{rf}} \quad (8d)$$

$$E = \frac{1}{R_T C_{rf}}\left[\frac{1}{L_{ab}C_{ab}}\left(\frac{1}{L_{br}C_{br}} + \frac{1}{L_{rf}C_{br}}\right) + \frac{1}{L_{br}C_{ab}}\left(\frac{1}{L_{rf}C_{br}}\right)\right] \quad (8e)$$

$$F = G = \frac{1}{L_{ab}C_{ab}} * \frac{1}{L_{br}C_{br}} * \frac{1}{L_{rf}C_{rf}} \quad (8f)$$

These relations involve six distinct combinations of paired electrical circuit parameters, namely $L_{ab}C_{ab}$, $L_{br}C_{br}$, $L_{rf}C_{rf}$, $L_{br}C_{ab}$, $L_{rf}C_{br}$, and $R_T C_{rf}$.

Because each of the transfer functions are nominally equivalent to the RLC loop element groups, each transfer function can be represented by a second order transfer function having the form:

$$S(f) = \frac{\omega_o^2}{(2j\pi f)^2 + 2\zeta\omega_o(2j\pi f) + \omega_o^2} \quad (9)$$

where $\omega_0$ is the natural angular frequency and $\zeta$ is the effective damping of the transfer function section. This representation allows the aorta-to-finger transfer function, representing a subject's arm, to be described as a product of second order transfer functions for the three segments of the pulse propagation path, $S_{ab}(f)$, $S_{br}(f)$, and $S_{rf}(f)$, or:

$$H_{af}(f) = S_{ab}(f) * S_{br}(f) * S_{rf}(f) \quad (10)$$

Using the definition of the transfer functions given in Eq. 9, Eq. 10 can be restated in the form:

$$H_{af}(f) = \frac{\omega_{ab}^2 \omega_{br}^2 \omega_{rf}^2}{[(2j\pi f)^2 + 2\zeta_{ab}\omega_{ab}(2j\pi f) + \omega_{ab}^2]} \\ [(2j\pi f)^2 + 2\zeta_{br}\omega_{br}(2j\pi f) + \omega_{br}^2] \\ [(2j\pi f)^2 + 2\zeta_{rf}\omega_{rf}(2j\pi f) + \omega_{rf}^2] \quad (11a)$$

or:

$$H_{af}(f) = \frac{G}{(2j\pi f)^6 + A(2j\pi f)^5 + B(2j\pi f)^4 + C(2j\pi f)^3 + D(2j\pi f)^2 + E(2j\pi f) + F} \quad (11b)$$

which has a form identical to Eq. 7. The coefficients, however, are composed of the three resonance frequencies and three damping coefficients as:

$$A = 2(\zeta_{ab}\omega_{ab} + \zeta_{br}\omega_{br} + \zeta_{rf}\omega_{rf}) \quad (12a)$$

$$B = \omega_{ab}^2 + \omega_{br}^2 + \omega_{rf}^2 + 4(\zeta_{ab}\zeta_{br}\omega_{ab}\omega_{br} + \zeta_{ab}\zeta_{rf}\omega_{ab}\omega_{rf} + \zeta_{br}\zeta_{rf}\omega_{br}\omega_{rf}) \quad (12b)$$

$$C = 2\zeta_{ab}\omega_{ab}(\omega_{br}^2 + \omega_{rf}^2) + 2\zeta_{br}\omega_{br}(\omega_{ab}^2 + \omega_{rf}^2) + 2\zeta_{rf}\omega_{rf}(\omega_{ab}^2 + \omega_{br}^2) + 8\zeta_{ab}\zeta_{br}\zeta_{rf}\omega_{ab}\omega_{br}\omega_{rf} \quad (12c)$$

$$D = \omega_{ab}^2(\omega_{br}^2 + \omega_{rf}^2) + \omega_{br}^2\omega_{rf}^2 + 4\zeta_{ab}\omega_{ab}(\zeta_{br}\omega_{br}\omega_{rf}^2 + \zeta_{rf}\omega_{rf}\omega_{br}^2) + 4\zeta_{br}\zeta_{rf}\omega_{br}\omega_{rf}\omega_{ab}^2 \quad (12d)$$

$$E = 2\zeta_{ab}\omega_{ab}(\omega_{br}^2\omega_{rf}^2) + 2\zeta_{br}\omega_{br}(\omega_{ab}^2\omega_{rf}^2) + 2\zeta_{rf}\omega_{rf}(\omega_{ab}^2\omega_{br}^2) \quad (12e)$$

$$F = G = \omega_{ab}^2\omega_{br}^2\omega_{rf}^2 \quad (12f)$$

Figure 7:
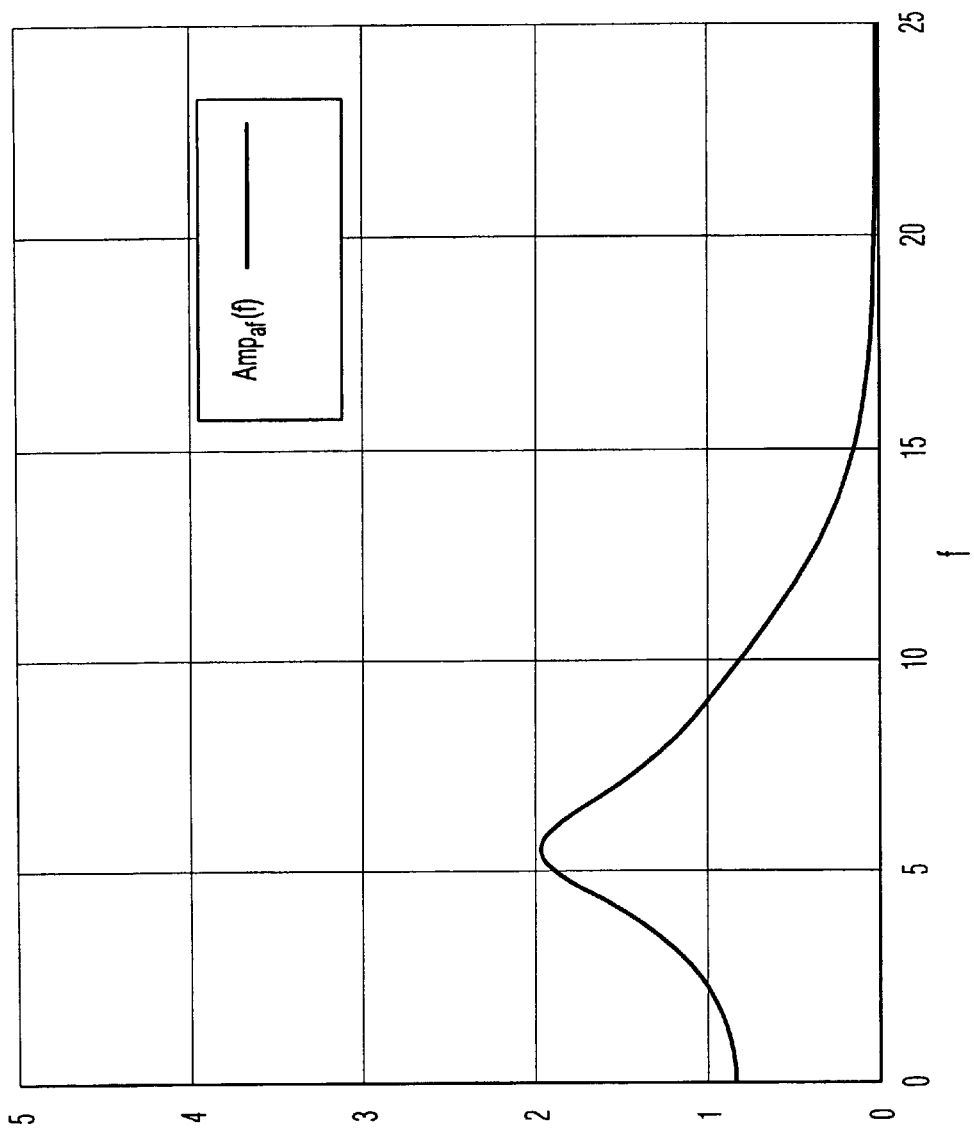
FIG. 7 illustrates an aortic-to-finger transfer function magnitude for high damping.

The magnitude plot of the transfer function is shown in FIG. 7. This figure shows the aorta-to-finger transfer function $H_{af}(f)$ with the resonance frequencies set to $f_{ab}$=5.8 Hz, $f_{br}$=11.0 Hz, $f_{rf}$=16.0 Hz, and with damping coefficients of $\zeta_{ab}$=0.3, $\zeta_{br}$=0.3, and $\zeta_{rf}$=0.4. This $H_{af}(f)$ corresponds to a case in which the resistance, $R_T$, is low, thus producing increased damping.

Figure 8:
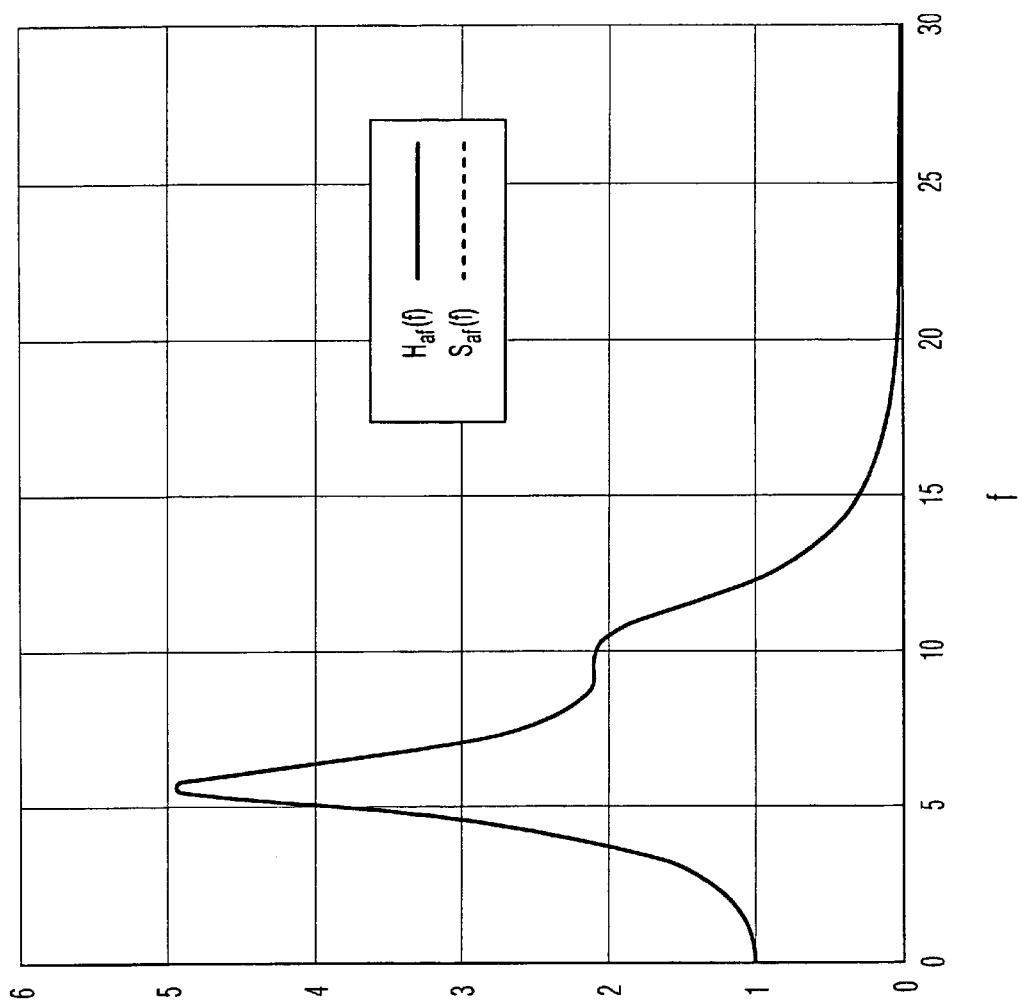
FIG. 8 illustrates a magnitude of an aortic-to-finger transfer function with low damping.

FIG. 8 shows a case of normal peripheral resistance when $f_{ab}$=5.8 Hz, $f_{br}$=11.0 Hz, $f_{rf}$=16.0 Hz, $\zeta_{ab}$=0.15, $\zeta_{br}$=0.15, and $\zeta_{rf}$=0.3. The transfer function $H_{af}(f)$ now shows a pronounced resonance at 5.9 Hz and a smaller resonance at 11.0 Hz; the resonance at 16.0 Hz is not evident. The transfer functions shown in FIGS. 7 and 8 are seen to be essentially identical to examples of empirically derived individual transfer functions shown in FIG. 3. It should also be noted that the second order representation, $S_{af}(f)$ is identical to $H_{af}(f)$. This is demonstrated in FIG. 8 by the two curves lying on top of each other.

As can be seen by comparing the alternative forms of these relations, the circuit parameter $1/R_T C_{rf}$ corresponds to the sum all the damping constants, $2\zeta\omega_0$. Furthermore, the parameters $1/LC$ correspond to the square of the natural frequencies, $\omega_0$. The other coefficients, however, are not equivalent on a term-by-term basis due to the cross coupling of the three RLC sections and the effect of the terminal resistance on the effective damping coefficient of each section. The effect of cross coupling is best understood by reviewing the transfer functions that would be measured between each of the measurement points.

Radial-to-Finger Transfer Function

The measured transfer function $H_{rf}(f)$ between the radial and finger measurement locations is given by Eqs. 13a and 13b:

$$H_{rf}(f) = \frac{\omega_{rf}^2}{(2j\pi f)^2 + 2(\zeta_{ab}\omega_{ab} + \zeta_{br}\omega_{br} + \zeta_{rf}\omega_{rf})(2j\pi f) + \omega_{rf}^2} \quad (13a)$$

or:

$$H_{rf}(f) = \frac{\omega_{rf}^2}{(2j\pi f)^2 + Z_1(2j\pi f) + \omega_{rf}^2} \quad (13b)$$

where:

$$Z_1 = A = 2(\zeta_{ab}\omega_{ab} + \zeta_{br}\omega_{br} + \zeta_{rf}\omega_{rf}) \quad (14)$$

Figure 9:
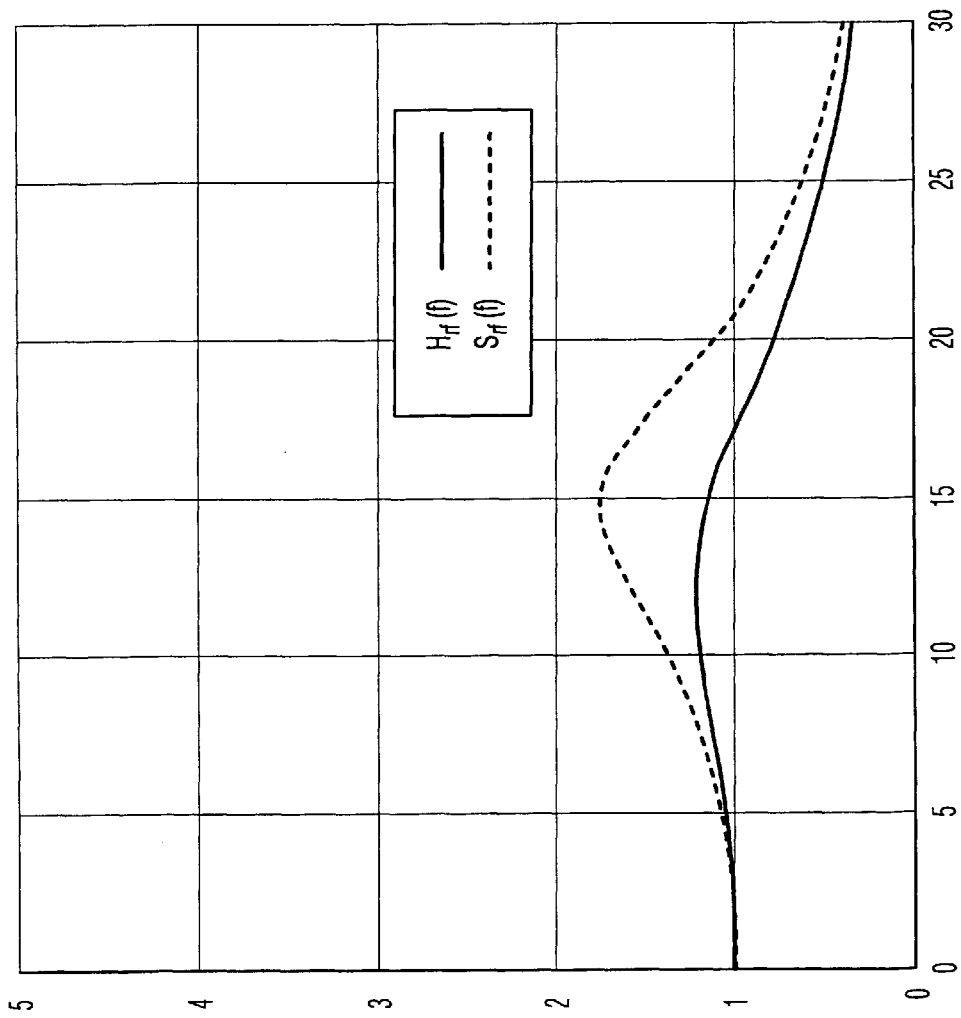
FIG. 9 illustrates a radial-to-finger transfer function magnitude in a low damping case (solid line) and a second order transfer function of the radial-to-finger arterial segment.

The magnitude plot of this transfer function is shown in FIG. 9 for the case when $f_{br}$=11.0 Hz, $f_{rf}$=16 Hz, $\zeta_{br}$=0.15, and $\zeta_{rf}$=0.3. As shown in FIG. 9 and Eq. 13b, the radial-to-finger transfer function $H_{rf}(f)$ is that of a simple second order system. This transfer function is directly computed from simultaneous measurements of the radial and finger blood pressure waveforms. However, it should be noted that the damping constant is the sum of all the damping constants in the systems and is slightly different from that for $S_{rf}(f)$.

Brachial-to-Radial Transfer Function

Similarly, the transfer function $H_{br}(f)$ for the system between the brachial and radial measurement locations can be derived from the electric circuit shown in FIG. 4 in terms of natural frequencies and damping coefficients. It is given by Eq. 15:

$$H_{br}(f) = \frac{\omega_{br}^2(2j\pi f)^2 + Z_3(2j\pi f) + \omega_{br}^2\omega_{rf}^2}{(2j\pi f)^4 + Z_1(2j\pi f)^3 + Z_2(2j\pi f)^2 + Z_3(2j\pi f) + \omega_{br}^2\omega_{rf}^2} \quad (15)$$

where:

$$Z_2 = \omega_{br}^2 + \omega_{rf}^2 + 4\zeta_{ab}\omega_{ab}(\zeta_{br}\omega_{br} + \zeta_{rf}\omega_{rf}) + 4\zeta_{br}\omega_{br}\zeta_{rf}\omega_{rf} \quad (16)$$

$$Z_3 = Z_1[\omega_{br}^2 + 4(\zeta_{ab}\zeta_{br}\omega_{ab}\omega_{br} + \zeta_{ab}\zeta_{rf}\omega_{ab}\omega_{rf} + \zeta_{br}\zeta_{rf}\omega_{br}\omega_{rf})] \quad (17)$$

Figure 10:
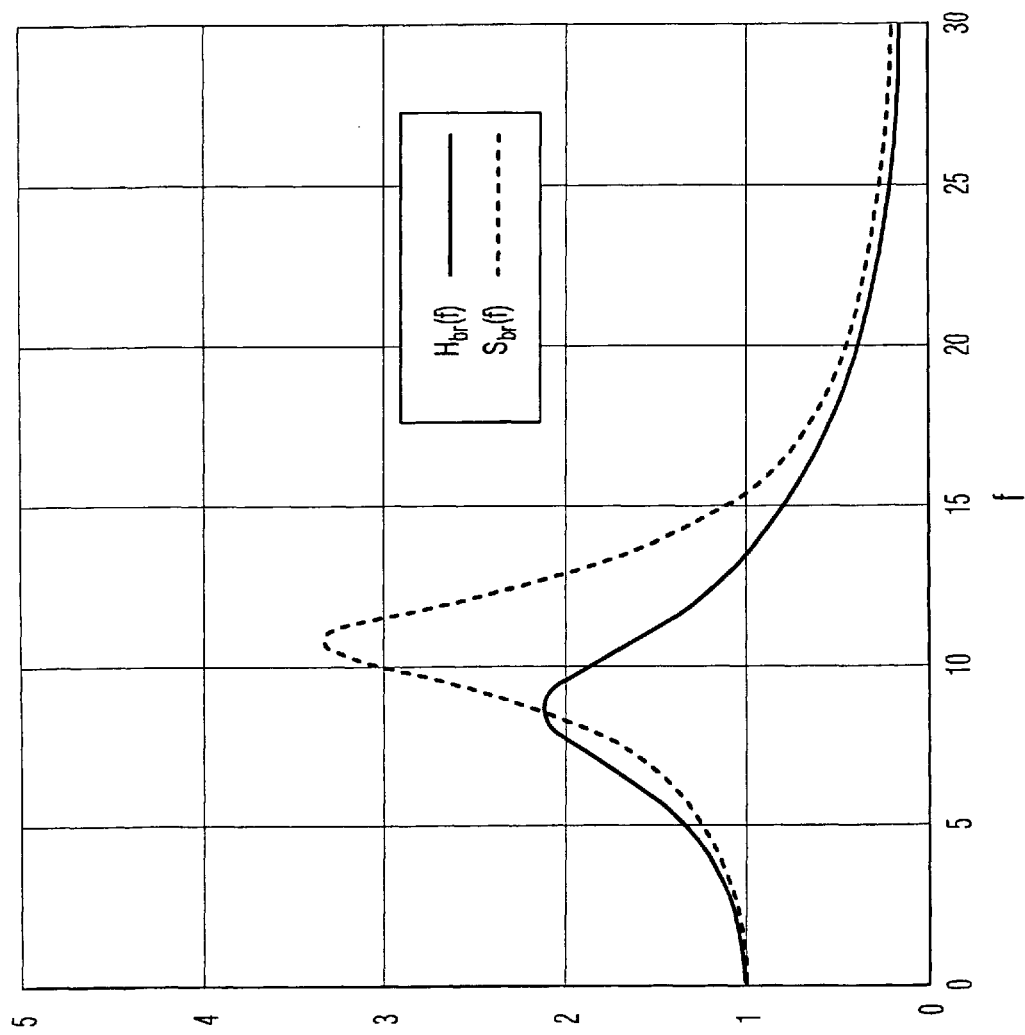
FIG. 10 illustrates a brachial-to-radial transfer function magnitude in a low damping case (solid line) and a second order transfer function of the same brachial-to-radial arterial segment.

The magnitude plot of this transfer function is shown in FIG. 10 for the case when $f_{br}$=11.0 Hz, $f_{rf}$=16 Hz, $\zeta_{br}$=0.15, and $\zeta_{rf}$=0.3. This transfer function can be computed for a subject if simultaneous recordings of the brachial and radial blood pressure waveforms are measured. As seen in Eq. 15, the brachial-to-radial transfer function is a function of both the brachial and radial segment parameters as well as the total damping constant, $Z_1$. Although difficult to see, FIG. 10 shows that the magnitude of $H_{br}$ does not fall off in the smooth exponential manner as the second order radial-to-finger transfer function, $S_{br}$. This behavior is due to the influence of the damping in the other cardiovascular system segments and that $H_{br}$ is computed using a second order system divided by a fourth order system.

Aortic-to-Brachial Transfer Function

The measured transfer function $H_{ab}(f)$ is given:

$$H_{ab,Z_C=0}(f) = \frac{P_b}{P_a} = \frac{\omega_{ab}^2[(2j\pi f)^4 + Z_1(2j\pi f)^3 + Z_2(2j\pi f)^2 + Z_3(2j\pi f) + \omega_{br}^2\omega_{rf}^2]}{(2j\pi f)^6 + A(2j\pi f)^5 + B(2j\pi f)^4 + C(2j\pi f)^3 + D(2j\pi f)^2 + E(2j\pi f) + F} \quad (18)$$

Figure 11:
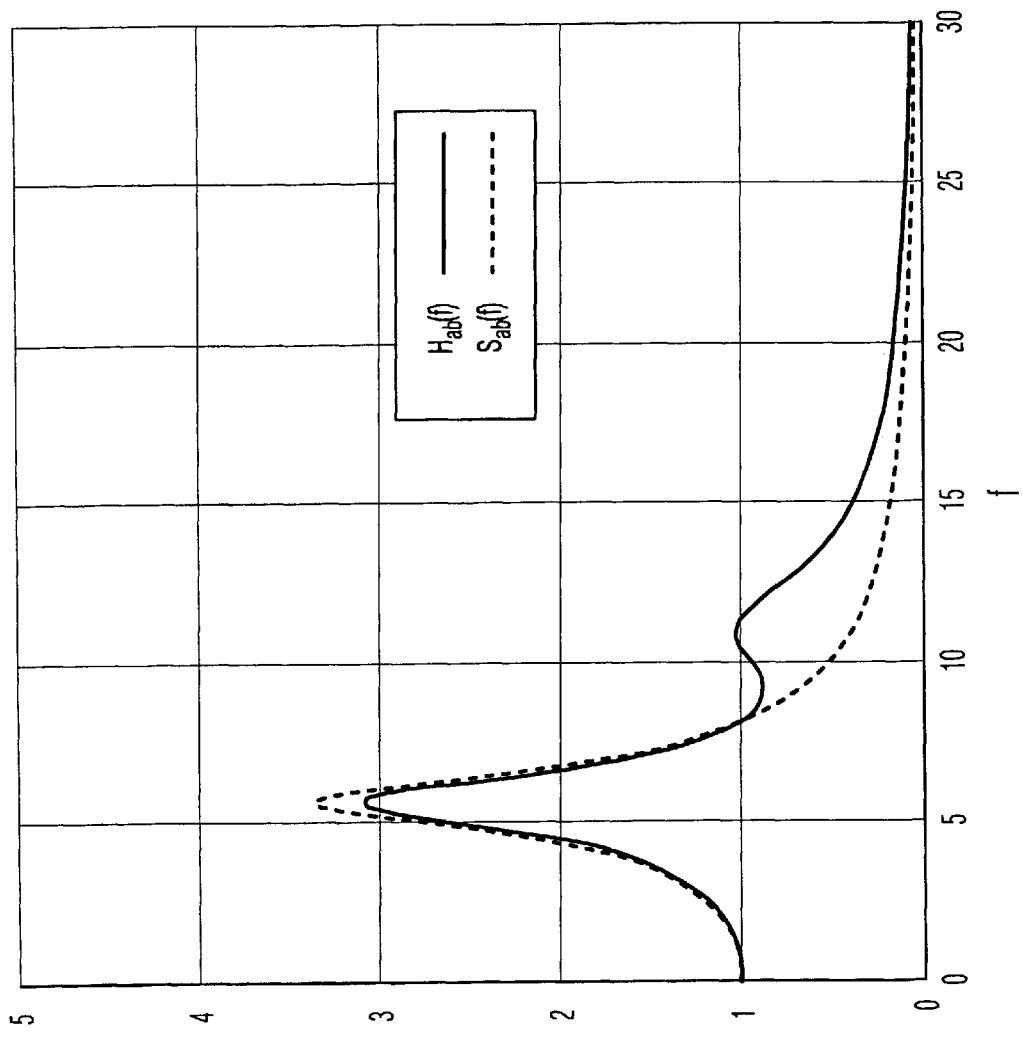
FIG. 11 illustrates an aortic-to-brachial transfer function magnitude for a low damping case (solid line) and a second order transfer function of the same aortic-to-brachial arterial segment.

The magnitude plot of $H_{ab}(f)$ is shown in FIG. 11. The influence of the damping and natural frequencies of the other segments of the arm and its computation using a fourth and sixth order equations is seen in the second peak in the transfer function. The second order equation $S_{ab}(f)$ is shown for comparison.

Figure 12:
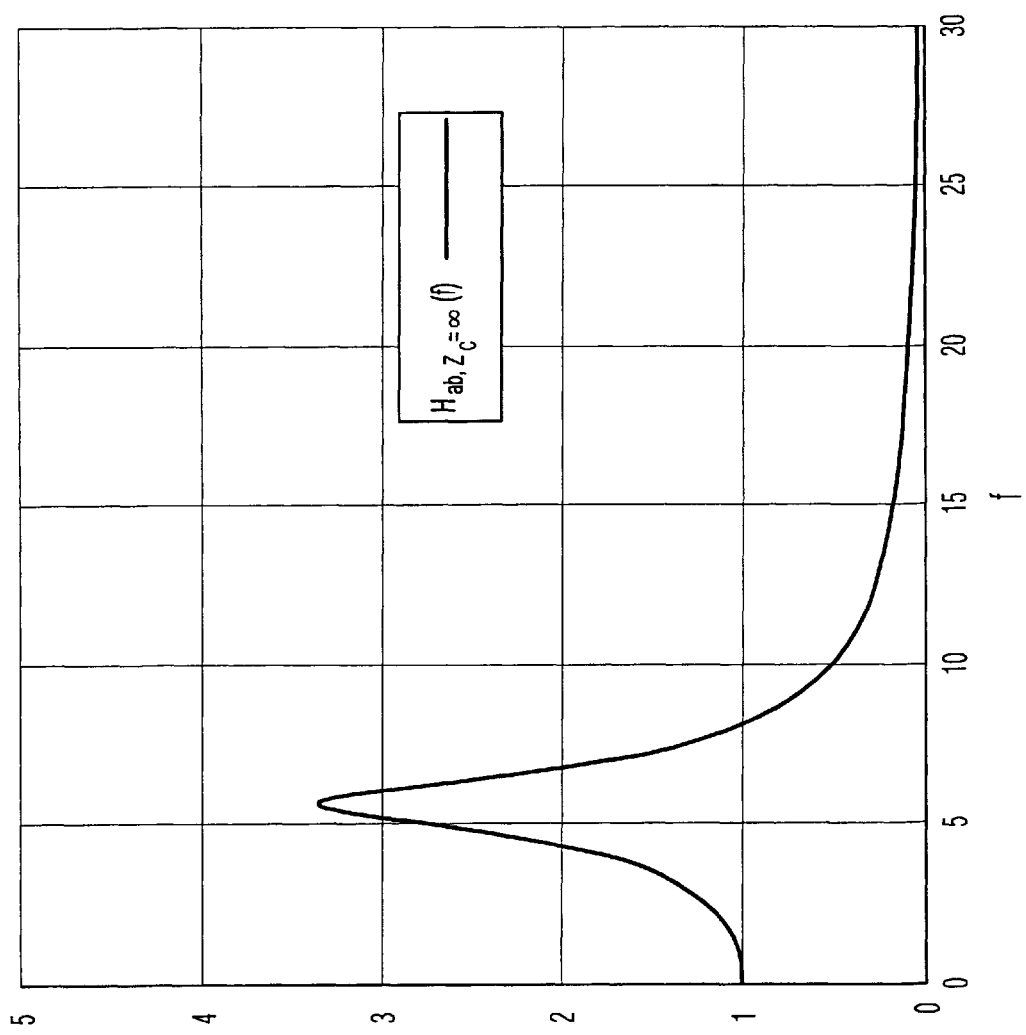
FIG. 12 illustrates an aortic-to-brachial transfer function magnitude with cuff inflated in a low damping case.

However, this transfer function cannot be directly computed because the aortic pressure waveform $P_a(f)$ cannot be measured in a given subject. If the brachial pressure is measured with the occlusion cuff fully inflated, as shown in FIG. 5, the vessel between the aorta and the measurement location is effectively terminated with an infinitely large impedance (R=∞, $H_C(f)$=0), which corresponds to a "closed end" acoustical transmission line. The magnitude of the aortic-to-brachial circuit transfer function for this case is shown in FIG. 12. The transfer function for this circuit is:

$$H_{ab,Z_C=\infty}(f) = S_{ab}(f) = \frac{P_b(f)}{P_a(f)} = \frac{\omega_{ab}^2}{(2j\pi f)^2 + 2\zeta_{ab}\omega_{ab}(2j\pi f) + \omega_{ab}^2} \quad (19)$$

As seen in Eq. 19 and FIG. 12, the effects of the downstream resonances are removed leaving only the aortic-to-brachial segment to influence the resonance frequency and damping.

The resonance frequency $f_{ab}$ of the aorta-to-brachial segment of vessels, or the equivalent parameter $L_{ab}C_{ab}$ of the circuit, can be determined by measuring the wave propagation time $\Delta t_{ab}$ between the ECG R-wave and the time at which the pressure begins to increase at the brachial location. Thus, the natural frequency is given directly by $f_{ab} = c_{ab}/\lambda_{ab}$, where $c_{ab}$ is the wave velocity and $\lambda_{ab}$ is the wavelength of the pressure wave propagating from the aorta to the cuff location. Since $c_{ab}=l_{ab}/\Delta t_{ab}$, where $l_{ab}$ is the length of the vessel, and $\lambda_{ab}=4l_{ab}$ for a closed end boundary condition, the natural frequency is given by $\frac{1}{4}\Delta t_{ab}$. When the cuff is released, the aorta-to-brachial segment of vessel is coupled to the rest of the vessels in the arm; the wave propagation time is the same as when the cuff is inflated, but the terminal impedance of the vessels in the segment, while still large, is not effectively infinite. Thus, the effective wavelength of the pressure wave propagating from the aorta to the cuff location is slightly less than $4l_{ab}$, which is the result of the coupling. The difference between the coupled and uncoupled natural frequencies is negligible and, as a result, the natural frequency, $\omega_{ab}$, is essentially the same.

As a result, the only variable that cannot be measured for a given subject is the damping coefficient, $\zeta_{ab}$, for the aortic-to-brachial segment of the pulse propagation path. Therefore, several methods for indirectly measuring the damping coefficient are explained below.

Also, germane to the linear models is another form for the aortic-to-brachial transfer function $H_{ab}(f)$. Remembering that the characteristic equations of the measured aortic-to-finger transfer function is equivalent to that derived from the second order representations of the systems, Eq. 18 can also be expressed as:

$$H_{ab,Z_C=0}(f) = \frac{\omega_{ab}^2[(2j\pi f)^4 + Z_1(2j\pi f)^3 + Z_2(2j\pi f)^2 + Z_3(2j\pi f) + \omega_{br}^2\omega_{rf}^2]}{[(2j\pi f)^2 + 2\zeta_{ab}\omega_{ab}(2j\pi f) + \omega_{ab}^2]} \\ [(2j\pi f)^2 + 2\zeta_{br}\omega_{br}(2j\pi f) + \omega_{br}^2] \\ [(2j\pi f)^2 + 2\zeta_{rf}\omega_{rf}(2j\pi f) + \omega_{rf}^2]$$ (20)

or $$H_{ab,Z_C=0}(f) = \frac{S_{ab}(f)S_{br}(f)S_{rf}(f)}{H_{br}(f)H_{rf}(f)}$$ (21)

Radial-to-Aortic Transfer Function

Given these relationships, a reverse transfer function can be derived that relates the pressure at the aorta from that at any intermediate point in the system. For pressures measured at the radial artery, the aortic pressure can be determined using one of several forms of the reverse transfer function from the radial-to-aortic transfer function:

$$H_{ra}(f) = \frac{1}{H_{ab}(f)H_{br}(f)} = H_{ba}(f) * H_{rb}(f)$$ (22a)

$$H_{ra}(f) = \frac{(2j\pi f)^6 + A(2j\pi f)^5 + B(2j\pi f)^4 + C(2j\pi f)^3 + D(2j\pi f)^2 + E(2j\pi f) + F}{\omega_{ab}^2\omega_{br}^2(2j\pi f)^2 + Z_3\omega_{ab}^2(2j\pi f) + F}$$ (22b)

$$H_{ra}(f) = \frac{[(2j\pi f)^2 + 2\zeta_{ab}\omega_{ab}(2j\pi f) + \omega_{ab}^2]}{\omega_{ab}^2\omega_{br}^2[(2j\pi f)^2 + 2(\zeta_{ab}\omega_{ab} + \zeta_{br}\omega_{br} + \zeta_{rf}\omega_{rf})(2j\pi f) + \omega_{rf}^2]}$$ (22c)

$$H_{ra}(f) = \frac{1}{S_{ab}(f)} * \frac{1}{S_{br}(f)} * \frac{1}{S_{rf}(f)} * \frac{\omega_{rf}^2}{[(2j\pi f)^2 + 2(\zeta_{ab}\omega_{ab} + \zeta_{br}\omega_{br} + \zeta_{rf}\omega_{rf})(2j\pi f) + \omega_{rf}^2]}$$ (22d)

$$H_{ra}(f) = \frac{1}{S_{ab}(f)} * \frac{1}{S_{br}(f)} * \frac{1}{S_{rf}(f)} * H_{rf}(f)$$ (22e)

Figure 13:
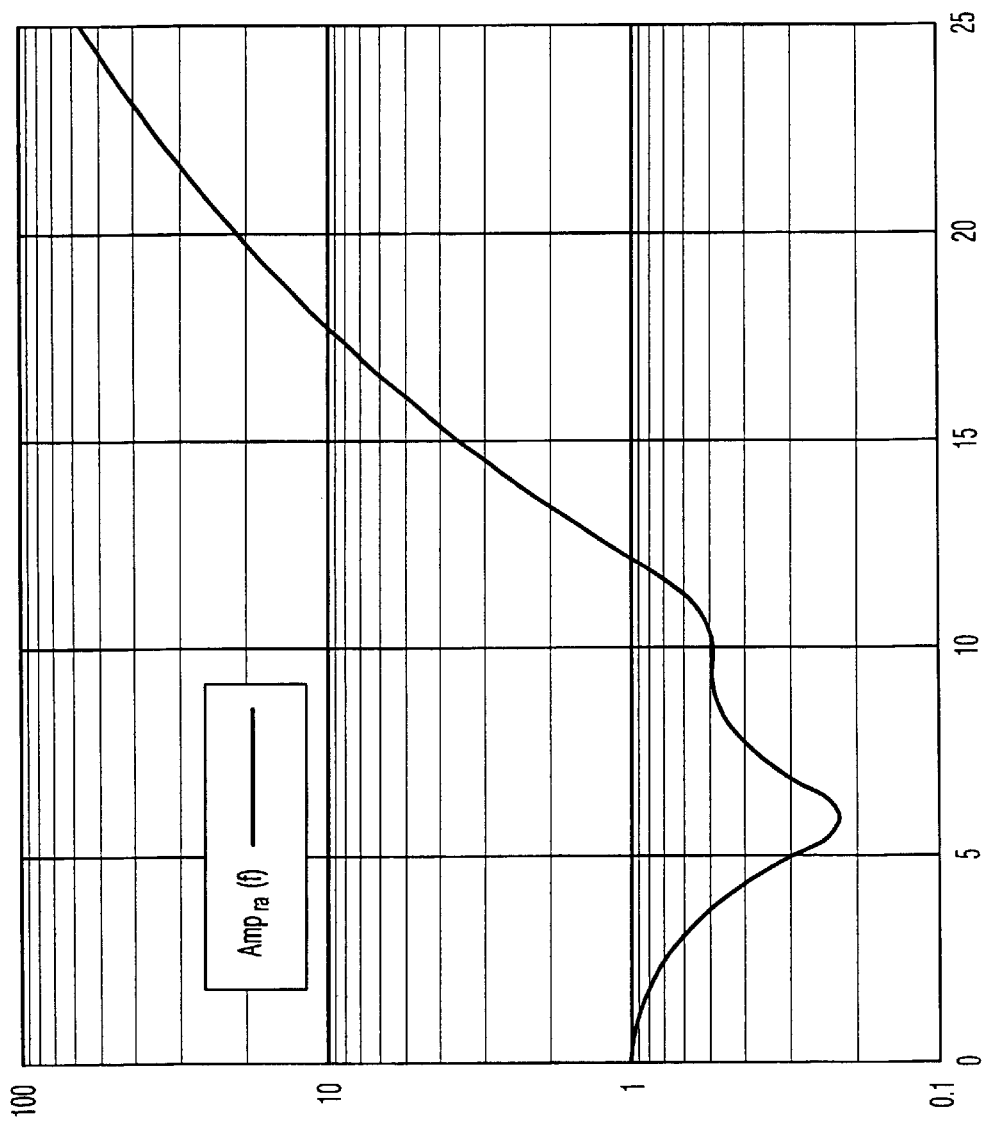
FIG. 13 illustrates a radial-to-aorta transfer function for a low damping case.

The magnitude plot of the reverse radial to aortic transfer function is shown in FIG. 13. As with the transfer functions of the individual segments, the aortic-to-brachial transfer function is dependent upon the parameters of the downstream segments. This is indicated by the second peak in the magnitude plot.

Constructing an Individualized Radial-to-Aortic Blood Pressure Reconstruction Model As explained earlier, the only parameter of the cardiovascular system that cannot be directly measured is the damping coefficient of the aortic-to-brachial segment. Therefore, the construction of an individualized transfer function is reduced to defining a device to find the damping of the aortic-to-brachial segment of the propagation path. This can be accomplished by a number of different methods.

A number of steps are common to all the methods. For example, all methods include measuring the propagation time of the pulse from the heart to the cuff with the brachial cuff inflated. Additionally, all methods measure the pressure waveforms at the brachial location, the radial location and the finger location with the brachial cuff inflated at a pressure well below diastolic pressure. All methods compute the transfer functions $H_{rb}(f)$ and $H_{fr}(f)$ or their time domain equivalent. All methods determine the natural frequencies $\omega_{br}$ and $\omega_{rf}$ from the reciprocal of the delay times (i.e., $1/\Delta t_{br}$ and $1/\Delta t_{rf}$) and determine the natural frequency, $\omega_{ab}$, of $H_{ba}(f)$ from the reciprocal of the delay time, $1/\Delta t_{ab}$, when the cuff is fully inflated. Finally, in all methods, the effective damping coefficients $\zeta_{br}$ and $\zeta_{rf}$ are determined from the ratio of the peak amplitudes to the low frequency limiting amplitude; the ratio is approximately $1/2\zeta$ for each peak.

In a first exemplary method for determining the damping of the aortic-to-brachial segment of the propagation path, the radial-to-aortic transfer function, $H_{ra}(f)$, is constructed using a measured reverse transfer function $H_{rb}(f)$ and an empirically derived standardized reverse transfer function, $E_{ba}(f_n)$ adjusted to the particular subject. The transfer function, $H_{rb}(f)$ is computed using the subject's brachial and radial waveforms.

Figure 14:
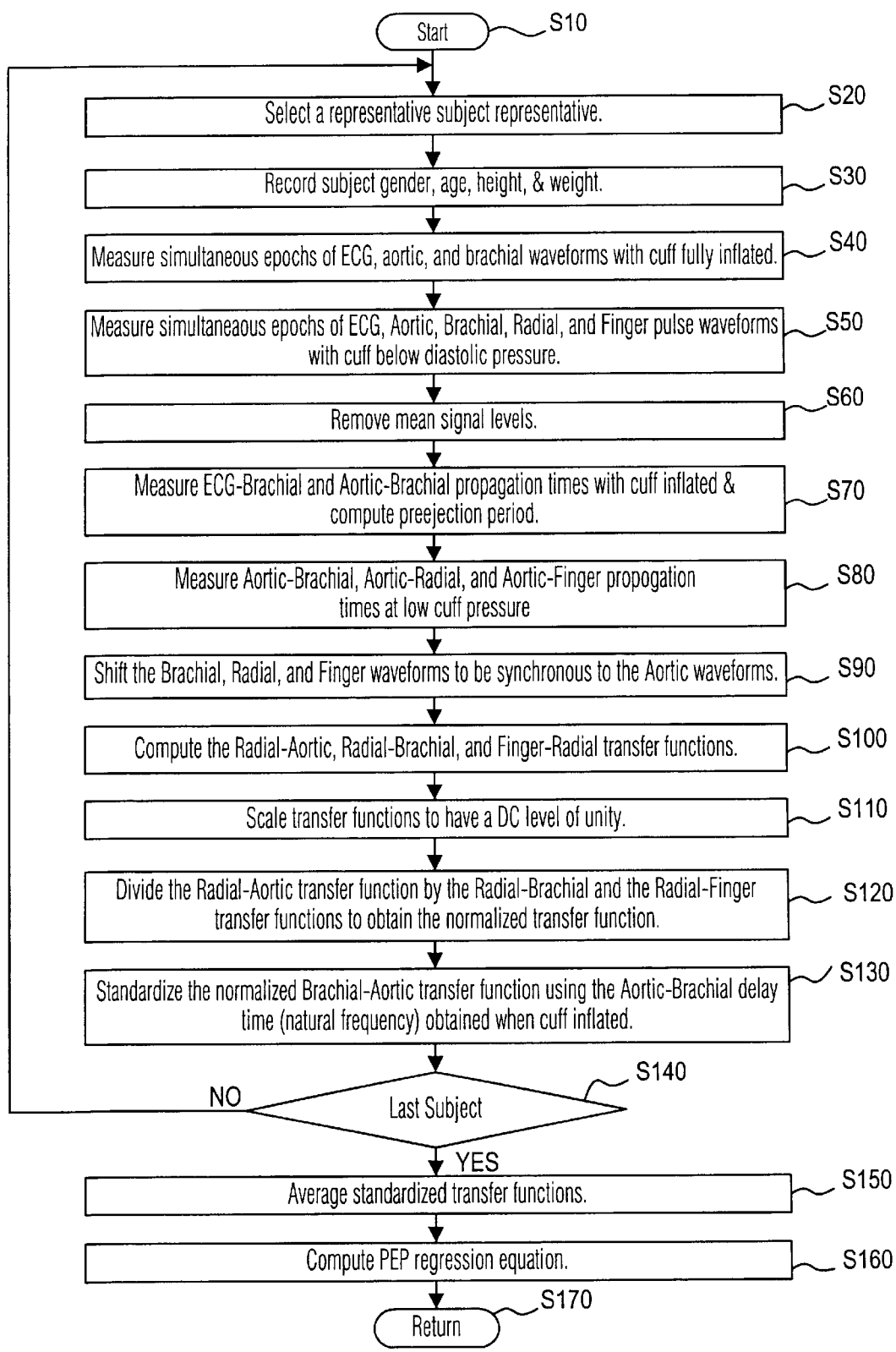
FIG. 14 illustrates a first exemplary method for developing a normalized universal reverse transfer function and universal aortic blood pressure reconstruction model.

The standardized transfer function, $E_{ba}(f_n)$, is obtained by the method shown in FIG. 14 using data collected in controlled studies of a large number of subjects. In these studies, aortic pressure measurements are obtained simultaneously with the brachial, radial, and finger waveforms. Such a method begins in step S10 and control proceeds to step S20. In step S20, a subject is selected as representative of the large number of subjects and control proceeds to step S30. In step S30, the subject's gender, age, height and weight is recorded and control proceeds to step S40. In step S40, simultaneous measurements of the epochs of ECG, aortic, and brachial waveforms with the blood pressure cuff fully inflated are taken. This measurement provides data for variables $e_{ecg}(t)$, $P_a(t)$ and $P_b(t)$. Subsequently, control proceeds to step S50.

In step S50, simultaneous measurement of epochs of ECG, aortic, brachial, radial and finger pulse waveforms is performed with the blood pressure cuff inflated below diastolic pressure to provide data for variables $e_{ecg}(t)$, $P_a(t)$, $P_b(t)$, $P_r(t)$ and $P_f(f)$ and control proceeds to step S60. In step S60, the mean signal levels are removed from the data provided in step S50 to provide values for $e_{ecg}(t)$, $p_a(t)$, $p_b(t)$ $p_r(t)$ and $p_f(f)$. Subsequently, in step S70, measurement of the ECG-Brachial propagation time, $\Delta t_{ecg-b}$, and aortic-brachial propagation time, $\Delta t_{ab}$, is performed with the blood pressure cuff fully inflated and the pre-ejection period is computed (i.e., the pre-ejection period is the passive delay time that occurs prior to the initiation of the blood pressure pulse in the aorta caused by the opening of the aortic valve $PEP=\Delta t_{ecg-b}-\Delta t_{ab}$. Control then proceeds to step S80, in which the propagation times through the aortic-brachial, $\Delta t_{ab}$, aortic-radial, $\Delta t_{ar}$, and aortic-finger $\Delta t_{af}$, segments with the cuff inflated at low cuff pressure are calculated. Next, in step S90, the brachial, radial and finger waveforms are shifted to be synchronous to the aortic waveforms providing data for variables $p_b(t-\Delta t_{ab})$, $p_r(t-\Delta t_{ar})$, $p_f(t-\Delta t_{af})$. Using those data, in step S100, computation of the radial-aortic transfer function, $H_{ra}(f)=P_a(f)/P_r(f)$, radial-brachial transfer function, $H_{rb}(f)=P_b(f)/P_r(f)$, and finger-radial, $H_{fr}(f)=P_r(f)/P_f(f)$, transfer function is performed. Control then proceeds to step S110, in which the transfer functions $H_{ra}(f)$, $H_{rb}(f)$ and $H_{fr}(f)$ are scaled to have a DC level of unity. Control then proceeds to step S120.

In step S120, the normalized transfer function $E_{ba-i}(f)$ for the ith subset is obtained by dividing the radial-aortic transfer function $H_{ra}(f)$ by the radial-brachial transfer function $H_{rb}(f)$ and the finger-radial transfer function $H_{fr}(f)$ and control proceeds to step S130. In step S130, the normalized brachial-aortic transfer function $E_{ba-i}(f)$ is standardized using the aortic-brachial delay time( i.e., the natural frequency, $f_{ab}$) obtained when the blood pressure cuff is fully inflated. Control then proceeds to step S140.

In step S140, it is determined whether all of the subjects in the subject pool have been selected in step S20 and analyzed in step S30–S130. If all subjects have been selected and analyzed, control proceeds to step S150 in which the average of the standardized transfer functions for all the subjects is calculated and proceeds to step S160. Alternatively, if a subject in the pool has not been selected and analyzed, control returns to step S20 to select and analyze the additional subject(s). In step S160, the pre-ejection period regression equation PEP=R($\Delta t_{ab}$, gender, age, height, weight, blood pressure (BP), heart rate (HR)) is computed and control proceeds to step S170. In step S170, control returns to the main method of constructing an individualized radial-to-aortic blood pressure reconstruction model.

Therefore, using the method of FIG. 14, the reverse transfer functions $H_{ra}(f)$, $H_{rb}(f)$, and $H_{fr}(f)$ are computed for each subject. The standardized transfer function is then computed using the relations:

$$h_{fa}(f) = H_{fr}(f) * H_{rb}(f) * H_{ba}(f) = h_{fr}(f) * H_{ra}(f). \quad (23)$$

From the standardized transfer function one can define a transfer function normalized for the terminal resistance and compliance as:

$$E_{ba}(f) = \frac{H_{ba}(f)}{H_{fr}(f)} = \frac{H_{ra}(f)_M}{H_{fr}(f) * H_{rb}(f)} \quad (24)$$

that is then normalized by the natural frequency $\omega_{ab}$ measured by the aortic-to-brachial propagation time with the cuff inflated to give the subject's standardized brachial-to-aortic transfer function:

$$E_{ba}(f_n) = E_{ba}(f/f_{ab}) = E_{ba}(4\Delta t_{ab} * f) \quad (25)$$

The standardized brachial-to-aortic transfer functions for a large representative population are then averaged to produce the universal standardized brachial-to-aortic transfer function.

Figure 15:
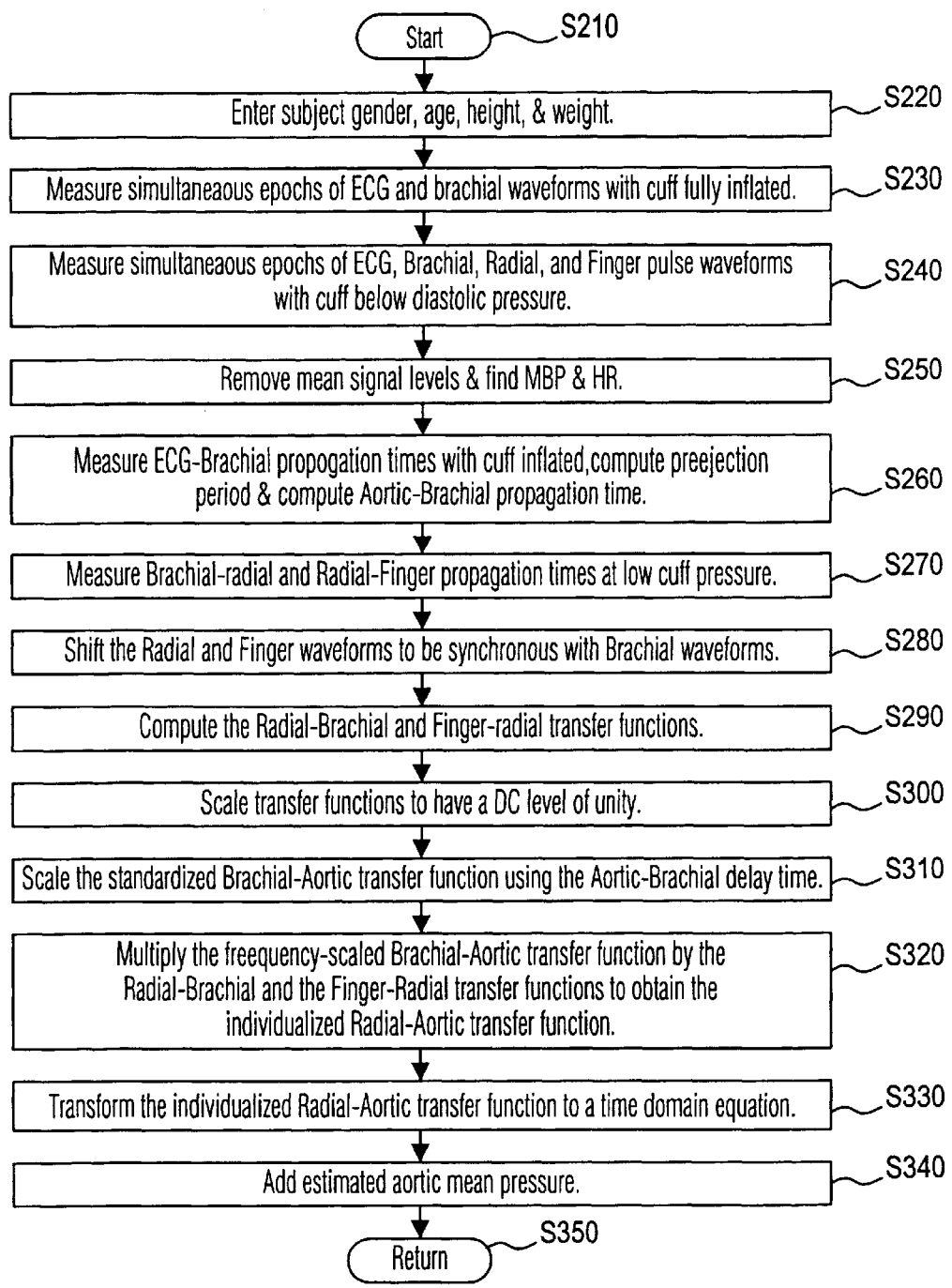
FIG. 15 illustrates a first exemplary method for adapting a normalized universal reverse transfer function and universal aortic blood pressure reconstruction model to a specific subject.

FIG. 15 illustrates a first exemplary method according to the invention for modifying a normalized universal reverse transfer function and universal aortic blood pressure reconstruction model to a specific subject. Adaptation of the standardized brachial transfer function for a specific subject is accomplished by essentially reversing the computational process as shown in FIG. 15.

Adaptation begins in step S210 when control proceeds to step S220. In step S220, the particular subject's relevant information (e.g., gender, age, height and weight) is identified. Subsequently, control proceeds to step S230 in which the method measures simultaneous epochs of ECG and brachial waveforms ($e_{ecg}(t)$, $P_a(t)$ and $P_b(t)$) with the blood pressure cuff fully inflated. Control then proceeds to step S240. In step S240, simultaneous measurement of the epochs of ECG, brachial, radial, and finger pulse waveforms are performed with the cuff pressure below diastolic pressure ($e_{ecg}(t)$, $P_b(t)$, $P_r(t)$ and $P_f(f)$) and proceeds to step S250. In step S250, the mean signal levels are removed to provide data for variables $e_{ecg}(t)$, $Pb(t)$, $p_r(t)$, $p_f(f)$ and the mean aortic blood pressure (MBP) and heart rate (HR) are found. Control then proceeds to step S260.

In step S260, the ECG-brachial propagation times with the blood pressure cuff inflated ($\Delta t_{ecg-b}$), computes the pre-ejection period (PEP=Regr($\Delta t_{ab}$, MBP, HR, gender, age, height, weight) are measured and the aortic-brachial propagation time ($\Delta t_{ab} = \Delta t_{ecg-b} - PEP$) are computed. Control then proceeds to step S270 in which the brachial-radial propagation time ($\Delta t_{br}$) and radial-finger propagation time ($\Delta t_{rf}$) are measured at low blood pressure cuff pressure. Control then proceeds to step S280. In step S280, the radial and finger waveforms are shifted to be synchronous with the brachial waveforms providing data for variables $p_b(t-\Delta t_{ab})$, $p_r(t-\Delta t_{ar})$, $p_f(f-\Delta t_{af})$. Using that data, in step S290, the radial-brachial transfer function, $H_{rb}(f) = P_b(f)/p_r(f)$, and finger-radial, $H_{fr}(f) = (P_r(f)/P_f(f))$, transfer function are computed. Control then proceeds to step S300 in which the transfer functions $H_{rb}(f)$ and $H_{fr}(f)$ are scaled to have a DC level of unity. Control then proceeds to step S310.

In step S310, the brachial-aortic transfer function $E_{ba-i}(f)$ is standardized using the aortic-brachial delay time (i.e., the natural frequency $\omega_{ab}$) obtained when the blood pressure cuff is fully inflated. Control then proceeds to step S320. In step S320, the frequency-scaled brachial-aortic transfer function $E_{ba-i}(f)$ is multiplied by the radial-brachial transfer function $H_{rb}(f)$ and the finger-radial transfer function $H_{fr}(f)$ to obtain the individualized radial-aortic transfer function $H_{ra}(f)$. Control then proceeds to step S330 in which the individualized radial-aortic transfer function are transformed to a time domain equation ($p_a(t)=f(p_r(t))$; control then proceeds to step S340. In step S340, the estimated aortic mean pressure is added to the time domain equation for the radial-aortic transfer function ($P_a(t)=P_a(t)+MBP$) and control proceeds to step S350. In step S350, control returns to the main method of constructing an individualized radial-to-aortic blood pressure reconstruction model.

This first exemplary method of determining the damping of the aortic-to-brachial segment of the propagation path has the advantage that the brachial-to-aortic transfer function is based upon an empirically derived model which incorporates information about the aortic-to-brachial branch of the propagation path. The information includes the subtle effects of branching, attenuation at bifurcations, and other hemodynamic factors. Such information is not included in conventional linear models derived from simple physical models as explained above in conjunction with FIG. 4.

However, the physiological information is averaged across the sample population used for developing the model. As a result, normal variation between subjects contributes to the inaccuracy of the reconstructed aortic blood pressure. An additional disadvantage of this method is that the standardized model requires storage of a large array representing the magnitude and phase of each frequency element of the transfer function. Nevertheless, this deficiency is overcome by expressing the standardized transfer function as an equation obtained by fitting the empirical function using any of a number of curve fitting techniques. However, this first exemplary method produces some loss of information contained within the empirical transfer due to the intrinsic smoothing of curve fitting techniques.

Figure 16:
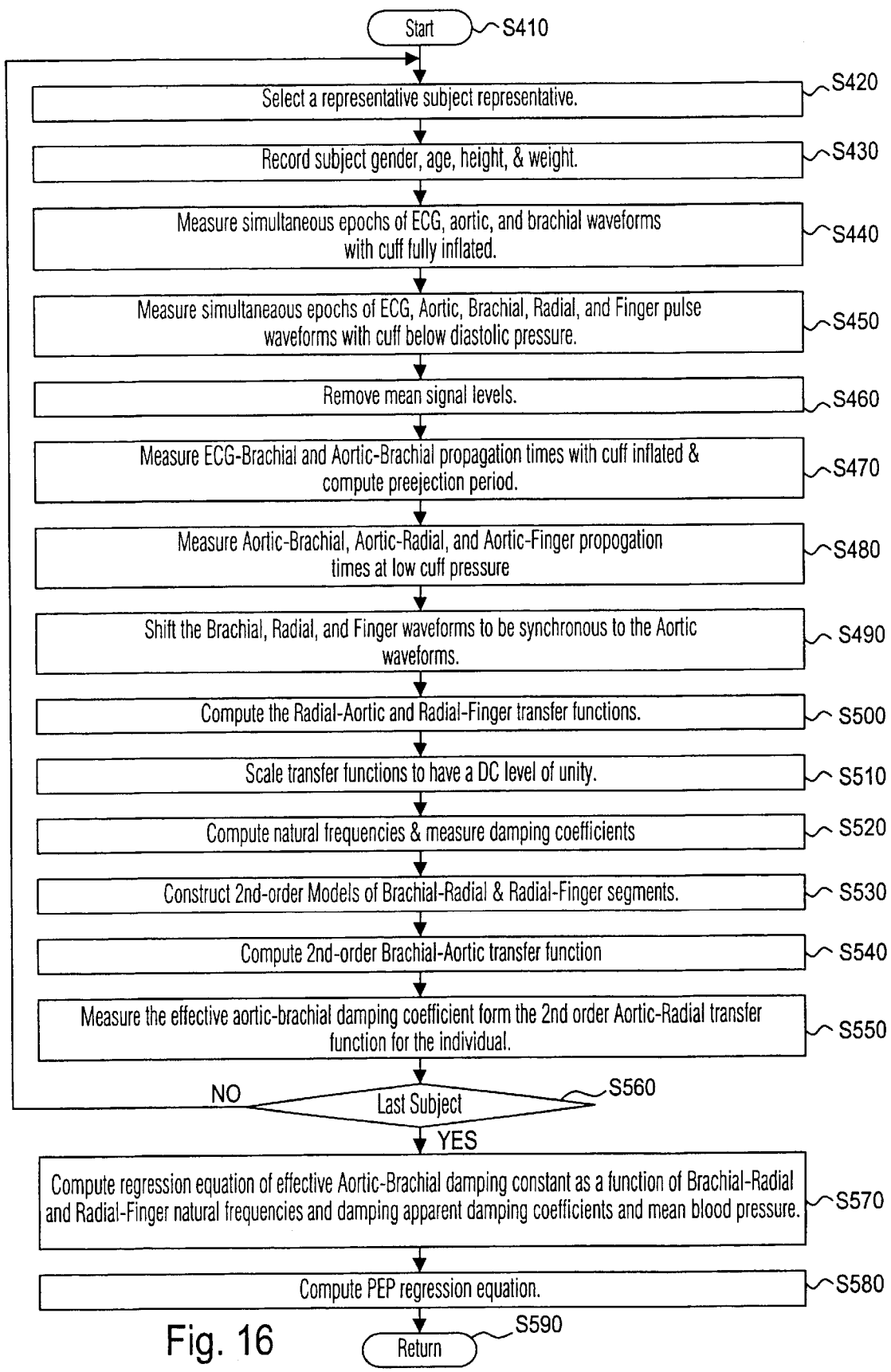
FIG. 16 illustrates a second exemplary method for developing a normalized universal reverse transfer function and universal aortic blood pressure reconstruction model.

In a second exemplary method of determining the damping of the aortic-to-brachial segment of the propagation path, the radial-to-aortic reverse model described by Eq. 22e for a subject is constructed using the subject's radial-to-finger transfer function, $H_{rf}(f)$, and second order transfer functions constructed for the subject. As illustrated in FIG. 16, control begins in step S410 when the method starts and control then proceeds to step S420. In step S420, a subject is selected as representative of the large number of subjects and control proceeds to step S430. In step S430, the subject's gender, age, height and weight are recorded and control proceeds to step S440. In step S440, simultaneous measurement of the epochs of ECG, aortic, and brachial waveforms are performed with the blood pressure cuff fully inflated. This measurement provides data for variables $e_{ecg}(t)$, $P_a(t)$ and $P_b(t)$. Subsequently, control proceeds to step S450.

In step S450, simultaneous measurement of the epochs of ECG, aortic, brachial, radial and finger pulse waveforms are performed with the blood pressure cuff inflated to a constant pressure below diastolic pressure to provide data for variables $e_{ecg}(t)$, $P_a(t)$, $P_b(t)$, $P_r(t)$ and $P_f(f)$. The constant cuff pressure level is selected to be sufficiently below diastolic pressure such that blood flow in the arm is minimally reduced. Such a level is found by monitoring the radial pulse amplitude and holding the cuff pressure constant after the radial pulse signal has become approximately constant. Control then proceeds to step S460. In step S460, the mean signal levels are removed from the data provided in step S450 to provide values for $e_{ecg}(t)$, $p_a(t)$, $p_b(t)$, $p_r(t)$ and $p_f(f)$ and control proceeds to step S470. Subsequently, the ECG-brachial propagation time, $\Delta t_{ecg-b}$, and aortic-brachial propagation time, $\Delta t_{ab}$, are measured with the blood pressure cuff fully inflated and the pre-ejection period, i.e., PEP= $\Delta t_{ecg-b} - \Delta t_{ab}$, is computed. Control then proceeds to step S480, in which the propagation times through the aortic-brachial, $\Delta t_{ab}$, aortic-radial, $\Delta t_{br}$, and aortic-finger $\Delta t_{af}$, segments with the cuff inflated at low cuff pressure are calculated. Next, in step S490, the brachial, radial and finger waveforms are shifted to be synchronous with the aortic waveforms providing data for variables $p_b(t-\Delta t_{ab})$, $p_r(t-\Delta t_{ar})$, $p_f(f-\Delta t_{af})$. Using that data, in step S500, the radial-aortic transfer function, $H_{ra}(f)=P_a(f)/P_r(f)$, and radial-finger transfer function, $H_{rf}(f)=P_f(f)/P_r(f)$. Control then proceeds to step S510 in which the transfer functions $H_{ra}(f)$ and $H_{rf}(f)$ are scaled to have a DC level of unity. Control continues to step S520.

In step S520, the natural frequencies $\omega_{ab}$, $\omega_{br}$ and $\omega_{rf}$ are computed and the damping coefficients $\zeta_{ab}$, $\zeta_{br}$ and $\zeta_{rf}$ are measured. The natural frequency and damping coefficient parameters for the second order transfer functions of the brachial-to-radial and radial-to-finger segments are obtained from the measured transfer functions, $H_{rf}(f)$ and $H_{br}(f)$. The resonance frequency is chosen as the approximate natural frequency and the peak magnitude used to estimate the segment's effective damping coefficient. The aortic-to-brachial segment natural angular frequency is computed from the aortic-to-brachial propagation time when the occlusion cuff is inflated above systolic pressure. The damping coefficient parameter of the aortic-to-brachial segment is obtained using a regression equation relating the aortic-to-brachial damping constant to the brachial-to-radial and radial-to-finger damping constants.

Control then proceeds to step S530. In step S530, the second order transfer function models of the brachial-radial and radial-finger segments $S_{br}$ and $S_{rf}$ are constructed. Control then proceeds to step S540 in which the second order brachial-aortic transfer function $S_{ab-i}(f)=H_{rf}(f)/(S_{br}(f)*S_{fr}(f)*H_{ra}(f))$ is constructed. The parameters of the brachial-to-radial and radial-to-finger segment second order equations are obtained from the measured transfer functions for the segments as described earlier. Control then proceeds to step S550. In step S550, the effective aortic-brachial damping coefficient from the second order aortic-radial transfer function is measured for the individual and control proceeds to step S560.

In step S560, a determination is made whether all of the subjects in the subject pool have been selected in step S420 and analyzed in step S430–S550. If a subject in the pool has not been selected and analyzed, control returns to step S420 to select and analyze the additional subject(s). Alternatively, if all subjects have been selected and analyzed, control proceeds to step S570.

Accordingly, following collection from an adequate number of subjects, a regression equation is computed for the subject population which relates the damping constant ($\zeta\omega_0$) of the aortic-to-brachial segment to the damping constants of the brachial-to-radial and radial-to-finger segments. The measured natural angular frequency, $\omega_{ab}=1/(\Delta t_{ab})$, measured when the cuff is fully inflated, is used as the natural frequency for the subject such that the resulting equation will have the form:

$$\omega_{ab}\zeta_{ab}=A\omega_{br}\zeta_{br}+B\omega_{rf}\zeta_{rf}+C \qquad (26)$$

where A, B, and C are the coefficients of the regression equation.

Therefore, in step S570, the regression equation of effective aortic-brachial damping constant is computed as a function of brachial-radial and radial-finger natural frequencies and apparent damping coefficients and mean blood pressure, i.e., $\omega_{ab}\zeta_{ab}=\text{Regr}(\omega_{br-i}\zeta_{br-i}, \omega_{rf-i}\zeta_{rf-i}, MBP_i)$. Control then proceeds to step S580.

In step S580, the pre-ejection period regression equation PEP=Regr($\Delta t_{ab}$, MBP, HR, gender, age, height, weight) average of the standardized transfer functions for all the subjects is calculated. The regression equation is derived from damping constants obtained from analysis of aortic, brachial, radial, and finger blood pressure waveform data collected in controlled studies of a large number of subjects, as shown in FIG. 16. In these studies, aortic pressure measurements are obtained simultaneously with the brachial, radial and finger waveforms. The effective aortic-to-brachial damping coefficient is obtained using a restatement of Eq. 22e:

$$S_{ab}(f) = \frac{H_{fr}(f)}{S_{br}(f)*S_{rf}(f)*H_{ra}(f)} = \frac{\omega_{ab}^2}{(2j\pi f)^2 + 2\zeta_{ab}\omega_{ab}(2j\pi f) + \omega_{ab}^2} \qquad (27)$$

Control then proceeds to step S590. In step S590, control returns to the main method of constructing an individualized radial-to-aortic blood pressure reconstruction model.

Figure 17:
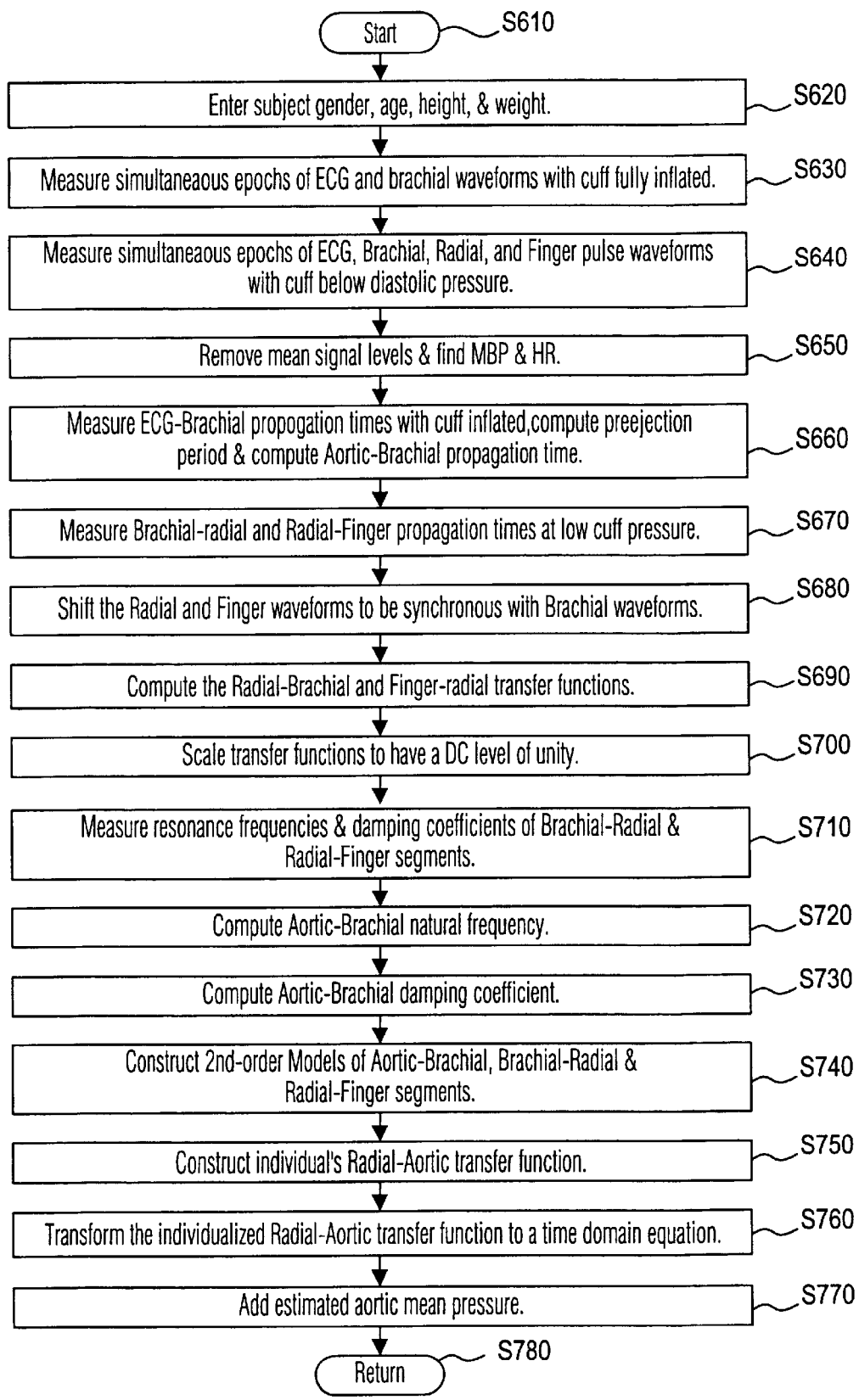
FIG. 17 illustrates a second exemplary method for adapting a normalized universal reverse transfer function and universal aortic blood pressure reconstruction model to a specific subject.

FIG. 17 illustrates a second exemplary method for modifying a normalized universal reverse transfer function and universal aortic blood pressure reconstruction model to a specific subject. As explained in connection with the method illustrated in FIG. 15, adaptation of the standardized brachial transfer function for a specific subject is accomplished by essentially reversing the computational process as shown in FIG. 17. The adaptation method begins in step S610 and control proceeds to step S620. In step S620, the particular subject's relevant information (e.g., gender, age, height and weight) is identified. Subsequently, control proceeds to step S630 in which simultaneous measurement of the epochs of ECG and brachial waveforms ($e_{ecg}(t)$, $P_a(t)$ and $P_b(t)$) are performed with the blood pressure cuff fully inflated. Control then proceeds to step S640. In step S640, simultaneous measurements of epochs of ECG, brachial, radial, and finger pulse waveforms with cuff below diastolic pressure, $e_{ecg}(t)$, $P_b(t)$, $P_r(t)$ and $P_f(f)$ are performed and control proceeds to S650, the mean signal levels are removed to provide data for variables $e_{ecg}(t)$, $p_b(t)$, $p_r(t)$, $p_f(f)$ and the mean aortic blood pressure (MBP) and heart rate (HR) are found. Control then proceeds to step S660.

In step S660, the ECG-brachial propagation times with the blood pressure cuff inflated, $\Delta t_{ecg-b}$, is measured, the pre-ejection period, PEP=Regr($\Delta t_{ab}$, MBP, HR, gender, age, height, weight), is computed and the aortic-brachial propagation time $\Delta t_{ab} = \Delta t_{ecg-b} - \text{PEP}$ is computed. As above, the pulse propagation times $\Delta t_{ab}$, $\Delta t_{br}$, $\Delta t_{rf}$, and transfer functions $H_{rf}(f)$ and $H_{br}(f)$ are obtained from the ECG, brachial, radial and finger pulse waveforms. Control then proceeds to step S670 in which the brachial-radial propagation time $\Delta_{br}$ and radial-finger propagation time $\Delta t_{rf}$ are measured at a cuff pressure below diastolic blood pressure. Control proceeds to step S680. In step S680, the radial and finger waveforms are shifted to be synchronous with the brachial waveforms providing data for variables $p_b(t-\Delta t_{ab})$, $p_r(t-\Delta t_{ar})$, $p_f(f-\Delta t_{af})$. Using that data, in step S690, the radial-brachial transfer function, $H_{rb}(f)=P_b(f)/P_r(f)$, and finger-radial, $H_{fr}(f)=P_r(f)/P_f(f)$, transfer function are computed. Control then proceeds to step S700 in which the transfer functions $H_{rb}(f)$ and $H_{fr}(f)$ are scaled to have a DC level of unity. Control then proceeds to step S710.

In step S710, the resonance frequencies and damping coefficients of the brachial-radial and radial-finger segments, $f_{br}$, $f_{rf}$, $\zeta_{br}$ and $\zeta_{rf}$ are measured and control proceeds to step S720. The damping constants determined from $H_{rf}(f)$ and $H_{br}(f)$ and the aortic-to-brachial pulse propagation time, $\Delta t_{ab}$, are used to estimate the aortic-to-brachial damping constant using the regression Eq. 26. In step S720, the aortic-brachial natural frequency $f_{ab}=1/(8\pi t_{ab})$ are computed and control proceeds to step S730. In step S730, the aortic-brachial damping coefficient $\zeta_{ab-i}=\text{Regr}(\omega_{br-i}, \zeta_{br-i}, \omega_{rf-i}, \zeta_{rf-i}, \text{MBP}_i)/\omega_{ab-i}$ is computed and control proceeds to step S740. In step S740, the second-order transfer function models of aortic-brachial $S_{ab}$, brachial-radial $S_{br}$ and radial-finger $S_{rf}$ segments are constructed and control proceeds to step S750.

In step S750, the individual's radial-aortic transfer function $H_{ra-i}=h_{rf}(f)/S_{ab}(f)S_{br}(f)S_{rf}(f))$ and the finger-radial transfer function $H_{fr}(f)$ are constructed to obtain the individualized radial-aortic transfer function $H_{ra}(f)$. The second order models of each segment are constructed and combined with the radial-to-finger transfer function, $H_{rf}(f)$, to construct the radial-to-aortic transfer function, $H_{ra}(f)$, as defined by Eq. 22e. Control then proceeds to step S760 in which the individualized radial-aortic transfer function is converted to a time domain equation $p_a(t)=f(p_r(t))$ and control proceeds to step S770. The radial-to-aortic transfer function is thus transformed into the time domain to produce the radial-to-aortic model for reconstructing the aortic waveform from the radial waveform. In step S770, the estimated aortic mean pressure is added to the time domain equation for the radial-aortic transfer function $P_a(t)=p_a(t)+\text{MBP}$ and control proceeds to step S780. In step S780, control returns to the main method of constructing an individualized radial-to-aortic blood pressure reconstruction model.

This second exemplary method for modifying the normalized universal reverse transfer function and universal aortic blood pressure reconstruction model to the specific subject has the advantage of requiring only the use of a regression equation with a small number of coefficients for estimating the aortic-to-brachial damping constant. All other information required for constructing the aortic blood pressure construction model is obtained from the subject at the time of calibration. The shortcoming of the method is that it assumes a linear model for aortic-to-radial pulse propagation.

In a third exemplary method of determining the damping of the aortic-to-brachial segment of the propagation path, the empirical transfer function is estimated using brachial/radial waveform. The assumed brachial-to-radial second order transfer function is represented by $$H_{br}(f) = \frac{\omega_{br}^2\omega_{rf}^2 + Z_3(2j\pi f) + \omega_{br}^2(2j\pi f)^2}{(2j\pi f)^4 + Z_1(2j\pi f)^3 + Z_2(2j\pi f)^2 + Z_3(2j\pi f) + \omega_{br}^2\omega_{rf}^2} \tag{28}$$

where $$Z_1 = 2(\zeta_{ab}\omega_{ab} + \zeta_{br}\omega_{br} + \zeta_{rf}\omega_{rf}) \tag{29}$$

$$Z_2 = \omega_{br}^2 + \omega_{rf}^2 + 4\zeta_{ab}\omega_{ab}(\zeta_{br}\omega_{br} + \zeta_{rf}\omega_{rf}) + 4\zeta_{br}\omega_{br}\zeta_{rf}\omega_{rf} \tag{30}$$

$$Z_3 = 2\zeta_{ab}\omega_{ab}(\omega_{br}^2 + \omega_{rf}^2) + 2\zeta_{br}\omega_{br}\omega_{rf}^2 + 2\zeta_{rf}\omega_{rf}\omega_{br}^2 \tag{31}$$

The parameters of the transfer function are obtained using a sub-optimum or/and extended least squares method, for example, see, Billings, S. A. and Voon, W. S. F. (1984) "Least Squares Parameter Estimation Algorithms for Nonlinear Systems," *Int. J Systems Sci.*, Vol. 15, No. 6, pp. 601–615 incorporated herein by reference in its entirety. In this method, the estimated empirical transfer functions assumed to have the form:

$$H_{br}^{em}(f) = H_{br}(f) + e(f) \tag{32a}$$

$$= \frac{\omega_{br}^2\omega_{rf}^2 + Z_3(2j\pi f) + \omega_{br}^2(2j\pi f)^2}{(2j\pi f)^4 + Z_1(2j\pi f)^3 + Z_2(2j\pi f)^2 + Z_3(2j\pi f) + \omega_{br}^2\omega_{rf}^2} + e(f) \tag{32b}$$

where $e(f)$ is white noise. Multiplying both sides of the equation by the denominator of the first term at the left side of the equation, gives:

$$H_{br}^{em}(f)((2j\pi f)^4+Z_1(2j\pi f)^3+Z_2(2j\pi f)^2+Z_3(2j\pi f)+\omega_{br}^2\omega_{rf}^2)= \omega_{br}^2\omega_{rf}^2+Z_3(2j\pi f)+\omega_{br}^2(2j\pi f)^2$$

$$+e(f)((2j\pi f)^4+Z_1(2j\pi f)^3+Z_2(2j\pi f)^2+Z_3(2j\pi f)+\omega_{br}^2\omega_{rf}^2) \tag{33}$$

which, after rearrangement, becomes:

$$H_{br}^{em}(f) = 1 + \frac{1}{\omega_{br}^2\omega_{rf}^2}(1-H_{br}^{em}(f))Z_3(2j\pi f) + \tag{34}$$

$$\frac{1}{\omega_{br}^2\omega_{rf}^2}(\omega_{br}^2 - H_{br}^{em}(f)Z_2)(2j\pi f)^2 \frac{1}{\omega_{br}^2\omega_{rf}^2}H_{br}^{em}(f)Z_1(2j\pi f)^3 -$$

$$\frac{1}{\omega_{br}^2\omega_{rf}^2}H_{br}^{em}(f)(2j\pi f)^4 + e(f)\frac{1}{\omega_{br}^2\omega_{rf}^2}$$

$$((2j\pi f)^4 + Z_1(2j\pi f)^3 + Z_2(2j\pi f)^2 + Z_3(2j\pi f) + \omega_{br}^2\omega_{rf}^2)$$

For simplicity, replacing $H_{br}(F)$ by y and $2j\pi f$ by x, gives:

$$y = 1 + \frac{1}{\omega_{br}^2\omega_{rf}^2}(1-y)Z_3 x + \frac{1}{\omega_{br}^2\omega_{rf}^2}(\omega_{br}^2 - yZ_2)x^2 - \frac{1}{\omega_{br}^2\omega_{rf}^2}Z_1 yx^3 - \tag{35}$$

$$\frac{1}{\omega_{br}^2\omega_{rf}^2}yx^4 + e(x)\frac{1}{\omega_{br}^2\omega_{rf}^2}(x^4 + Z_1x^3 + Z_2x^2 + Z_3x + \omega_{br}^2\omega_{rf}^2)$$

Further simplification produces:

$$y=1+\theta_1(1-y)x+\theta_2 x^2+\theta_3 yx^2+\theta_4 yx^3+\theta_5(ex^4+yx^4)+\theta_6 ex^3+\theta_7 ex^2+\theta_8 ex+e \tag{36}$$

where:

$$\theta_1 = \frac{Z_3}{\omega_{br}^2 \omega_{rf}^2} \quad (37a)$$

$$\theta_2 = \frac{1}{\omega_{rf}^2} \quad (37b)$$

$$\theta_3 = -\frac{Z_2}{\omega_{br}^2 \omega_{rf}^2} \quad (37c)$$

$$\theta_4 = -\frac{Z_1}{\omega_{br}^2 \omega_{rf}^2} \quad (37d)$$

$$\theta_5 = -\frac{1}{\omega_{br}^2 \omega_{rf}^2} \quad (37e)$$

$$\theta_6 = Z_1 \quad (37f)$$

$$\theta_7 = Z_2 \quad (37g)$$

$$\theta_8 = Z_3 \quad (37h)$$

Figure 18:
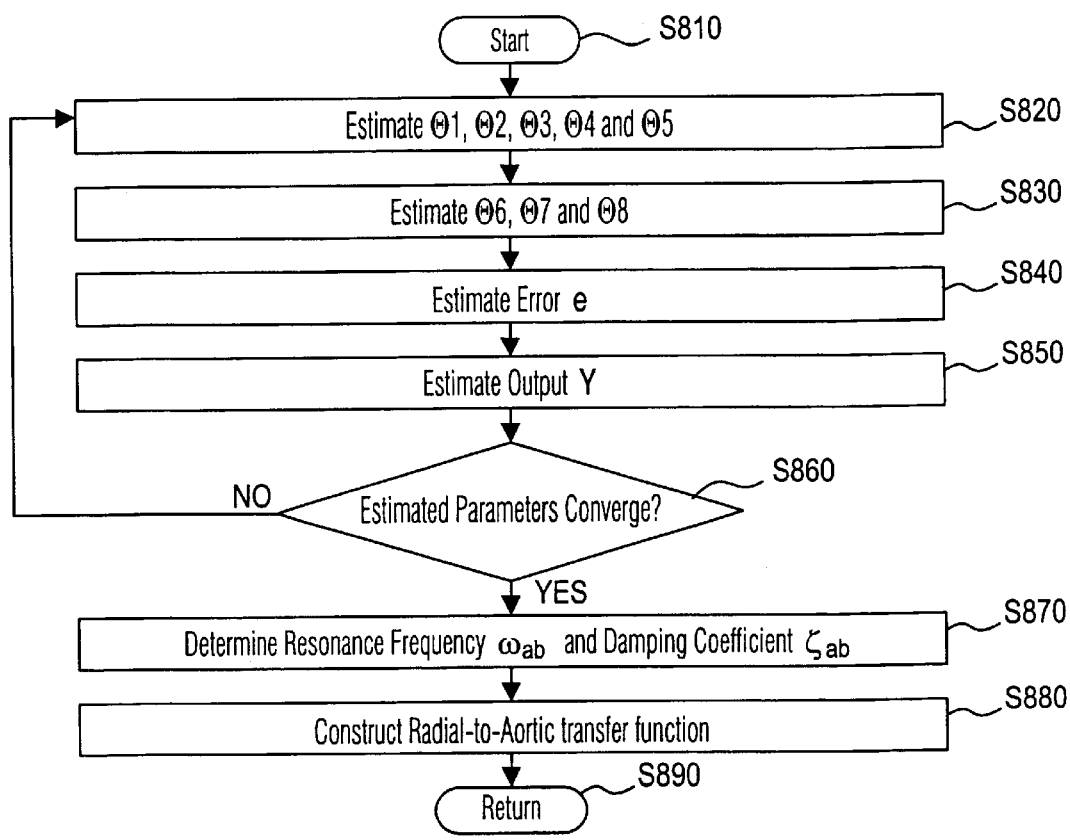
FIG. 18 illustrates an exemplary least squares method employed to estimate output, error and associated parameters.

The least squares method (extended and/or sub-optimum form) is then employed to estimate the output y, error ê and the parameters $\hat{\theta}_1$, $\hat{\theta}_2$, $\hat{\theta}_3$, $\hat{\theta}_4$, and $\hat{\theta}_5$. For example, such a method is now explained. As shown in FIG. 18, the method begins in step S810 and control proceeds to step S820. In step S820, the ordinary least squares method is used to estimate $\hat{\theta}_1$, $\hat{\theta}_2$, $\hat{\theta}_3$, and $\hat{\theta}_4$, $\hat{\theta}_5$ using Eq. 36. Control then proceeds to step S830. In step S830, $\theta_6$, $\theta_7$, and $\theta_8$ are estimated using the relations:

$$\hat{\theta}_6 = \frac{\hat{\theta}_4}{\hat{\theta}_5} \quad (38a)$$

$$\hat{\theta}_7 = \frac{\hat{\theta}_3}{\hat{\theta}_5} \quad (38b)$$

$$\hat{\theta}_8 = -\frac{\hat{\theta}_1}{\hat{\theta}_5} \quad (38c)$$

Control then proceeds to step S840 in which the error e is estimated using the equation:

$$\hat{e} = \frac{y - 1 - \theta_1(1-y)x - \theta_2 x^2 - \theta_3 y x^2 - \theta_4 y x^3 - \theta_5 y x^4}{\theta_5 x^4 + \theta_6 x^3 + \theta_7 x^2 + \theta_8 x + 1} \quad (39)$$

Subsequently, control continues to step S850 in which the output y is estimated as follows:

$$\hat{y} = y - \hat{e} \quad (40)$$

Therefore, in step S850, the ordinary least squares can be used to the following equation:

$$y = 1 + \theta_1(1-\hat{y})x + \theta_2 x^2 + \theta_3 \hat{y} x^2 + \theta_4 \hat{y} x^3 + \theta_5(\hat{e} x^4 + \hat{y} x^4) + \theta_6 \hat{e} x^3 + \theta_7 \hat{e} x^2 + \theta_8 \hat{e} x + e \quad (41)$$

Control then proceeds to step S860 in which a determination is made whether the estimated parameters have converged. If the estimated parameters have not converged, control returns to step S820 and steps S820–S860 are re-performed until the estimated parameters have converged. Alternatively, if the estimated parameters have converged, control proceeds to step S870.

In step S870, the resonance frequency, $\omega_{ab}$, and damping coefficients, $\zeta_{ab}$, are determined by substitution of the brachial-to-radial and radial-to-finger segment parameters into Eqs. 29 and 30 and solving for the aortic-to-brachial parameters. Control then proceeds to step S880. Having obtained all of the parameters of the pulse propagation path, in step S880, the radial-to-aortic transfer function is then constructed using Eq. 22e. Control proceeds to step S890 in which the method ends.

This third exemplary method of determining the damping of the aortic-to-brachial segment of the propagation path has the advantage that it does not require prior knowledge obtained from other subjects. The shortcoming of this exemplary method is that it assumes that all segments of the pulse propagation path can be represented by a linear combination of inertances and compliances and a single terminal resistance.

Optimizing the Reconstruction Model

Each of the exemplary modeling methods of determining the damping of the aortic-to-brachial segment of the propagation path assume that pulse propagation is a linear process. However, as discussed earlier, this assumption is accurate only for limited ranges of mean pressure and for wave propagation in only one direction. The simplest approach to solving the range limitation problem is to optimize the reconstruction model by periodically re-calibrating the models. In particular, the radial-to-aortic model must be re-calibrated whenever the cardiovascular state changes significantly. Significant cardiovascular state changes are produced by changes in mean pressure, vasomotor tone, and the peripheral resistance.

Initiating re-calibration based upon mean pressure is accomplished by continuously monitoring the mean radial pressure. This continuous monitoring is a function available in virtually all patient monitors. The criteria to initiate the re-calibration is determined from controlled studies of human subjects. Thresholds in the criteria are based upon the desired aortic waveform accuracy and the statistically determined error as a function of mean pressure change from the calibration point. The re-calibration thresholds are specific to the models used, the reconstruction process, and the specific instruments and signals used.

Although devices for continuously monitoring the mean radial pressure are conventionally available, a cardiovascular state change monitor is also necessary to identify changes in the vasomotor tone of the arteries caused by nervous system or humoral control mechanisms. This cardiovascular state change monitor monitors the pulse wave velocity as determined by the propagation time from the heart to the radial or finger pulse measurement site. Many methods are conventionally known for accomplishing this measurement (see, for example, Lane, James D., Greenstadt, Lisa, Shapiro, David, and Rubinstein, Eduardo. "Pulse Transit Time and Blood Pressure: An Intensive Analysis," Psychophysiology, 1983, Vol. 20, No. 1, pp. 45–49, and various patents see, for example, U.S. Pat. No. 5,743,856 issued to Oka et al. Apr. 28, 1998, incorporated herein by reference in their entireties). Again, the threshold criteria for initiating the re-calibration of the models is empirically determined from controlled studies of human subjects and specified accuracy ranges.

A peripheral resistance monitor identifies changes in the peripheral resistance to indicate changes in the cardiovascular state. Although several designs are practical to implement a peripheral resistance monitor, the simplest mechanism monitors the amplitude of the peripheral waveform. Changes in peripheral resistance usually produce corresponding changes in the pulse amplitude as well as changes in mean pressure. However, baroreceptor responses can compensate for these changes in pulse amplitude and mean pressure.

A more accurate peripheral resistance monitor continuously monitors the total damping of the system using the radial and finger pressure waveforms. As explained above, the peak magnitude of the radial-to-finger transfer function is dependent upon the total damping of the system, which, in turn, is primarily dependent upon the terminal resistance of the arterial branch. Therefore, the peak value of the radial-to-finger transfer function, or the more computationally efficient power spectrum, serves as a monitoring variable specific for peripheral resistance changes.

As with all re-calibration thresholds, the magnitude change sufficient to initiate a re-calibration must be determined empirically from controlled human subject studies using identical aortic reconstruction methods and identical desired accuracy ranges.

One major simplifying assumption made during model development is the assumption that the resistive elements of the large vessels is negligible relative to the terminal resistance of the arterial branch. However, this assumption does not hold if the terminal resistance is very low. This is evidenced by the magnitude of the highly damped subject transfer functions, shown in FIG. 3, where it is seen that magnitude values approaching zero frequency are less than unity. When the terminal resistance is low, significant resistive losses occur between the aorta and radial measurement sites. Resistive losses occur in all frequency components of the propagating pulse and produce an overall reduction in the amplitude of the radial waveform.

However, the proportionality of the resistive losses to the damping coefficient provides a mechanism for correcting for their presence. This correction is accomplished by applying a mathematical relation which produces a multiplicative correction constant based upon the damping coefficients of the brachial-to-aortic, radial-to-brachial and the finger-to-radial transfer functions. This application can take the form of application of a multiple regression equation obtained from data collected from controlled studies of human subjects.

The multiple regression equation and its coefficients are determined empirically from controlled human subject studies using the identical embodiment of the aortic reconstruction method. For a specific subject, the damping coefficients are determined from the specific model construction process used. The damping coefficients are used with the empirically determined correction equation to produce a correction constant. The reconstructed aortic pressure waveform is then multiplied by the correction constant to produce the corrected waveform prior to its display and use.

Finally, the radial-to-aortic model obtained by any of the aforementioned exemplary methods is a combination of measured transfer functions and a brachial transfer function estimated from the measured transfer functions. Practical limitations of sampling rate, signal noise, computational error, and other factors introduce errors into the measured parameters that are then incorporated into the brachial-to-aortic transfer function. These errors are then compounded when they are combined into the radial-to-aortic model and the resulting estimate of the aortic pressure. Therefore, a radial-to-aortic model adapter that adjusts the radial-to-aortic model to minimize error from these sources is needed.

Minimizing error is accomplished by estimating the error of the reconstructed waveform and then adjusting the model to minimize the error. The errors are most apparent in any waveform reconstructed by the brachial-to-aortic segment of the model because the error sources are consolidated in that segment.

Following estimation of the brachial-to-aortic model and its combination with the measured finger-to-radial and radial-to-brachial transfer functions to form the radial-to-aortic model, the aortic-to-brachial model is constructed. The aortic-to-brachial model is then constructed by either inverting the brachial-to-aortic transfer function or constructing the time domain aortic-to-brachial model using the estimated natural frequency $\omega_{ab}$ and damping coefficient $\zeta_{ab}$.

The radial pressure waveform signal is passed through the radial-to-aortic model to reconstruct the aortic waveform for one or more heartbeats for which the brachial pressure waveform was measured. The reconstructed aortic waveform is then used as the input to the estimated aortic-to-brachial model to reconstruct the brachial waveform. Note that this method compounds any errors in the estimated brachial-to-aortic model. The reconstructed brachial waveform is then compared to the measured brachial waveform to determine an estimate of error of reconstruction. If the error is unacceptable, the damping coefficient of the brachial segment is adjusted and the process repeated. This continues until an acceptable residual error is obtained or until a minimum error has been bound.

Figure 19:
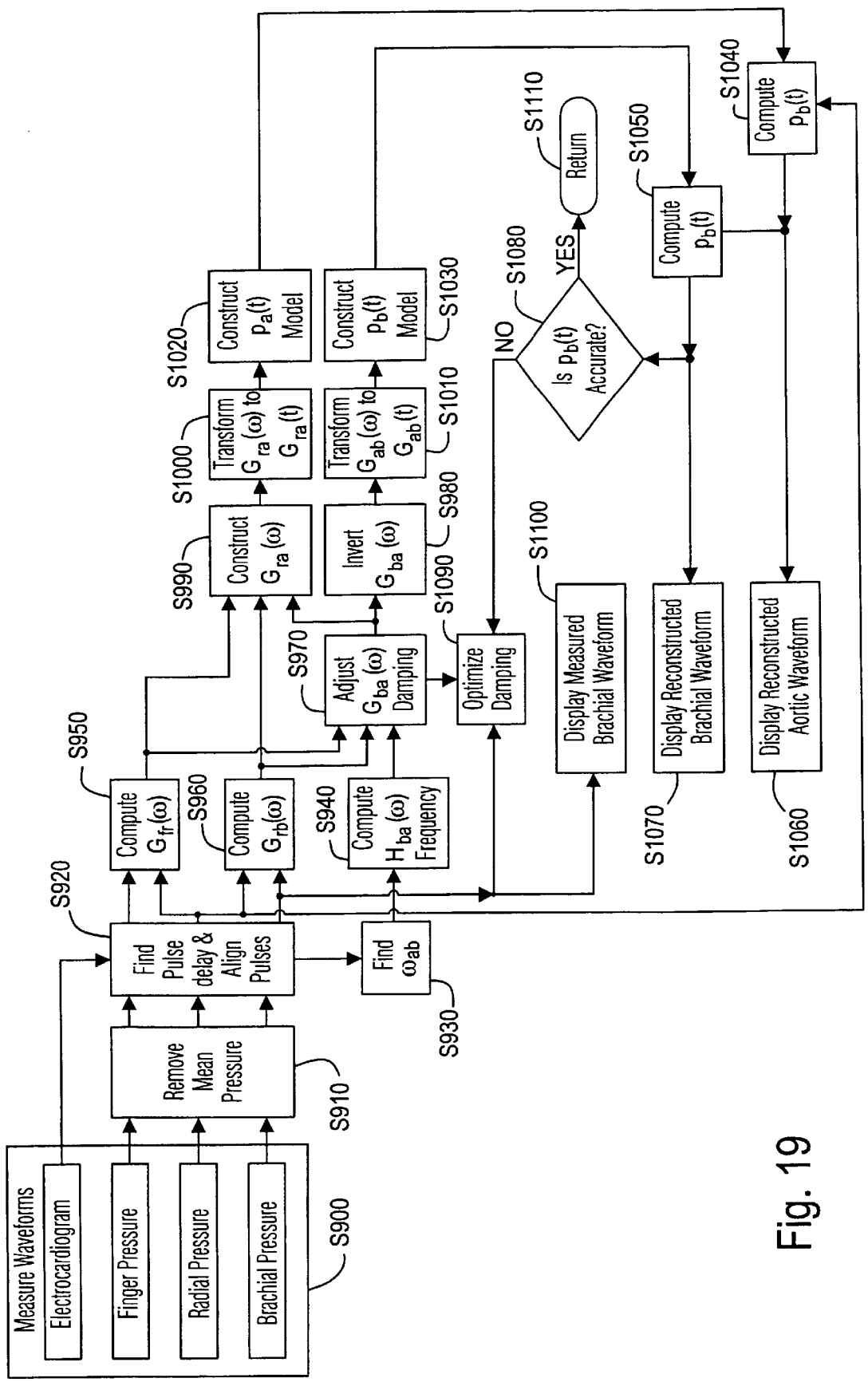
FIG. 19 illustrates a process for constructing an individualized radial-to-aortic blood pressure reconstruction model.

FIG. 19 illustrates an exemplary method for constructing the time domain aortic-to-brachial model using the estimated natural frequency and damping. In this exemplary method, step S900 is the simultaneous measurement of a signal, such as the ECG signal, indicating the start of the aortic blood pressure pulse, and the blood pressure pulse waveforms at the junctures of each segment of the modeled system such as the brachial artery, radial artery, and fingertip. The measurements are made during a non-invasive blood measurement made using an occlusion cuff. At two times during the process of making the oscillometric blood pressure measurement, simultaneous samples of one or more beats of the ECG, brachial, radial, and finger blood pressure waveforms are recorded, corrected for frequency response characteristics of the pulse transducers, and the waveforms saved in memory.

Figure 21:
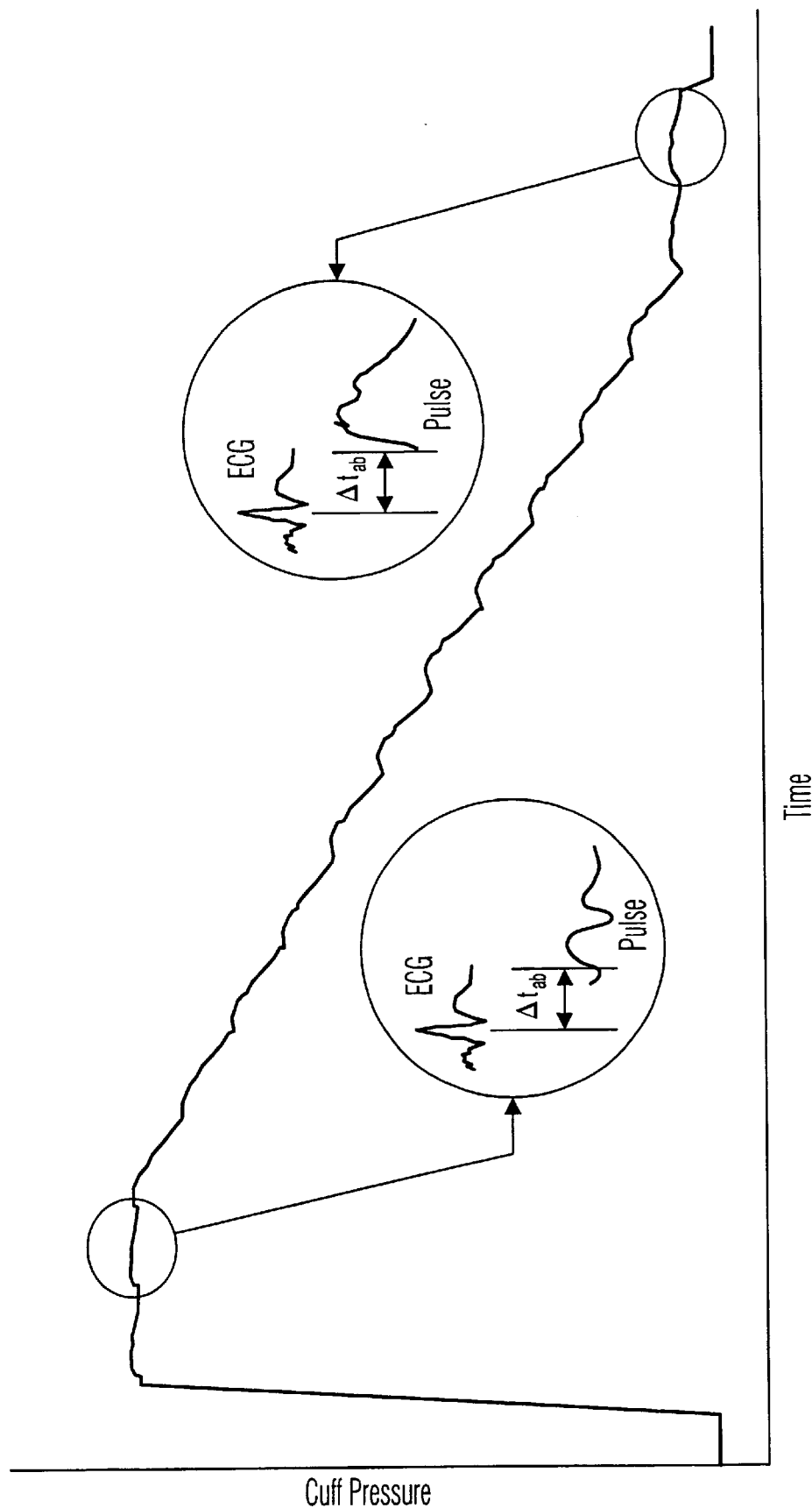
FIG. 21 illustrates cuff pressure profile used for measuring $\Delta t_{ab}$ and brachial waveform.

As shown in FIG. 21, the first set of measurements are made after an occlusion cuff has been inflated to a maximum pressure well above systolic pressure. After attainment of the maximum pressure, the cuff pressure is maintained at a constant level for a period of time. This period of time is sufficient to include one or more complete heartbeats and the sensing of the peripheral blood pressure pulses produced by the heartbeats. The cuff pressure is then allowed to deflate in a controlled fashion while the brachial blood pressure is measured. The cuff pressure is allowed to fall to a pressure well below diastolic pressure that produces a minimum restriction of the underlying arterial vessel. The pressure is again held constant at this lower pressure to collect one or more heartbeats at all points in the pulse wave propagation path. The timing of this period in the cuff pressure measurement cycle is shown in FIG. 21.

As shown in FIG. 19, the exemplary method for constructing the time domain aortic-to-brachial model using the estimated natural frequency and damping proceeds to step S910 in which the mean signal level is removed from the measured signals. Control then proceeds to step S920 in which the blood pressure pulses are aligned by removing the propagation delay between the pulses. As part of step S920, the pulse propagation time ($\Delta t$) for each arterial segment is determined. Control then moves to step S930 in which propagation times are then used to compute the natural frequencies ($\omega$). The natural frequency of the aortic-to-brachial segment is then used to scale the universal brachial-to-aortic transfer function to the subject being monitored in step S940. Control then proceeds to step S950.

In step S950, the finger-to-radial transfer function is calculated using the finger pressure waveform as the input and the radial pressure as the output. Control then proceeds to step S960 wherein the radial-to-brachial transfer function is computed using the radial pressure as the input and the brachial pressure as the output. The results of steps 950 and 960 are saved at the conclusion of step 960. Control then proceeds to step S970, in which the finger-to-radial and radial-to-brachial transfer functions are used to estimate the total damping of the brachial-to-aortic transfer function by one of the methods illustrated in FIGS. 15 and 17 previously discussed. Control then continues to step S980. In step S980, the estimated brachial-to-aortic transform is inverted to produce the estimated aortic-to-brachial transfer function and control proceeds to step S990.

In step S990, the radial-to-aortic transfer function is constructed by multiplying the measured brachial-to-radial and estimated brachial-to-aortic transfer functions. Control continues to step S1000, in which a transformation is performed on $G_{ra}(\omega)$ to produce the time domain equation $g_{ra}(t)$. In step S1010, a transformation is performed on $G_{ab}(\omega)$ to produce the time domain equation $g_{ab}(t)$ and control proceeds to step S1020. In step S1020, the time domain equation $g_{ra}(t)$ is used to construct the $p_a(t)$ model for estimation of the linear, time-dependent component of the aortic pulse model. In step S1030, the time domain equation $g_{ab}(t)$ is used to construct the $p_b(t)$ model for estimation of the linear, time-dependent component of the brachial pulse model. Control then proceeds to step S1040 in which a reconstruction of the aortic waveform is computed using the radial waveform used to construct the aortic reconstruction model, $p_a(t)$. Control then proceeds to step S1050. In step S1050 a reconstruction of the brachial pressure waveform is computed using the reconstructed aortic pressure waveform as the input to the brachial reconstruction model, $p_b(t)$. The method then proceeds to step S1060. In step S1060, the reconstructed aortic waveform is displayed, and control proceeds to step S1070. In step 1070, the reconstructed brachial waveform is displayed. Control then proceeds to step S1080. In step S1080, the estimated brachial waveform is compared to the measured brachial waveform and their difference compared with a figure of merit of waveform accuracy such as the root mean square (RMS) error. If the waveform is not deemed accurate as a result of the comparison, control proceeds to step S1090. In step S1090, the brachial-to-aortic damping coefficient used in step S970 is adjusted and the models reconstructed in steps S980–S1050.

This optimization process continues until the figure of merit is met or a minimum error between the measured and reconstructed brachial waveform is obtained. Upon completion of the optimization process, when the brachial waveform of step S1080 is accurate, the radial-to-aortic waveform reconstruction model is ready for use and control proceeds to step S1110. In step S1110, the individualized radial-to-aortic model development process ends.

Figure 20:
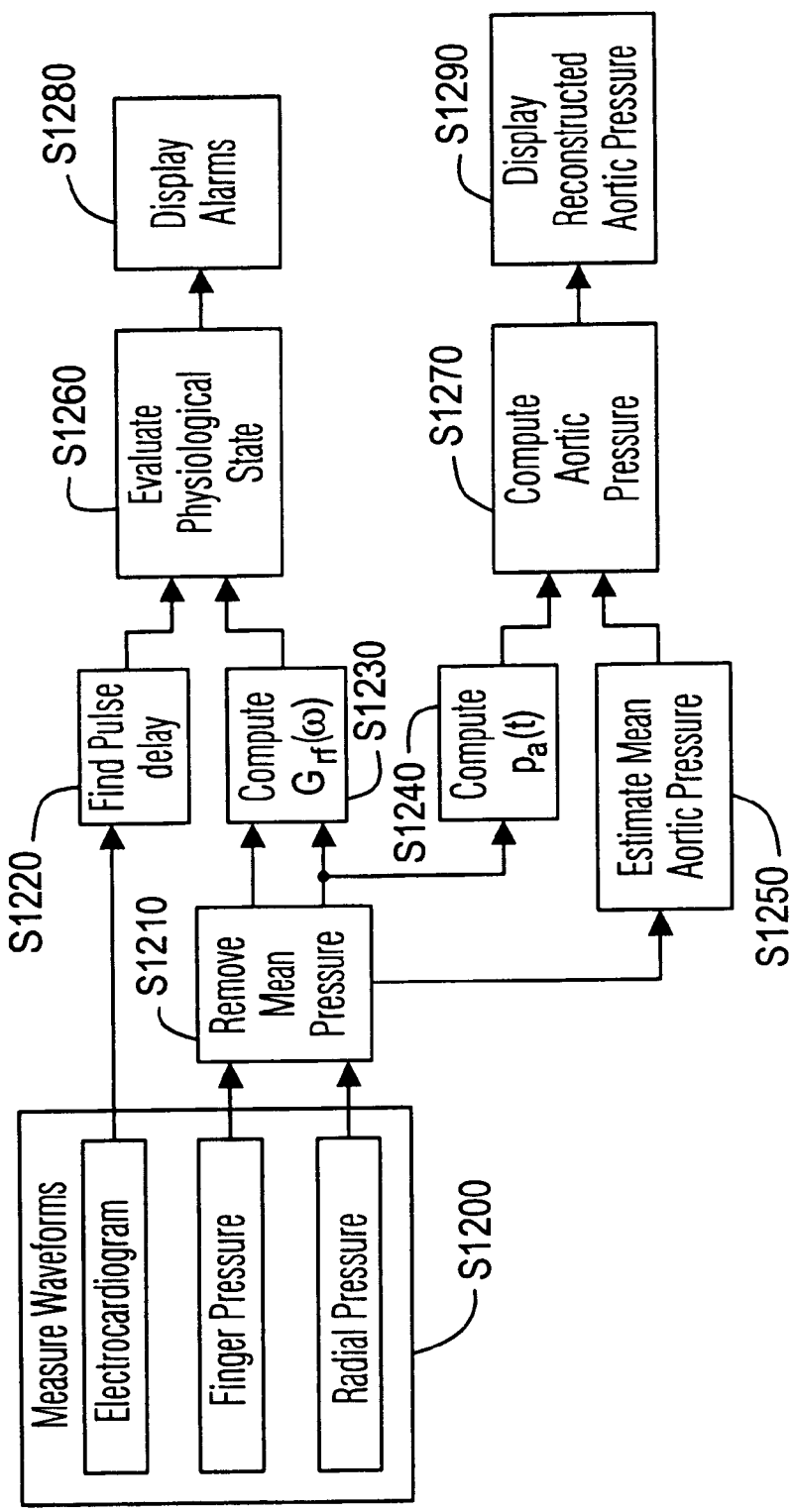
FIG. 20 illustrates a process for using an individualized radial-to-aortic blood pressure reconstruction model.

FIG. 20 illustrates an exemplary method for using the individualized radial-to-aortic blood pressure reconstruction model as constructed in FIG. 19. In this exemplary method, step S1200 is the simultaneous measurement of a signal, such as the ECG signal, indicating the start of the aortic blood pressure pulse, and the blood pressure pulse waveforms at the radial artery and fingertip. Control then proceeds to step S1210 in which the mean signal level is removed from the measured signals. Control then proceeds to S1220. In step S1220, the pulse propagation time ($\Delta t$) for each arterial segment is determined. Control then moves to step S1230. In step S1230, the radial-to-finger transfer function is calculated using the radial pressure waveform as the input and the finger pressure as the output. Control then proceeds to step S1240. In step S1240, a reconstruction of the aortic waveform is computed. Control then proceeds to step S1250. In step S1250, the mean aortic pressure is estimated. Control then proceeds to step S1260. In step S1260, the physiological state of the patient is evaluated. Control then proceeds to step S1270 in which an estimate of the mean aortic pressure is added to the reconstructed aortic pulse waveform to complete the model for continuously reconstructing the aortic blood pressure from the continuously measured radial pulse pressure. Control then proceeds to step S1280 where alarms are displayed. Control proceeds to step S1290 where the reconstructed aortic pressure is displayed.

Figure 22B:
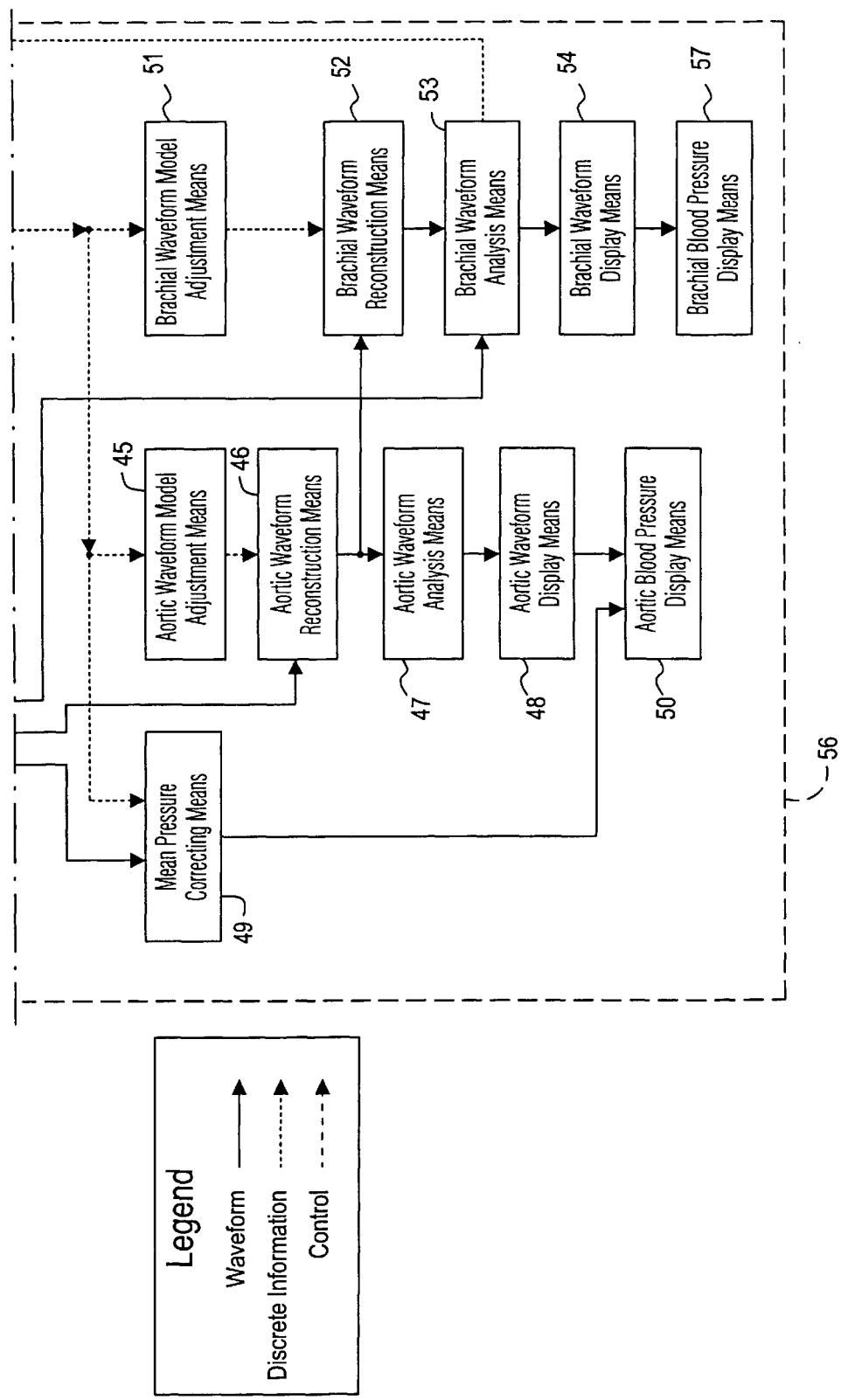
FIG. 22 illustrates a block diagram of the aortic waveform reconstruction device.

The exemplary embodiments of the invention use information acquired by conventional physiological monitoring devices that are widely used in medicine to monitor the health status of patients. However, these physiological monitoring devices and information are combined with a number of original methods and devices, as shown in FIG. 22, to reconstruct the aortic blood pressure in an effective new way. The components of patient monitors used in this invention include a subject information entry device 28, an electrocardiographic monitor 29, a QRS complex identification detector 30, a pulse delay time computing device 31, a heart rate computing device 32, a finger pulse monitor 33, a radial (or ulnar) blood pressure monitor 34 and a brachial blood pressure monitor 35.

The subject information entry device 28 provides a mechanism for manual or automatic entry of human subject data such as their gender, age, height, weight, and other information. Any conventional method suitable to the specific application of this invention can be used such as keyboards, touch pads, switches, and voice recognition systems. The electrocardiographic monitor 29 can be any of a number of devices that acquire and display a continuous waveform of the electrical activity of the heart. The QRS complex computing detector 30 determines the start time of the contraction of the ventricles of the heart. The pulse delay time computing device 31 determines the time of the start of each blood pressure pulse relative to the contraction of the ventricles of the heart. These circuits measure the time between the R-wave of the ECG and the arrival of the blood pressure pulse at each of the measurement sites. These times are saved and used later for characterizing the pulse propagation characteristics of the subject and adjusting the waveform reconstruction models.

The heart rate computing device 32 computes the heart rate using the time of each new heart beat and those of previous heart beats. The finger pulse monitor 33 produces a continuous measurement of the blood pressure waveform in the finger. The pressure pulse monitoring device may take the form of a plethysmograph such as an inflated cuff, photoelectric device, or electrical impedance measuring method which produces a continuous measurement of the changes in blood volume of the finger. Devices such as pressure transducers of any type inserted into the artery of the finger or connected to the finger artery by a fluid filled tube can also be used to produce the continuous measurement of the blood pressure waveform in the finger.

A radial (or ulnar) blood pressure monitor 34 continuously measures the blood pressure waveform in the radial artery or other point between the brachial and finger blood pressure measurement sites. The radial blood pressure monitor 34 may be an aplanation tonometer that continually monitors the pressure in an artery under the tonometer. Any device such as a pressure transducer of any type inserted into the radial artery or connected to the radial artery by a fluid filled tube can also be used to produce the continuous measurement of the blood pressure waveform in the radial artery. The radial blood pressure monitor 34 may also be implemented using a plethysmograph such as an inflated cuff, photoelectric device, or electrical impedance measuring method which produces a continuous measurement of the changes in blood volume of the radial artery.

The brachial blood pressure monitor 35 produces a continuous or intermittent measurement of the blood pressure and blood pressure waveform in the brachial artery. The brachial blood pressure monitor 35 first provides a measurement of the systolic mean, and diastolic pressures. The brachial blood pressure monitor 35 may be implemented using a pressure transducer inserted into the brachial artery or connected to the brachial artery by a fluid filled tube. Alternatively, the brachial blood pressure monitor 35 may be implemented using a NIBP monitor, which uses a pressurized cuff and one of many pulse sensing techniques for measurement of the blood pressure.

The system also includes a computational device and display, not shown, for controlling, processing, recording, displaying and communicating the waveforms and information acquired by the aforementioned physiological monitors 29, 33, 34 and 35 and the reconstructed aortic waveforms and blood pressure values produced by the method illustrated in FIG. 19. Any of the computational devices utilized in the system and method of the invention may be implemented in any of a number of electronic computational devices such as computers, microprocessors, and discrete computational circuits. Recording devices may be implemented using electronic or magnetic memory devices, recording media, paper, and other forms of information storage suitable to the application. The displays may be implemented using any of a number of electronic devices that display or produce printed representations of waveforms and numeric information for visual inspection.

The system and method also uses a number of devices and methods which may not be in every patient monitor but which are conventionally known and understood. For example, as shown in FIG. 22, the invention may use a measurement confirmation device 36, finger blood pressure waveform corrector 37, radial blood pressure waveform corrector 38 and brachial blood pressure waveform corrector 39.

The measurement confirmation device 36 determines whether the physiological signals acquired by the aforementioned monitoring devices 29, 33, 34 and 35 are being acquired and are of adequate quality for their intended purpose. The measurement confirmation device 36 compares the output of each of the aforementioned physiological monitoring devices 29, 33, 34 and 35 to predetermined features and characteristics of each signal type. This comparison is performed using templates and known ranges of values of signal features. Noise levels are determined and compared with maximum noise level limits.

The finger blood pressure waveform corrector 37, radial blood pressure waveform corrector 38 and brachial blood pressure waveform corrector 39 remove distortions and changes in the spectral distribution of the waveforms introduced by the instruments used in each of the monitoring devices 29, 33, 34 and 35. The waveform correction devices 37, 38 and 39 use the widely known method of using a filter that has a transfer function that is the inverse of the transfer function of the monitoring device. The specific filters used are predetermined for the specific monitoring devices used in each application, e.g., 29, 33, 34 and 35. The filters are stored within the permanent memory of the patient monitors.

Figure 23:
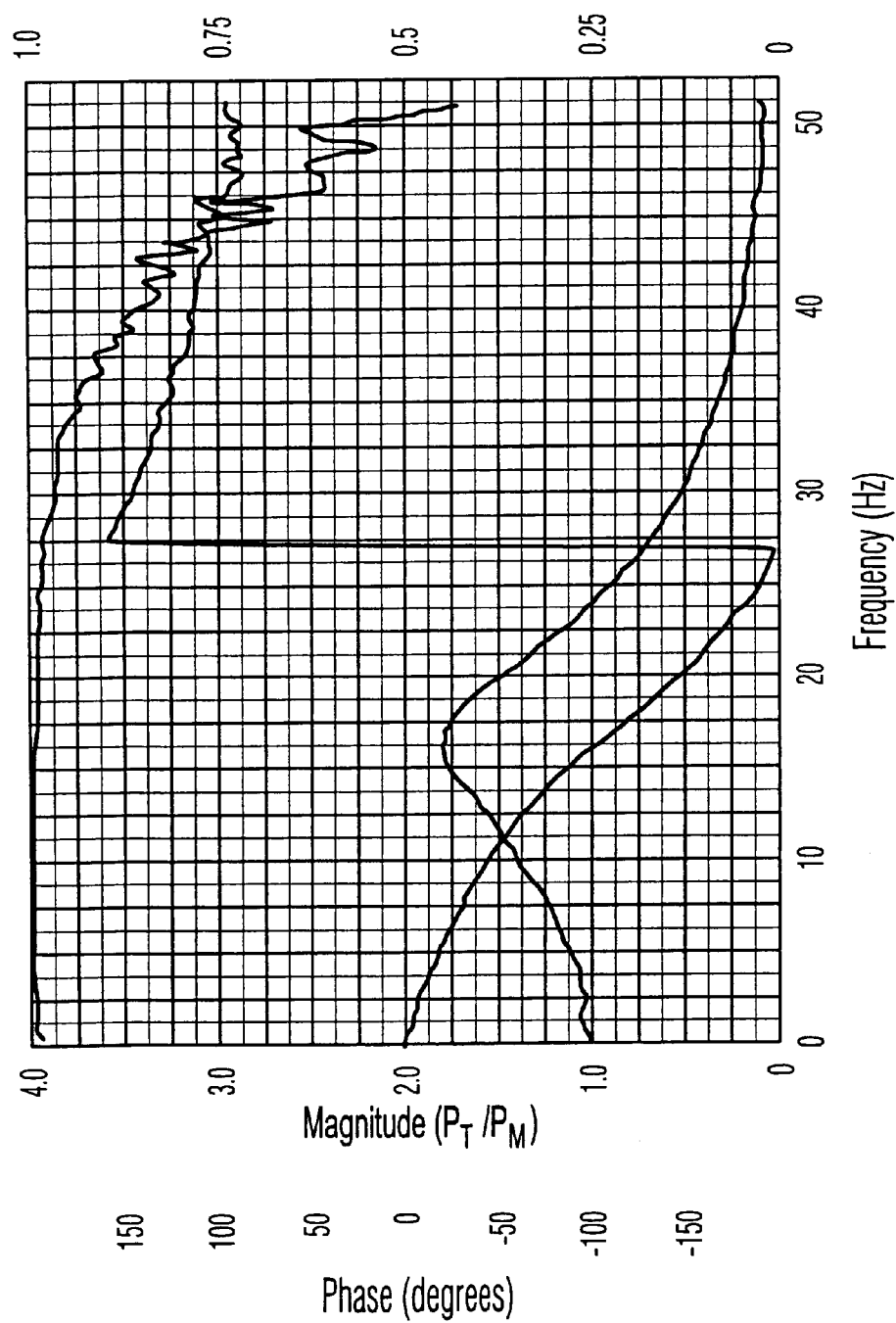
FIG. 23 illustrates a frequency response of a pressure transducer connected to an artery with a fluid filled catheter.
Figure 24:
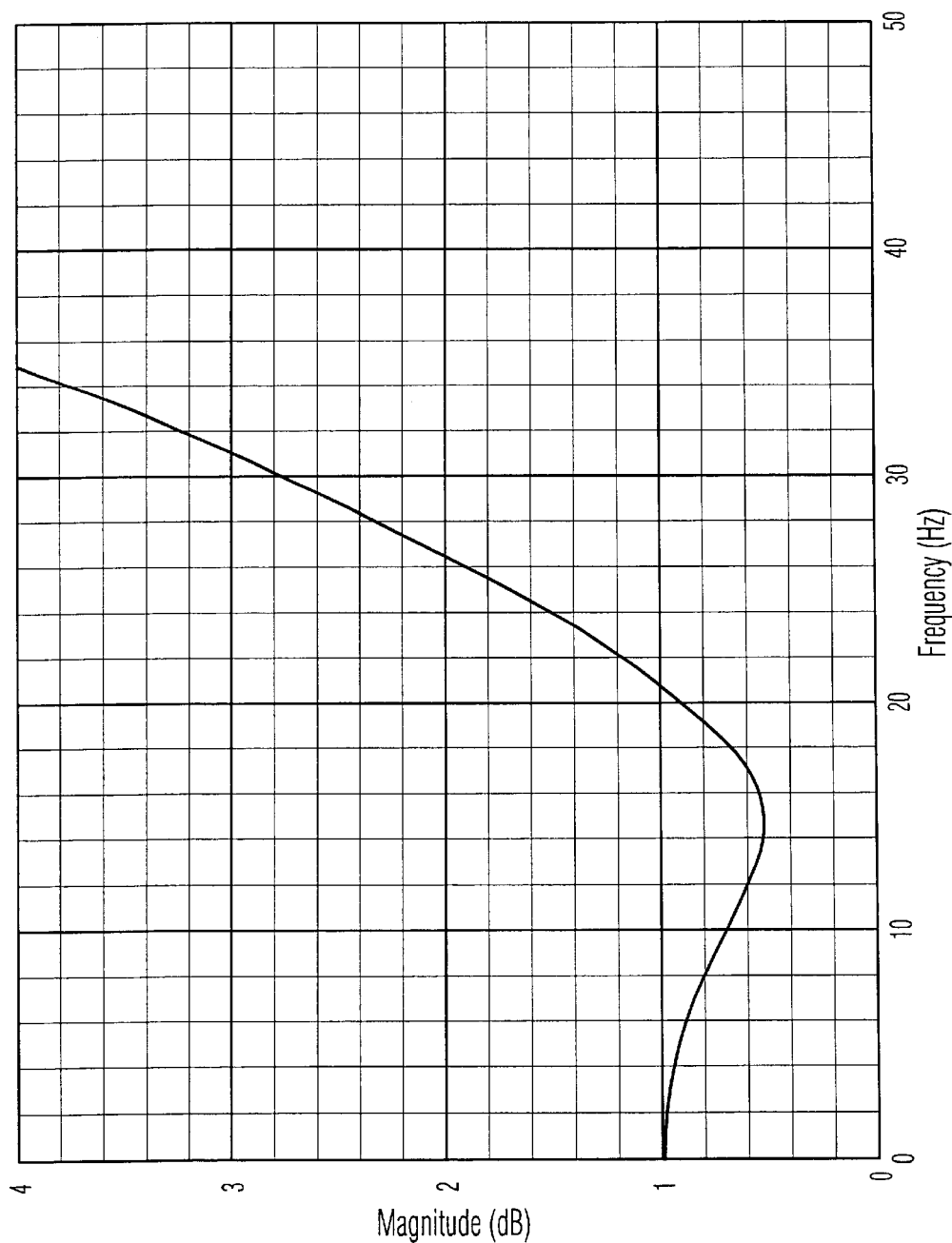
FIG. 24 illustrates a frequency response of a filter used to correct the waveform measured with the pressure transducer and fluid-filled catheter.

For example, a radial blood pressure monitor 34 may use a pressure transducer connected to the radial artery with a fluid filled tube having a transfer function closely approximated by an under-damped second order system as shown in FIG. 23. This response enhances frequency components of the blood pressure waveform near the resonance frequency of the transducer system. A filter used for correcting the distortions produced by the transducer frequency response has a transfer function which is the inverse of that of the transducer. An example of such a transfer function is shown in FIG. 24. In addition to using the inverse filter to correct the distortion produced by the transducer, the waveform correctors 37, 38 and 39 each contain a low pass filter for removal of unwanted high frequency noise so that each corrected signal has the same overall bandwidth.

The components of the invention which are not conventionally used in patient monitors are a finger-radial analyzer 40, radial-brachial waveform analyzer 41, brachial waveform analyzer 42, pulse wave propagation knowledge storage device 43, subject characterization device 44, aortic waveform model adapter 45, aortic blood pressure waveform reconstructor 46, aortic waveform analyzer 47, aortic blood pressure waveform display 48, mean blood pressure corrector 49, aortic blood pressure display 50, brachial waveform model adapter 51, brachial blood pressure waveform reconstructor 52, brachial waveform comparator 53 and brachial blood pressure display 54.

The finger-radial analyzer 40 computes the finger-to-radial artery transfer function from the pulse oximeter waveform and radial pressure waveform. The radial-brachial waveform analyzer 41 computes the radial to brachial transfer function from the radial and brachial pulse pressure waveforms. The brachial waveform analyzer 42 determines the aortic-to-brachial pulse propagation time when the occlusion cuff is fully inflated. The brachial waveform analyzer 42 corrects the ECG-to-brachial delay time for the pre-ejection period of the heart based upon the subject's current blood pressure, heart rate and morphology.

The pulse wave propagation knowledge storage device 43 includes a permanent information storage device such as electronic, magnetic, or electromagnetic storage circuits and media for the permanent storage of predetermined information. Any information storage device used in the invention may be electronic or magnetic storage devices, including, but not limited to, chips, disks or tapes of any size. The information stored in the permanent information storage device includes the generalized mathematical equations (models) used for reconstructing the aortic waveforms, equations for relating pulse wave propagation to patient characteristics (e.g., gender, age, height, and weight), filter coefficients for the waveform correctors 37, 38 and 39 and instructions for display to the user.

The subject characterization device 44 contains the logical rules and equations for combining information about the patient, the measurements being made on the patient, information derived from the analysis of the brachial, radial, and finger waveforms and the stored knowledge of pulse wave propagation to characterize the patient. Using this information, the subject characterization device 44 selects the appropriate models to be used for reconstructing the aortic blood pressure and directions for modifying the generalized model mathematical equations for reconstructing the aortic waveform from the radial waveform and for estimating the brachial waveform from the reconstructed aortic waveform.

The aortic waveform model adapter 45 modifies the generalized radial-to-aortic blood pressure model to fit the specific subject being monitored. The aortic blood pressure reconstructor 46 uses the individual radial-to-aortic blood pressure reconstruction model and the continuous radial blood pressure signal to produce a continuous representation of the aortic blood pressure. The aortic waveform analyzer 47 analyses the reconstructed aortic blood pressure waveform and extracts the systolic, mean, and diastolic pressure values for each pulse. The values are averaged in a fashion appropriate to the medical application. The blood pressure values are compared to predetermined or user set alarm thresholds to determine if the aortic blood pressure has moved outside a predetermined range.

The aortic blood pressure waveform display 48 transfers the reconstructed aortic blood pressure waveform to the patient monitor information display device in a way appropriate to the architecture and processes of the patient monitor. The mean blood pressure corrector 49 adjusts the measured radial pressure to correct for the aortic-to-radial pressure drop. The aortic blood pressure display 50 transfers the blood pressure levels to the patient monitor information display, not shown, in a way appropriate to the architecture and processes of the patient monitor. This transfer of information also includes the sounding or display of alarms should the aortic blood pressure have changed such that it is outside the predetermined limits. The brachial waveform model adapter 51 modifies the generalized aortic-to-brachial blood pressure model to fit the specific subject being monitored using an adaptation method such as those described in FIGS. 15 and 17 and the corresponding text.

The brachial waveform blood pressure reconstructor 52 uses the aortic-to-brachial blood pressure reconstruction model modified to the individual and the continuous reconstructed aortic blood pressure signal to provide a continuous representation of the brachial blood pressure to the brachial waveform comparator 53. The brachial waveform comparator 53 compares the reconstructed brachial blood pressure to the true brachial blood pressure measured by the brachial blood pressure monitor 35. An estimate of the error of the reconstructed aortic blood pressure is produced by the brachial waveform comparator 53 during this comparison process. The brachial blood waveform display 54 and brachial blood pressure display 57 transfer the estimated error of the reconstructed aortic blood pressure and the actual and reconstructed brachial blood pressure waveforms to the patient monitor information display in a way appropriate to the architecture and processes of the patient monitor.

The system controller 55 is operationally coupled to each of the devices 28–54, contained in the sub-system 56, so as to control the devices 28–54 to work in cooperation with each other, as explained above, to produce a reconstructed aortic blood pressure measurement.

Figure 25A:
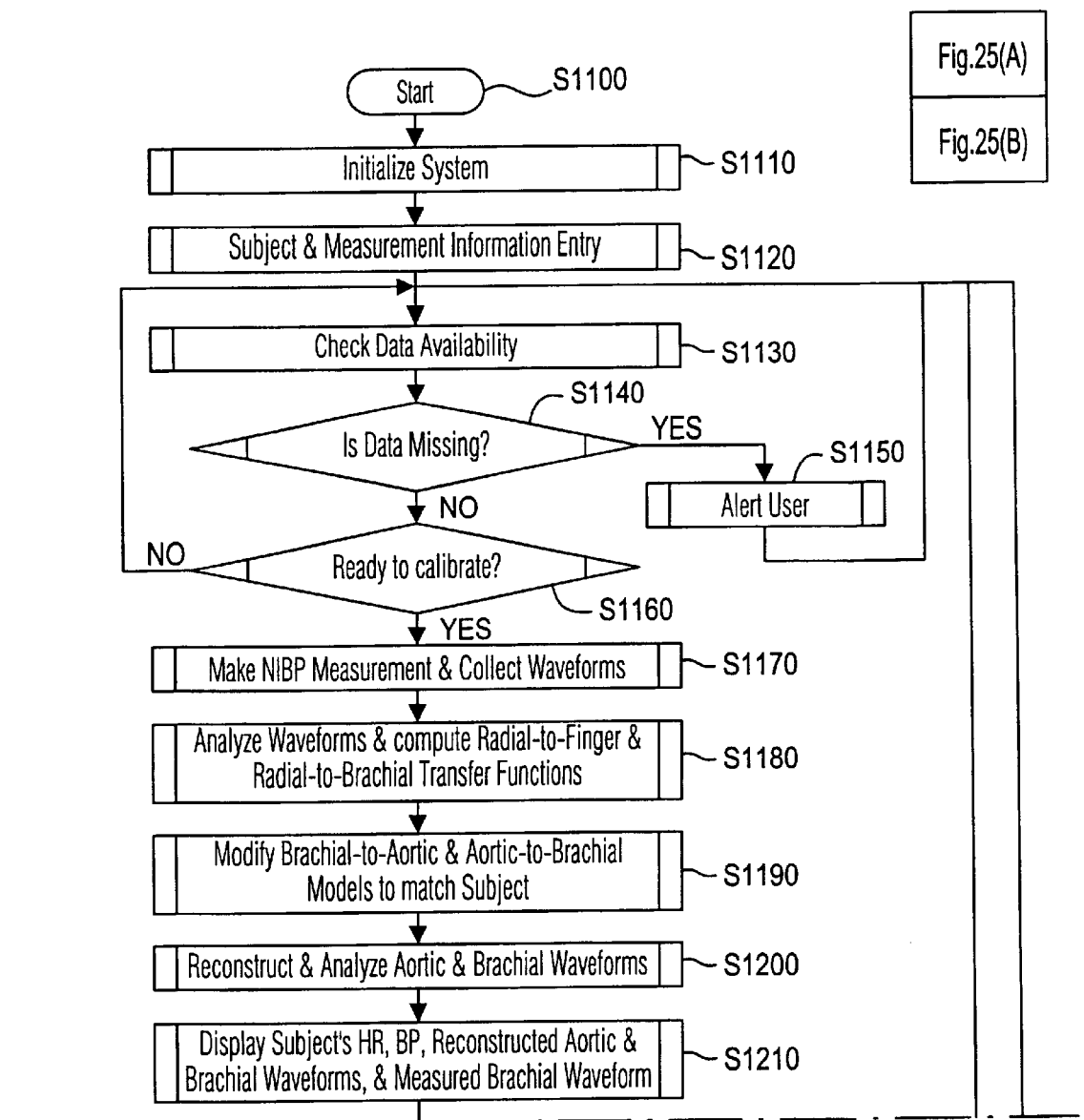
FIG. 25 illustrates an overall process of an aortic blood pressure reconstruction method according to the invention.
Figure 25B:
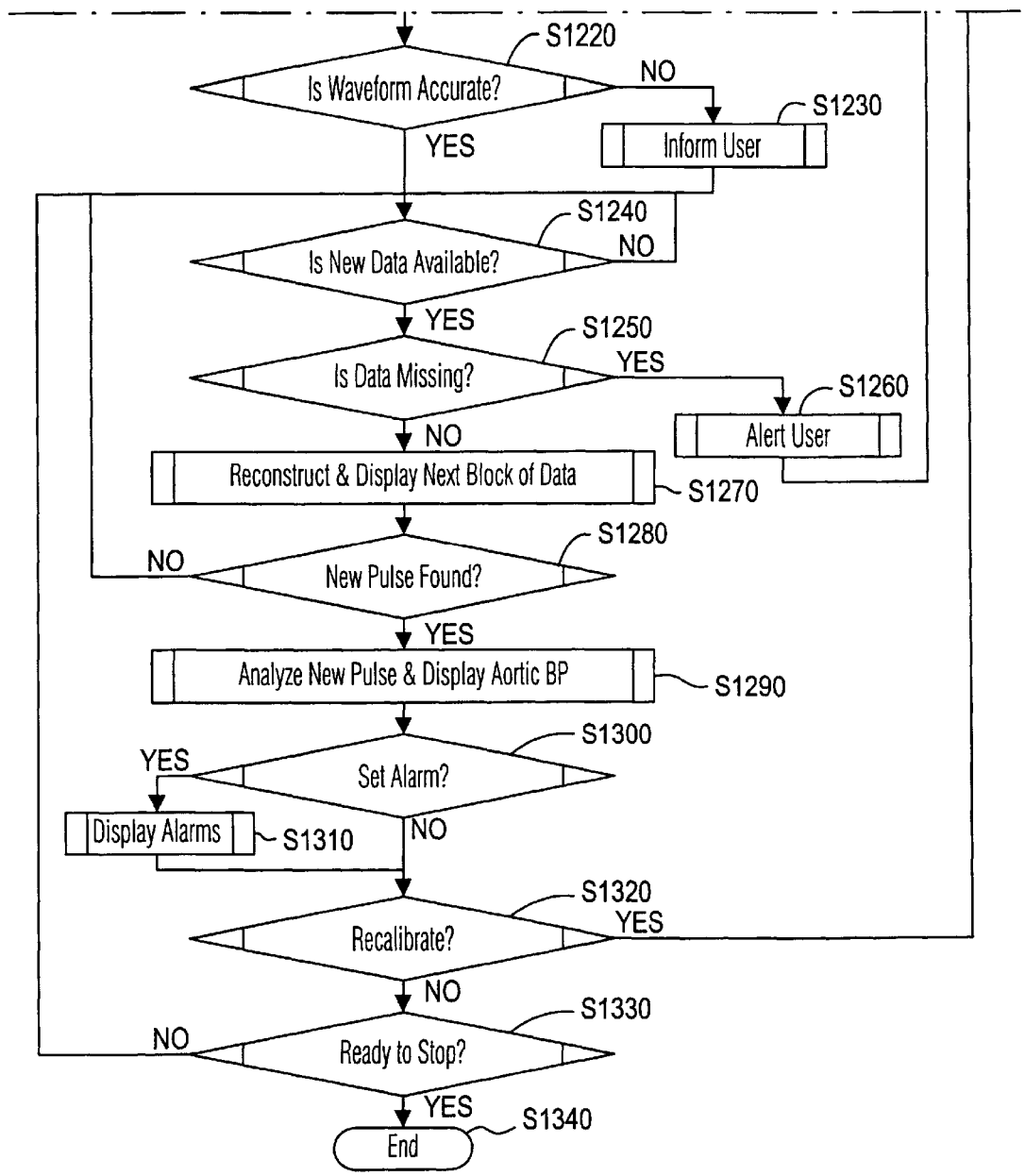

An exemplary method of performing aortic blood pressure reconstruction is shown in FIG. 25. The exemplary method does not include steps associated with the patient monitoring activities. The method is performed as an integrated part or parallel process to the patient monitoring processes.

After the start of the process at step S1100, control proceeds to step S110 in which the devices and processes are initialized. Control then proceeds to step S1120. At step S1120, the user is provided with instructions and requests for information concerning the patient and the measurement device being used. The patient information includes, for example, the subject's gender, age, height and weight. The information concerning the measurements being made includes, for example, the type of brachial pressure measurement (NIBP, direct transducer, etc.), cuff size, tubing length if NIBP, length of cuff tube or brachial transducer fluid filled catheter, type of radial measurement (tonometer, direct transducer, etc.), length of radial transducer fluid filled catheter if direct measurement, finger pressure waveform measurement (photo-plethysmographic, cuff plethysmograph, direct transducer, etc.), and length of cuff or transducer fluid filled transducer catheter.

After the necessary information has been entered, control proceeds to step S1130 in which availability of the necessary information and data to reconstruct the aortic waveform is determined. Control then proceeds to step S1140. In step S1140, the status of the data availability is checked. If data is not available, control continues to step S1150 in which the user is informed of the deficiency and the process returns to step S1130.

Alternatively, if all necessary information and data is available for reconstructing the aortic waveform, control proceeds to step S1160. At step S1160, a check is made to determine whether the overall patient monitor system is ready to begin the calibration process of the aortic reconstruction model process. If the patient monitor is not ready for calibration, control returns to step S1130. If the system is ready to calibrate the aortic reconstruction process, control proceeds to step S1170.

At step S1170, the brachial blood pressure is measured by any of several known oscillometric blood pressure measurement methods. At two times during the process of making the oscillometric blood pressure measurement, simultaneous samples of one or more beats of the ECG, brachial, radial, and finger blood pressure waveforms are recorded, corrected, and saved.

As shown in FIG. 21, the first instance occurs after the occlusion cuff has been inflated to a maximum pressure well above systolic pressure. After attainment of the maximum pressure, the cuff pressure is maintained at a constant level for a period of time. This period of time is sufficient to include one or more complete heart beats and the sensing of the blood pressure pulses produced by one or more heart beats. The cuff pressure is then allowed to deflate in a controlled fashion while the blood pressure is measured using a conventional non-invasive blood pressure measurement. Following the completion of the blood pressure measurement, the cuff pressure is allowed to fall to a pressure well below diastolic pressure that produces a minimum restriction of the underlying arterial vessel. The pressure is again held constant at this lower pressure for a period sufficient to include one or more complete heart beats and the sensing of the blood pressure pulses produced by one or more heart beats at all points in the pulse wave propagation path. The timing of this period in the cuff pressure measurement cycle is shown in FIG. 21.

Following NIBP measurement and collection of the waveform data in step S1170, control proceeds to step S1180. In step S1180, the collected waveforms are analyzed and the radial-to-finger and radial-to-brachial transfer functions are computed. Control then proceeds to step S1190.

In step S1190, the waveform data collected in step S1170 are modified in step S1190 and the waveform information combined with the patient information and wave propagation knowledge to characterize the patient. The radial-to-aortic and aortic-to-brachial reconstruction models are then adjusted to match the patient being monitored.

Following completion of step S1190, the aortic waveform is reconstructed in step S1200 using the segment of data collected during calibration in step S1170. The reconstructed aortic waveform is then passed through the brachial waveform reconstruction model to produce a reconstructed brachial blood pressure waveform. The error between the brachial blood pressure measured during calibration and the brachial blood pressure reconstructed from the reconstructed aortic waveform is then computed. Control then proceeds to step S1210.

In step S1210, the subject's heart rate and measured blood pressure parameters are displayed. The measured brachial blood pressure waveform is displayed with the reconstructed brachial blood pressure waveform along with the estimated error of the reconstructed waveforms. The reconstructed aortic blood pressure waveform is also displayed. Control then proceeds to step S1220.

In step S1220, the error of the reconstructed brachial waveform is compared with a figure of merit. If the error is too large, control proceeds to step S1230 in which a message is displayed to the user. If the user desires that the waveform be recalibrated, he makes his desire known by the pressing of a switch that is interrogated at S1320. If the error of the brachial waveform is less than the figure of merit, the calibration cycle is complete and the process continues on to S1240 to begin the aortic waveform reconstruction.

The aortic blood pressure process waits until a set of radial blood pressure data has been acquired by the patient monitor's data acquisition system. This is done by the process periodically checking for new data at step S1240. If data are not available, the process returns to the start of step S1240. If a new set of data are available, the process proceeds to step S1250 where a check is made to insure that all data needed for the aortic blood pressure reconstruction process are available. If any data are missing, the user is alerted with an alarm or displayed messages at step S1260. After alerting the user, control returns to step S1130 and waits until all data are again available. When all data is available, the calibration process at step S1140–S1210 is repeated.

If, in step S1250, all data needed for aortic waveform reconstruction are available, the aortic blood pressure is reconstructed, added to the end of any previously reconstructed blood pressure data, and displayed in step S1270. Control then proceeds to step S1280, in which the reconstructed aortic pressure data are checked to determine if the current cardiac cycle was completed during the new block of data. If the start of the next blood pressure pulse was not found, control returns to step S1240 and waits for the next block of data.

If the start of the next pulse is found, control proceeds to step S1290, in which the latest complete aortic blood pressure pulse is analyzed and the blood pressure parameters for the new pulse are computed. In step S1290, the new blood pressure parameters are combined with the parameters of previous pulses to produce average values and other statistics consistent with the specific patient monitoring application.

Control then proceeds to step S1300 in which the aortic blood pressure parameters are checked against predetermined alarm limits. If the parameters are out of tolerance, control proceeds to step S1310 in which alarms are displayed and control proceeds to step S1320. Alternatively, control proceeds directly to step S1320. In step S1320, a determination is made whether another calibration is required. Re-calibration conditions include predetermined periodic calibrations, user initiated calibrations, excessive changes in blood pressure, and signal degradation. If calibration is required, the process returns to step 1130.

If no calibration is required, control proceeds to step SI1330, in which a check is performed to determine if the user has requested that the aortic blood pressure process be stopped. If no stop command has been made, control returns to step S1240 to await the next block of data for processing. If a stop command has been received, control proceeds to step S1340 in which the aortic blood pressure reconstruction process is terminated.

While this invention has been described in conjunction with the specific embodiments outlined above, many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. A method that reconstructs the aortic blood pressure of a patient, the method comprising:

measuring a time reference for a start of each blood pressure pulse using an ECG as the pulse leaves the patient's aorta root;

measuring brachial blood pressure waveforms using a plethysmograph to produce blood pressure waveforms when blood pressure is held at a constant low level;

measuring a continuous radial or ulnar blood pressure waveform using a tonometer or blood pressure sensor in the artery;

measuring a continuous plethysmographic blood pressure waveform in the patient's finger using at least one pulse oximeter;

reconstructing aortic blood pressure waveforms using mathematical models that combine analytical models of pulse wave propagation in the cardiovascular system with an aortic waveform reconstruction model; and repeatedly adjusting the mathematical models to the patient and the patient's physiological state based upon the measurements of the ECG, the plethysmograph and the at least one pulse oximeter to produce a dynamic, patient-specific, reconstructed aortic waveform.

2. The method of claim 1, wherein the plethysmograph is an occlusion cuff of a NIBP monitor.

3. The method of claim 1, wherein the empirical aortic waveform reconstruction model is obtained from measurements performed on a large population of subjects.

4. The method of claim 3, wherein reconstructing aortic blood pressure waveforms is performed by normalizing the empirical aortic waveform reconstruction model using the subjects' wave-propagation characteristics and other information.

5. The method of claim 4, wherein, reconstructing the aortic blood pressure waveforms includes combining normalized empirical models into a single population average normalized model subsequent to normalizing the empirical aortic waveform reconstruction model.

6. The method of claim 4, wherein normalization is performed using mathematical descriptions of a human vascular system and measurements that account for individual subject's variations, non-uniformities, and non-linearities of the cardiovascular system.

7. The method of claim 1, further comprising verifying the dynamic, patient-specific, reconstructed aortic waveform model by using the dynamic, patient-specific, reconstructed aortic waveform model to reproduce the waveform at a first point in the patient's vascular system and comparing the reproduced waveform to a waveform measured at the first point.

8. A patient monitoring system that estimates blood pressure at a first site using a blood pressure measurement performed at a second site, the system comprising:

a system controller that controls operation of the patient monitoring system;

a first data storage device, operationally coupled to the system controller, that stores data about blood pressure pulse wave propagation;

a first communication device, operationally coupled to the system controller, by which a user provides information about a patient and the measurement device;

a first blood pressure pulse measurement device, operationally coupled to the system controller, that continuously measures the blood pressure at the second site to produce a first blood pressure measurement;

a first computational device, operationally coupled to the system controller, that constructs a first mathematical relationship using the data stored in the first data storage device to estimate blood pressure at the first site using the first blood pressure measurement;

a first blood pressure measurement modification device, operationally coupled to the system controller, that produces a second blood pressure measurement by removing a mean pressure from the first blood pressure measurement;

a first blood pressure measurement comparator, operationally coupled to the system controller, that compares the estimated blood pressure at the first site with the second blood pressure measurement;

a second communication device, operationally coupled to the system controller, that transfers results of the first blood pressure measurement device, first computational device, first blood pressure measurement modification device and the first blood pressure measurement comparator to a user or a second data storage device;

a systole detector, operationally coupled to the system controller, that detects initiation of a blood pressure pulse;

a third data storage device, operationally coupled to the system controller, that retains the mean pressure removed from the first blood pressure measurement for recombination with the estimated blood pressure at the first site;

an artery occlusion device, operationally coupled to the system controller, that temporarily restricts blood flow in a path of the vascular system between a heart and the second site;

a second blood pressure pulse measurement device, operationally coupled to the system controller, that measures a third blood pressure measurement, or a representation thereof, at, or proximate to, the artery occlusion device;

a third blood pressure pulse measurement device, operationally coupled to the system controller, that measures a fourth blood pressure measurement, or a representation thereof, at a third point that is at, or proximate to, an end of a blood pressure pulse propagation path;

a second blood pressure measurement modification device, operationally coupled to the system controller, that modifies the fourth blood pressure measurement by removing changes in the measurement produced by frequency response characteristics of the third blood pressure pulse measurement device;

a pulse propagation time determination device, operationally coupled to the system controller, that measures a time required for the blood pressure pulse of a given heart beat to travel to the first, third and fourth blood pressure measurement sites from the heart and times required for the blood pressure pulse to travel between each of the first, third and fourth pulse measurement sites;

a second computational device, operationally coupled to the system controller, that uses information from any of the first data storage device, the first blood pressure measurement comparator, the systole detector, the first, second and third data storage devices, the artery occlusion device, the first blood pressure measurement modification device, the first and second blood pressure measurement devices and the pulse propagation time determination device, to construct a computational relationship between the blood pressure measured by the blood pressure measurement device and the blood pressure at the first site;

a third computational device, operationally coupled to the system controller, that uses the estimate of the blood pressure at the first site to produce a second estimate of the blood pressure measurement at the second and third sites;

a fourth computational device, operationally coupled to the system controller, that continuously estimates the blood pressure at the third site from the blood pressure measured at the second site;

a second blood pressure measurement comparator, operationally coupled to the system controller, that continuously compares the blood pressure measured at the third site to the estimated blood pressure at the third site and the propagation time between the first and third sites to produce a measurement indicating whether the first mathematical relationship is accurate; and an optimizer, operationally coupled to the system controller, that adjusts the first mathematical relationship to improve accuracy with which the system estimates blood pressure at the first site.

9. The system of claim 8, further comprising:

a second blood pressure measurement modification device, operationally coupled to the system controller, and the first blood pressure measurement device, that modifies the first blood pressure measurement by removing changes in the first blood pressure measurement produced by frequency response characteristics of the first blood pressure measurement device; and a third blood pressure measurement modification device, operationally coupled to the system controller and the third blood pressure measurement device, that modifies the third blood pressure measurement by removing changes in the third blood pressure measurement produced by frequency response characteristics of the second blood pressure measurement device.

10. The system of claim 8, wherein the first, second and third data storage devices are electronic, magnetic or electromagnetic storage devices.

11. The system of claim 8, wherein the systole detector determines a start time of a given pulse using a device for measuring electrical activity of the heart and known empirical relationships of heart rate, blood pressure and patient characteristics to a time period between the given pulse start time and a time of opening of the heart's aortic valve.

12. The system of claim 8, wherein the systole detector determines a start time of a given pulse using a device for measuring electrical activity of the heart and sounds produced by closing of the heart's valves and a device for determining the opening of the heart's aortic valve based upon timing of the given pulse start time and the heart sounds.

13. The system of claim 8, wherein, any of the first, second and third blood pressure measurement devices is a continuous, blood pressure measurement device comprising one of:
- a pressure transducer directly inserted into an artery;
- a pressure transducer connected to an interior of the artery by a fluid filled tube or catheter; and
- a tonometer that indirectly measures pressure in an underlying artery.

14. The system of claim 8, wherein the first blood pressure pulse measurement device is either a high pass filter with a low frequency cutoff below a frequency of blood pressure information contained in the first blood pressure measurement or a device that calculates the first blood pressure pulse measurement as a mean blood pressure using an equation empirically derived from blood pressure measurements performed by the first blood pressure measurement device.

15. The system of claim 8, wherein the combination of the artery occlusion device and the second blood pressure pulse measurement device comprises either:
- an automatic non-invasive blood pressure monitor comprised of an air-filled cuff wrapped around the patient's limb, a cuff pressure measurement device, a cuff pulse measurement device, and a monitor controller; or
- a combination of a pressurized, fluid-filled occlusion cuff, pressure controller and a separate device for measuring the blood pressure pulse such as a pressure sensing device pressed against the patient's skin over an underlying artery, and ultrasonic or electrical impedance measurement device that measures a volumetric change of the underlying artery by introduction of electromagnetic energy into the underlying artery.

16. The system of claim 8, wherein the third blood pressure measurement device measures a shape of a blood pressure waveform to directly or indirectly produce a measurement that is proportional to blood pressure pulse pressure.

17. The system of claim 8, wherein the third blood pressure measurement device measures a shape of a blood pressure waveform directly or indirectly, the third blood pressure measurement device comprising:
- a pulse oximeter that produces a continuous measurement of a change in volume of a finger artery produced by a blood pressure pulse;
- a finger cuff blood pressure monitor that continuously monitors a change in blood pressure in the finger; or
- one of a finger plethysmograph that uses an inflated cuff or an electrical impedance and strain gauge that continuously measure the volumetric change of the finger artery caused by the blood pressure pulse.

18. The system of claim 9, wherein any of the first, second and third blood pressure measurement modification devices comprises:
- a two stage filter, a first stage of the two stage filter being constructed to have a frequency response which is an inverse of a frequency response of the blood pressure measurement modification device in which the two stage filter is used, wherein characteristics of the first stage of the two stage filter are selected from frequency response characteristics based upon information entered in the first communication device that identifies a blood pressure pulse device being used, and, a second stage of the two stage filter is a low pass filter that has a fixed cutoff frequency.

19. The system of claim 8, wherein the pulse propagation time determination device comprises:
- a detection circuit that identifies an arrival time of a blood pressure pulse at a given location by identifying a diastolic or minimum point of a blood pressure waveform point of a preceding waveform and subtracting a systolic time from the arrival time at the given location.

20. The system of claim 8, wherein the system controller comprises:
- a computational device or electromechanical device that controls operation of the occlusion cuff, first, second and third blood pressure measurement devices, and first, second, third and fourth computational processes according to a predetermined series of actions necessary to produce a reconstructed aortic blood pressure measurement.

21. The system of claim 8, wherein the first computational device comprises:
- a first constituent device that computes a natural frequency of an aortic-to-brachial pressure segment of a pulse propagation path from an aortic-to-brachial pulse propagation time measured when the occlusion cuff at the second site is inflated to a pressure above a systolic pressure;
- a second constituent device that determines radial-to-finger pulse propagation characteristics from measured radial and finger pulse waveforms and a mathematical relationship that describes a finger-to-radial segment of the pulse propagation path;
- a third constituent device that determines brachial-to-radial pulse propagation characteristics from measured brachial and radial pulse waveforms and a mathematical relationship that describes a radial-to-brachial segment of the pulse propagation path;
- a fourth constituent device that estimates a damping coefficient of the brachial-to-aortic segment of the pulse propagation path from values of the aortic-to-brachial natural frequency and the pulse propagation characteristics of the finger-to-radial and radial-to-brachial segments;
- a fifth constituent device that constructs a mathematical relationship that describes the brachial-to-aortic segment of the propagation path using the natural frequency of the aortic-to-brachial segment and the estimated damping coefficient of the aortic-to-brachial segment;
- a sixth constituent device that combines the brachial-to-aortic and radial-to-brachial mathematical relationships to form a radial-to-aortic pulse propagation relationship;
- a seventh constituent device that constructs a mathematical relationship that describes the aortic-to-brachial segment of the propagation path using the natural frequency of the aortic-to-brachial segment and an estimated damping coefficient of the aortic-to-brachial segment;
- an eighth constituent device that transforms the radial-to-aortic pulse propagation relationship to a time-domain mathematical relationship that produces an estimate of the aortic pulse pressure waveform from a radial pulse pressure waveform measurement; and
- a ninth constituent device that transforms the aortic-to-brachial pulse propagation relationship to a time-domain mathematical relationship that produces an estimate of a brachial pressure from an estimate of an aortic pulse pressure waveform.

22. The system of claim 21, wherein, the second computational device comprises:
- a tenth constituent device that estimates an aortic blood pressure waveform from at least one of the pressure measurements made by the first blood pressure measurement device using the radial-to-aortic pulse propagation relationship;
- an eleventh constituent device that modifies the retained first blood pressure measurement mean pressure using a mathematical relationship that correlates damping coefficients of individual segments of the pulse propagation path to a mean pressure decrease from the aorta to the first blood pressure measurement site;
- an adder that adds the modified mean pressure produced by the eleventh constituent circuit to a series of estimated aortic pulse pressures;
- a synchronizer that synchronizes the estimated aortic pressure to the estimated time of systole;
- a first constituent display that displays the estimated aortic pressure in a form suitable for visual assessment; and
- a twelfth constituent device that determines and displays the estimated aortic blood pressure parameters including but not limited to the systolic, mean, diastolic pressures and the rate of change of pressure during systole.

23. The system of claim 22, wherein the third computational device comprises:
- a thirteenth constituent device that computes estimates of the brachial blood pressure waveform corresponding in time to the brachial waveforms obtained from estimates of the aortic pressure waveform using the aortic-to-brachial relationship;
- a fourteenth constituent device that adjusts the relative timing of the estimated brachial waveform to the measured brachial waveform such that minimums of the estimated and brachial waveforms are synchronous; and
- a second constituent display that displays and retains the estimated brachial waveform and measured brachial waveform for visual assessment.

24. The system of claim 23, wherein the fourth computational device comprises:
- a fifteenth constituent device that continuously computes estimates of a finger blood pressure waveform using a measured radial waveform and the radial-to-finger pulse propagation relationship; and
- a sixteenth constituent device that adjusts relative timing of the estimated finger blood pressure waveform to the measured finger blood pressure waveform such that the minimums of the estimated and measured finger blood pressure waveforms are synchronous.

25. The system of claim 24, wherein the first blood pressure measurement comparator comprises:
- a seventeenth constituent device that computes estimates of a brachial blood pressure waveform corresponding in time to the brachial waveforms obtained from estimates of the aortic pressure waveform using the aortic-to-brachial relationship to produce an estimated aortic blood pressure error as a worst case estimate of estimated aortic blood pressure error;
- an eighteenth constituent device that computes a root mean square difference between the measured brachial waveform and the estimated brachial waveform to produce a root square error as a measure of waveform fidelity;
- a third constituent display that displays the estimated aortic blood pressure error and root mean square error for visual assessment;
- a nineteenth constituent device that compares the estimated aortic blood pressure error and root mean square error to predetermined limits stored in one of the first, second or third data storage devices;
- a first constituent indicator that informs a user that an accuracy of the estimated aortic pressure is outside predetermined limits based on the comparison performed by the nineteenth constituent device; and
- a first constituent re-calibration initiator that initiates a re-calibration of the radial-to-aortic blood pressure reconstruction device.

26. The system of claim 25, wherein the second comparison device comprises:
- a twentieth constituent device that computes a difference in amplitude of the measured finger blood pressure pulse waveform and the estimated finger blood pressure pulse waveform as a first index of a state of the patient's vascular system;
- a twenty-first constituent device that computes a root mean square difference between the measured finger blood pressure pulse waveform and the estimated finger blood pressure pulse waveform as a second index of the state of the patient's vascular system;
- a twenty-second constituent device that retains the finger blood pressure pulse waveform measurement amplitude mean difference and the root mean square difference made at a time of calibration of the aortic blood pressure reconstruction device;
- a twenty-third constituent device that compares a most recent finger blood pressure pulse waveform measurement amplitude mean difference and root mean square difference to the retained from the last calibration to a set of limits stored in at least one of the first, second and third data storage devices;
- a second constituent indicator that informs a user that an accuracy of the estimated aortic pressure is outside the predetermined limits based on the comparison performed by the twenty-third constituent device; and
- a second constituent re-calibration initiator that initiates a re-calibration of the radial-to-aortic blood pressure reconstruction device.

27. The system of claim 26, wherein the optimization device comprises:
- a twenty-fourth constituent device that compares the mean amplitude difference and root mean square difference of the estimated brachial pressure waveform and measured brachial waveform to predetermined accuracy standards stored in at least one of the first, second or third data storage devices;
- a twenty-fifth constituent device that adjusts the brachial-to-aortic mathematical relationship if the mean amplitude difference and RMS difference of the brachial-to-aortic waveform do not meet the accuracy standards;
- a twenty-sixth constituent device that reconstructs the radial-to-aortic and aortic-to-brachial mathematical relationships and re-computes the aortic blood pressure and brachial blood pressure waveforms;
- a constituent controller that controls the twenty-fourth constituent device, twenty-fifth constituent device and twenty-sixth constituent device to operate until the mean amplitude difference and root mean square differences of the brachial-to-aortic waveform meet the predetermined accuracy standards or achieve a minimum error; and a third constituent indicator that informs the user that the accuracy of the estimated aortic pressure is outside the predetermined limits.

28. A method for estimating a patient's aortic pressure waveform comprising:

constructing an aortic pressure estimation mathematical relationship by creating a time domain equation obtained by taking an inverse transform of a radial-to-aortic transfer function constructed by dividing a radial-to-finger transfer function, computed from measurements of the patient's radial and finger blood pressure waveforms, by a product of three second order transfer functions, each transfer function representing a segment of a blood pressure pulse propagation path, and each transfer function incorporating parameters determined for the patient by numerical analysis of the measurement of the patient's radial and finger blood pressure pulse waveforms, and calculating a patient's aortic pressure waveform by using said time domain equation.

* * * * *